(12) United States Patent
Collingwood et al.

(10) Patent No.: US 7,803,804 B2
(45) Date of Patent: Sep. 28, 2010

(54) SUBSTITUTED PYRAZINES FOR USE IN THE TREATMENT OF INFLAMMATORY OR ALLERGIC CONDITIONS

(75) Inventors: Stephen Paul Collingwood, Horsham (GB); Nichola Smith, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/158,481

(22) PCT Filed: Dec. 20, 2006

(86) PCT No.: PCT/EP2006/012314

§ 371 (c)(1),
(2), (4) Date: Jun. 20, 2008

(87) PCT Pub. No.: WO2007/071396

PCT Pub. Date: Jun. 28, 2007

(65) Prior Publication Data

US 2008/0312217 A1    Dec. 18, 2008

(30) Foreign Application Priority Data

Dec. 22, 2005  (GB) ................. 0526240.7

(51) Int. Cl.
*A61K 31/4965* (2006.01)
(52) U.S. Cl. ................. 514/255.06; 544/409
(58) Field of Classification Search ............ 514/255.06; 544/409
See application file for complete search history.

(56) References Cited

FOREIGN PATENT DOCUMENTS

| WO | WO01/05773 A1 | 1/2001 |
|----|---------------|--------|
| WO | WO2005/016879 | 2/2005 |
| WO | WO2005/025496 A2 | 3/2005 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*

* cited by examiner

Primary Examiner—James O Wilson
Assistant Examiner—Douglas M Willis
(74) Attorney, Agent, or Firm—Paul D. Strain, Esq.; Fanelli Strain & Haag PLLC

(57) ABSTRACT

Disclosed herein are substituted pyrazine compounds and tautomers, stereoisomers, solvates, or pharmaceutically acceptable salts thereof for the treatment of conditions mediated by the blockade of an epithelial sodium channel, particularly an inflammatory or allergic condition, including compounds of formula I:

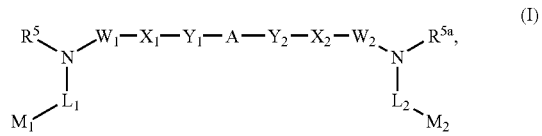

3 Claims, No Drawings

SUBSTITUTED PYRAZINES FOR USE IN THE TREATMENT OF INFLAMMATORY OR ALLERGIC CONDITIONS

CROSS-REFERENCE TO RELATED APPLICATIONS

This application is a U.S. national stage entry of PCT/EP2006/012314, filed Dec. 20, 2006, which claims priority to UK application number 0526240.7, filed Dec. 22, 2005, each of which is incorporated herein in its entirety.

BACKGROUND OF THE INVENTION

Not applicable.

DETAILED DESCRIPTION OF PREFERRED EMBODIMENTS

This invention relates to organic compounds, their preparation and use as pharmaceuticals.

In one aspect, the present invention provides compounds of formula (I):

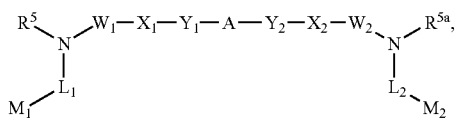

or tautomers, or stereoisomers, or solvates, or pharmaceutically acceptable salts thereof, wherein M, $M_1$ and $M_2$ are independently

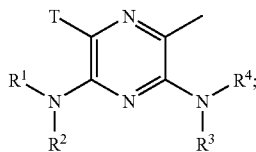

$R^1$, $R^2$, $R^3$, and $R^4$ are independently selected from H, $C_1$-$C_8$-alkyl, $C_1$-$C_8$-alkyl-carboxy, $C_1$-$C_8$-haloalkyl, $C_3$-$C_{15}$-carbocyclic group, $C_1$-$C_8$-alkylcarbonyl, $C_1$-$C_8$-alkoxycarbonyl, a $C_6$-$C_{15}$-membered aromatic carbocyclic group, a 4- to 14-membered heterocyclic group, a $C_1$-$C_8$alkyl substituted by a 4- to 14-membered heterocyclic group, and a $C_1$-$C_8$-alkyl substituted by a $C_6$-$C_{15}$-membered aromatic carbocyclic group, or $R^1$ and $R^2$ with the nitrogen atom to which they are attached form a $C_3$-$C_{14}$-membered heterocyclic group optionally substituted by $R^{14}$, or $R^3$ and $R^4$ with the nitrogen atom to which they are attached form a $C_3$-$C_{14}$-membered heterocyclic group optionally substituted by $R^{14}$;

L, $L_1$ and $L_2$ are independently selected from:

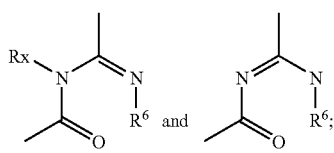

$R^6$, $R^5$, $R^{5a}$, $R^{5b}$ and $R^x$ are independently selected from H, $C_1$-$C_8$ alkyl, $C_1$-$C_8$-alkyl-carboxy, $C_1$-$C_8$-alkyl-alkoxy, $C_1$-$C_8$-haloalkyl, $C_3$-$C_{15}$-carbocyclic group, $C_1$-$C_8$-alkylcarbonyl, $C_1$-$C_8$-alkoxycarbonyl, nitro, cyano, a $C_6$-$C_{15}$-membered aromatic carbocyclic group, a 4- to 14-membered heterocyclic group, a $C_1$-$C_8$-alkyl substituted by a 4- to 14-membered heterocyclic group, and a $C_1$-$C_8$-alkyl substituted by a $C_6$-$C_{15}$-membered aromatic carbocyclic group, or $R^5$ with the nitrogen atom to which it is attached, together with A, form a 4- to 14-membered heterocyclic group when $X_1$ is $C_0$-$C_8$-alkylene, O, —$NR^7$— or S, or $R^{5a}$ with the nitrogen atom to which it is attached, together with A, form a 4- to 14-membered heterocyclic group when $X_2$ is $C_0$-$C_8$-alkylene, O, —$NR^7$— or S, or $R^{5b}$ with the nitrogen atom to which it is attached, together with A, form a 4- to 14-membered heterocyclic group when X is $C_0$-$C_8$alkylene, O, —$NR^7$— or S;

W, $W_1$ and $W_2$ are independently selected from $C_0$-$C_8$-alkylene;

X, $X_1$ and $X_2$ are independently selected from $C_0$-$C_8$-alkylene, O, S, —$NR^7$—, $NR^7(C{=}O)$—, —$NR^7(C{=}O)NR^8$—, —$NR^8SO_2$—, —$NR^7(SO_2)NR^8$—, —$NR^7(C{=}O)O$—, —$O(C{=}O)$—, —$O(C{=}O)O$—, —$O(C{=}O)NR^7$—, —$(C{=}S)NR^7$—, —$(C{=}NR^7)NR^8$—, —$(C{=}O)NR^7$—, —$(C{=}O)O$—, —$(SO_2)(C_0$-$C_8$-alkylene)-, —$(SO_2)NR^8$— and —$(SO_2)NR^7$—Z—$(SO_2)NR^8$—;

Y, $Y_1$ and $Y_2$ are independently —$C_0$-$C_8$-alkylene-;

Z is $C_1$-$C_4$-alkylene;

where W, $W_1$, $W_2$, Y, $Y_1$, $Y_2$ and Z are optionally substituted by $C_1$-$C_8$-alkyl, halogen, $C_1$-$C_8$-alkoxy, carboxy, $C_1$-$C_8$-alkyl-carboxy, $C_1$-$C_8$-haloalkyl, $C_1$-$C_8$-haloalkoxy, $C_3$-$C_{15}$-carbocyclic group, $C_1$-$C_8$-alkylcarbonyl, $C_1$-$C_8$-alkoxycarbonyl, nitro, cyano, a $C_6$-$C_{15}$-membered aromatic carbocyclic group, a $C_1$-$C_8$alkyl substituted by a $C_6$-$C_{15}$-membered aromatic carbocyclic group, a 4- to 14-membered heterocyclic group containing at least one ring heteroatom selected from the group consisting of nitrogen, oxygen and sulphur, a $C_1$-$C_8$-alkyl substituted by a 4- to 14-membered heterocyclic group containing at least one ring heteroatom selected from the group consisting of nitrogen, oxygen and sulphur, and a $C_1$-$C_8$-alkyl substituted by a $C_6$-$C_{15}$-membered aromatic carbocyclic group;

A is selected from a $C_6$-$C_{15}$-membered aromatic carbocyclic group optionally substituted by —Y—X—W—$NR^{5b}$-L-M, $C_3$-$C_{15}$-carbocyclic group optionally substituted by —Y—X—W—$NR^{5b}$-L-M, a 4- to 14-membered heterocyclic group optionally substituted by —Y—X—W—$NR^{5b}$-L-M, a heteroatom selected from nitrogen, oxygen, and sulphur, wherein the nitrogen can be substituted by —Y—X—W—$NR^{5b}$-L-M, a $C_1$-$C_8$alkyl optionally substituted by —Y—X—W—$NR^{5b}$-L-M, with the proviso that when $R^5$ and $R^{5a}$ does not form a 4- to 14-membered heterocyclic group with A, then A is not a $C_6$-$C_{15}$-aromatic carbocyclic group, O, C=O or a $C_1$-$C_8$-alkyl group when $X_1$, $X_2$, $Y_1$ and $Y_2$ are $C_0$-$C_8$-alkylene unless A is substituted by —Y—X—W—$NR^{5b}$-L-M;

$R^7$, $R^8$, $R^{11}$ and $R^{12}$, are independently selected from H, $C_1$-$C_8$-alkyl optionally substituted by $C_7$-$C_{14}$-aralkyl, $C_1$-$C_8$-haloalkyl and a 5- to 14-membered heterocyclic group; $R^7$ and $R^8$, independently, by way of a $C_1$-$C_4$-alkyl group can form a bond with a carbon atom of group W, $W_1$, $W_2$, Y, $Y_2$, or $Y_2$ to create a 5- to 14-membered heterocyclic group;

T is selected from H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, a and a $C_1$-$C_8$-alkyl substituted by a $C_6$-$C_{15}$-membered aromatic carbocyclic group;

wherein each $C_6$-$C_{15}$-membered aromatic carbocyclic group and each 4- to 14-membered heterocyclic group, unless otherwise specified is independently optionally substituted by one or more groups selected from OH, $C_1$-$C_8$-alkoxy, $C_1$-$C_8$-alkyl, halogen, $SO_2NR^{11}R^{12}$, hydroxy$C_1$-$C_8$-alkoxy, optionally substituted by hydroxyl, $(C_0$-$C_4$-alkylene) $CONR^{11}R^{12}$, $(C_0$-$C_4$-alkylene)$N=C(NR^{11}R^{12})_2$, —O—$(C_1$-$C_4$-alkylene)-$N=C(NR^{11}R^{12})_2$, —O—$(C_1$-$C_4$-alkylene)-$CONR^{11}R^{12}$, $C_6$-$C_{10}$-aralkoxy, $C_7$-$C_{10}$-aralkyl, SH, S($C_1$-$C_8$-alkylene), $SO_2$ ($C_1$-$C_8$-alkylene) $SO(C_1$-$C_8$alkylene), $NR^{11}R^{12}$, $R^{15}$, a $C_1$-$C_8$-alkyl substituted by $R^{15}$, $R^{16}$, a $C_1$-$C_8$-alkyl substituted by $R^{16}$, $O(C_1$-$C_8$-alkylene)-$NR^{11}C(C=O)O$—$(C_0$-$C_4$-alkylene)-$R^{15}$, cyano, oxo, carboxy, nitro, $C_1$-$C_8$-alkylcarbonyl, hydroxy-$C_1$-$C_8$-alkyl, $C_1$-$C_8$-haloalkyl, amino-$C_1$-$C_8$-alkyl, amino(hydroxy)$C_1$-$C_8$-alkyl and $C_1$-$C_8$-alkoxy optionally substituted by aminocarbonyl, where $R^{15}$ is a $C_6$-$C_{15}$-membered aromatic carbocyclic group, optionally substituted by OH, $C_1$-$C_8$-alkoxy, $C_1$-$C_8$alkyl, halogen and $C_1$-$C_8$-haloalkyl, $R^{16}$ is a 3- to 14-membered heterocyclic group, optionally substituted by OH, $C_1$-$C_8$-alkoxy, $C_1$-$C_8$-alkyl, halogen and $C_1$-$C_8$-haloalkyl, and wherein each alkylene group, unless otherwise specified, is optionally substituted by $C_1$-$C_8$-alkyl, halogen, $C_1$-$C_8$-alkoxy, carboxy, $C_1$-$C_8$-alkyl-carboxy, $C_1$-$C_8$-haloalkyl, $C_1$-$C_8$-haloalkoxy, $C_3$-$C_{15}$-carbocyclic group, $C_1$-$C_8$-alkylcarbonyl, $C_1$-$C_8$-alkoxycarbonyl, nitro, cyano, $R^{15}$, a $C_1$-$C_8$-alkyl substituted by $R^{15}$, $R^{16}$ or a $C_1$-$C_8$-alkyl substituted by $R^{16}$; and $R^{14}$ is selected from H, halogen, $C_1$-$C_8$-alkyl, OH, $C_6$-$C_{15}$-membered aromatic carbocyclic group, $C_7$-$C_{14}$-aralkyl, and O—$C_7$-$C_{14}$-aralkyl.

An aspect of the present invention provides compounds of formula (I), or tautomers, or stereoisomers, or pharmaceutically acceptable salts thereof, wherein M, $M_1$ and $M_2$ are independently

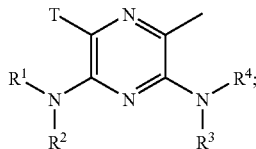

$R^1$, $R^2$, $R^3$, and $R^4$ are independently selected from H, $C_1$-$C_8$-alkyl, $C_1$-$C_8$-alkyl-carboxy;

L, $L_1$ and $L_2$ are independently selected from:

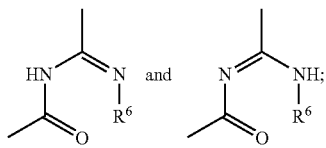

$R^5$, $R^{5a}$ and $R^{5b}$ are independently selected from H, and $C_1$-$C_8$-alkyl, or $R^5$ with the nitrogen atom to which it is attached, together with A, form a 4- to 14-membered heterocyclic group when $X_1$ is $C_0$-$C_8$-alkylene, O, —$NR^7$—, or S, or $R^{5a}$ with the nitrogen atom to which it is attached, together with A, form a 4- to 14-membered heterocyclic group when $X_2$ is $C_0$-$C_6$-alkylene, O, —$NR^7$—, or S, or $R^{5b}$ with the nitrogen atom to which it is attached, together with A, form a 4- to 14-membered heterocyclic group when X is $C_0$-$C_8$-alkylene, O, —$NR^7$—, or S;

$R^6$ is selected from H, and $C_1$-$C_8$-alkyl;

W, $W_1$ and $W_2$ are selected from $C_0$-$C_8$alkylene;

X, $X_1$ and $X_2$ are selected from $C_0$-$C_8$-alkylene, O, S, —$NR^7$—, —$NR^7(C=O)$—, —$NR^7(C=O)NR^8$—, —$NR^8SO_2$—, —$NR^7(SO_2)NR^8$—, —$NR^7(C=O)O$—, —$O(C=O)$—, —$O(C=O)O$—, —$O(C=O)NR^7$—, —$(C=S)NR^7$—, —$(C=NR^7)NR^8$—, —$(C=O)NR^7$—, —$(C=O)O$—, —$(SO_2)(C_0$-$C_8$-alkylene)-, —$(SO_2)NR^8$— and —$(SO_2)NR^7$—Z—$(SO_2)NR^8$—;

Y, $Y_1$ and $Y_2$ are —$C_0$-$C_8$-alkylene-;

Z is $C_1$-$C_4$-alkylene;

where W, $W_1$, $W_2$, Y, $Y_1$, $Y_2$, and Z are optionally substituted by $C_1$-$C_8$-alkyl, halogen, $C_1$-$C_8$-alkoxy, carboxy, $C_1$-$C_8$-alkyl-carboxy, $C_1$-$C_8$-haloalkyl, $C_1$-$C_8$-haloalkoxy, $C_1$-$C_8$-carbocyclic group, $C_1$-$C_8$-alkylcarbonyl, $C_1$-$C_8$-alkoxycarbonyl, nitro, cyano, a $C_6$-$C_{15}$-membered aromatic carbocyclic group, a $C_1$-$C_8$-alkyl substituted by a $C_6$-$C_{15}$-membered aromatic carbocyclic group, a 4- to 14-membered heterocyclic group containing at least one ring heteroatom selected from the group consisting of nitrogen, oxygen and sulphur, a $C_1$-$C_8$-alkyl substituted by a 4- to 14-membered heterocyclic group containing at least one ring heteroatom selected from the group consisting of nitrogen, oxygen and sulphur, and a $C_1$-$C_8$-alkyl substituted by a $C_6$-$C_{15}$-membered aromatic carbocyclic group;

A is selected from a $C_6$-$C_{15}$-membered aromatic carbocyclic group, $C_3$-$C_{15}$-carbocyclic group, a 4- to 14-membered heterocyclic group, a heteroatom selected from nitrogen, oxygen, and sulphur, wherein the nitrogen can be substituted by —Y—X—W—$NR^{5b}$-L-M, a $C_1$-$C_8$-alkyl optionally substituted by —Y—X—W—$NR^{5b}$-L-M, with the proviso that when $R^5$ and $R^{5a}$ does not form a 4- or 14-membered heterocyclic group with A, then A is not a $C_6$-$C_{11}$-aromatic carbocyclic group, O, C=O or a $C_1$-$C_8$-alkyl group when $X_1$, $X_2$, $Y_1$ and $Y_2$ are $C_0$-$C_8$-alkylene unless A is substituted by —Y—X—W—$NR^{5b}$-L-M;

$R^7$, $R^8$, $R^{11}$ and $R^{12}$, are independently selected from H, $C_1$-$C_8$-alkyl optionally substituted by $C_7$-$C_{14}$-aralkyl, $C_1$-$C_8$-haloalkyl, a 5- to 14-membered heterocyclic group, and $R^7$ and $R^8$, independently, by way of an $C_1$-$C_4$-alkyl group can form a bond with a carbon atom of group W or Y creating a 5- to 14-membered heterocyclic group; and T is selected from H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, and a $C_1$-$C_8$-alkyl substituted by a $C_6$-$C_{15}$-membered aromatic carbocyclic group.

In compounds of formula (I), the following meanings are preferred independently, collectively or in any combination:

According to formula (I), L, L$_1$ and L$_2$ are suitably

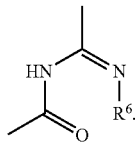

Equally suitably, L, L$_1$ and L$_2$ are

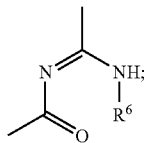

According to formula (I), R$^1$ is preferably H.
According to formula (I), R$^2$ is preferably H.
According to formula (I), R$^3$ is preferably H.
According to formula (I), R$^4$ is preferably H.
M, M$_1$, and M$_2$ are preferably

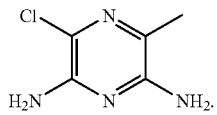

According to formula (I), preferably R$^5$ R$^{5a}$ and R$^{5b}$ are H.
According to formula (I), R$^6$ is preferably H.
According to formula (I), where A is a C$_3$-C$_{15}$-carbocyclic group, this is suitably a 4- to 6-membered carbocyclic group, e.g., cyclobutane and cyclohexane.
According to formula (I), A can be nitrogen substituted by —Y—X—W—NR$^{5b}$-L-M.
According to formula (I), W, W$_1$ and W$_2$ are independently, methylene, ethylene, butylene, pentylene or hexylene, preferably W$_1$ and W$_2$ are methylene.
According to formula (I), X, X$_1$ and X$_2$ are suitably C$_0$-C$_8$-alkylene, —NR$^7$—, NR$^7$(C═O)—, —NR$^7$(C═O)NR$^8$—, —NR$^8$SO$_2$—, —NR$^7$(SO$_2$)NR$^8$—, —NR$^7$(C═O)O—, —O(C═O)—, —(C═O)O—, —O(C═O)NR$^7$—, —(C═S)NR$^7$—, —(C═NR$^7$)NR$^8$—, —(C═O)NR$^7$—, —(C═O)O—, —(SO$_2$)(C$_0$-C$_8$-alkylene)-, —(SO$_2$)NR$^{18}$—, —(SO$_2$)NR$^8$—Z—(SO$_2$)NR$^8$—, or R$^7$ and R$^8$, independently, by way of a C$_1$-C$_4$-alkyl group can form a bond with a carbon atom of group W$_1$ or W$_2$ or Y$_1$ or Y$_2$ to create a 5- to 14-membered heterocyclic group, e.g.,

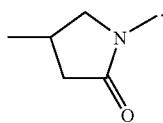

R$^7$ and R$^8$ are preferably, independently H and C$_1$-C$_8$-alkyl.
Preferably X, X$_1$ and X$_2$ are C$_0$-alkylene, i.e., a bond.

According to formula (I), Z is suitably —(C$_0$-C$_2$-alkylene)-. Preferably Z is methylene or ethylene.

According to formula (I), Y, Y$_1$ and Y$_2$ are suitably —(C$_0$-C$_2$-alkylene)-. Preferably Y$_1$ and Y$_2$ are C$_0$, i.e., a bond, methylene or ethylene.

According to formula (I), T is suitably halogen, preferably chlorine.

In a more preferred embodiment, the present invention provides compounds of formula (Ia)

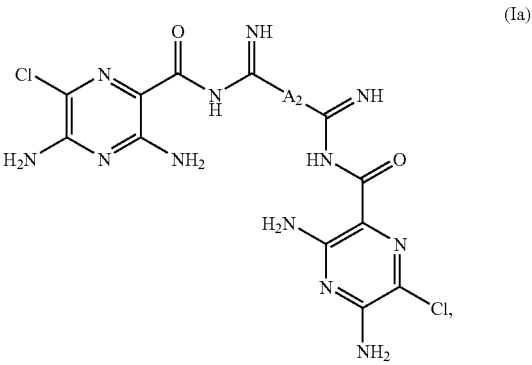

or tautomers, or stereoisomers, or pharmaceutically acceptable salts thereof, wherein A$_2$ is selected from

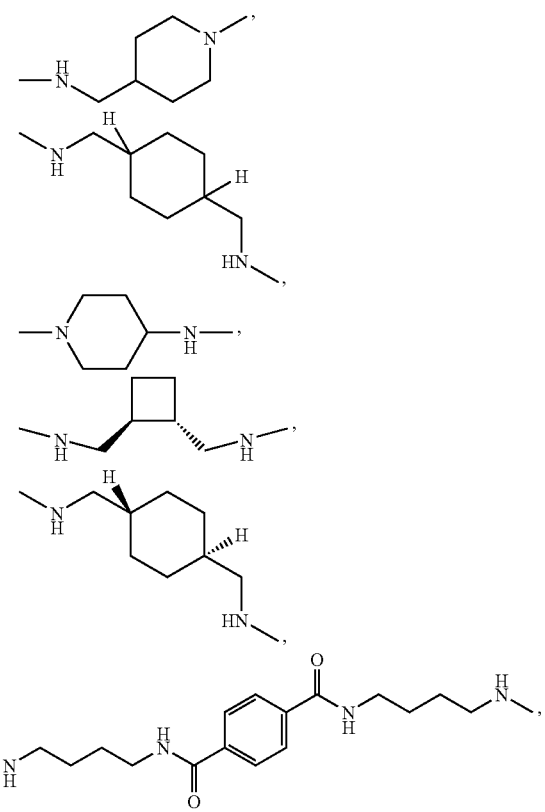

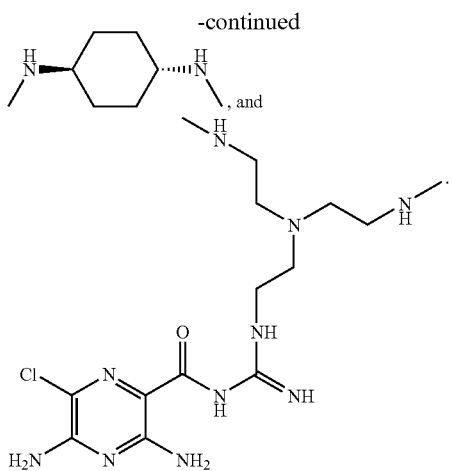

In another embodiment, the present invention provides for the use of a compound of formula (I) in any of the aforementioned embodiments, in free or pharmaceutically acceptable salt form, for the manufacture of a medicament for the treatment of an inflammatory or allergic condition, particularly an inflammatory or obstructive airways disease.

A preferred embodiment of the present invention provides for the use of a compound of formula (I) in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia, and keratoconjunctivitis sire.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Definitions

Terms used in the specification have the following meanings:

"Optionally substituted" means the group referred to can be substituted at one or more positions by any one or any combination of the radicals listed thereafter.

"Halo" or "halogen", as used herein, may be fluorine, chlorine, bromine or iodine.

"$C_1$-$C_8$-Alkyl", as used herein, denotes straight chain or branched alkyl having 1-8 carbon atoms.

"$C_1$-$C_8$-Alkoxy", as used herein, denotes straight chan or branched alkoxy having 1-8 carbon atoms.

The term "alkylene" denotes a straight chain or branched saturated hydrocarbon chain.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_6$-alkyl.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined, attached by a carbon atom to a carbonyl group.

"$C_3$-$C_8$Cycloalkylcarbonyl", as used herein, denotes $C_3$-$C_8$-cycloalkyl, as hereinbefore defined, attached by a carbon atom to a carbonyl group.

"$C_7$-$C_{14}$-Aralkyl", as used herein, denotes alkyl, e.g., $C_1$-$C_4$-alkyl, as hereinbefore defined, substituted by a $C_6$-$C_{10}$-aromatic carbocyclic group, as herein defined.

"$C_3$-$C_{15}$-Carbocyclic group", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl, and bicyclodecyl.

"$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene.

"4- to 14-Membered heterocyclic group" refers to a 4- to 14-membered heterocyclic ring containing at least one ring heteroatom selected from the group consisting of nitrogen, oxygen and sulphur, which may be saturated, partially saturated or unsaturated (aromatic). Examples of 3- to 14-membered heterocyclic groups include but are not limited to furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole or thiazole.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Especially preferred specific compounds of formula (I) are those described hereinafter in the Examples.

The compounds represented by formula (I) may be capable of forming acid addition salts, particularly pharmaceutically acceptable acid addition salts. Pharmaceutically acceptable acid addition salts of the compound of formula (I) include those of inorganic acids, e.g., hydrohalic acids, such as hydrofluoric acid, hydrochloric acid, hydrobromic acid or hydroiodic acid, nitric acid, sulfuric acid, phosphoric acid; and organic acids, e.g., aliphatic monocarboxylic acids, such as formic acid, acetic acid, trifluoroacetic acid, propionic acid and butyric acid; aliphatic hydroxy acids, such as lactic acid, citric acid, tartaric acid or malic acid; dicarboxylic acids, such as maleic acid or succinic acid; aromatic carboxylic acids, such as benzoic acid, p-chlorobenzoic acid, diphenylacetic acid, para-biphenyl benzoic acid or triphenylacetic acid; aromatic hydroxy acids, such as o-hydroxybenzoic acid, p-hydroxybenzoic acid, 1-hydroxynaphthalene-2-carboxylic acid or 3-hydroxynaphthalene-2-carboxylic acid; cinnamic acids, such as 3-(2-naphthalenyl)propenoic acid, para-methoxy cinnamic acid or para-methyl cinnamic acid; and sulfonic acids, such as methanesulfonic acid or benzenesulfonic acid. These salts may be prepared from compounds of formula (I) by known salt-forming procedures.

Compounds of formula (I) which may contain acidic, e.g., carboxyl, groups, are also capable of forming salts with bases, in particular, pharmaceutically acceptable bases, such as those well-known in the art; suitable such salts include metal salts, particularly alkali metal or alkaline earth metal salts, such as sodium, potassium, magnesium or calcium salts; or salts with ammonia or pharmaceutically acceptable organic amines or heterocyclic bases, such as ethanolamines, benzylamines or pyridine. These salts may be prepared from compounds of formula (I) by known salt-forming procedures.

Stereoisomers are those compounds where there is an asymmetric carbon atom. The compounds exist in individual optically active isomeric forms or as mixtures thereof, e.g., as diastereomeric mixtures. The present invention embraces both individual optically active R and S isomers, as well as mixtures thereof. Individual isomers can be separated by methods well known to those skilled in the art, e.g. chiral high performance liquid chromatography (HPLC).

Tautomers are one of two or more structural isomers that exist in equilibrium and are readily converted from one isomeric form to another.

The compounds of the invention may exist in both unsolvated and solvated forms. The term "solvate" is used herein to describe a molecular complex comprising the compound of the invention and one or more pharmaceutically acceptable solvent molecules, e.g., ethanol. The term "hydrate" is employed when said solvent is water.

Synthesis

An embodiment of the present invention provides a process for the preparation of compounds of formula (I):

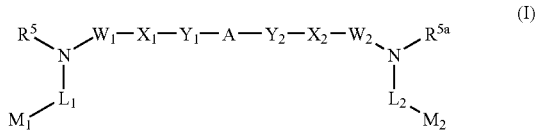

or tautomers, or stereoisomers, or pharmaceutically acceptable salts thereof, wherein
$M_1, M_2, L_1, L_2, NR^5, NR^{5a}, W_1, W_2, X_1, X_2, Y_1, Y_2$, and A are as defined hereinbefore, which comprises the steps of:
(i) reacting a compound of formula (IV)

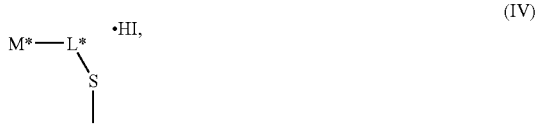

wherein
M* is $M_1$ or $M_2$;
L* is $L_1$ or $L_2$; and
$M_1, M_2, L_1, L_2$ and T are as hereinbefore defined,
with compounds of formula (V):

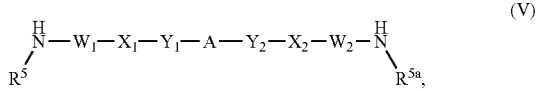

wherein $R^5, R^{5a}, W_1, W_2, X_1, X_2, Y_1, Y_2$ and A are hereinbefore defined,
optionally in the presence of a base, e.g., an organic base; and in an organic solvent e.g., a non-protic dipolar solvent; and
(ii) recovering the resultant compound of formula (I), in free or pharmaceutically acceptable salt form.

The compounds of formula (I) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practioner is Greene and Wuts, *Protective Groups in Organic Synthesis*, Wiley and Sons (1999).

Generally, compounds described in the scope of this patent application can be synthesized by the routes described in Scheme 1 and Scheme 2 and the Examples.

In Scheme 1, compounds of formula (I) can be prepared according to the processes described by Cragoe et al., *J Med Chem*, Vol. 10, pp. 66-73 (1967); and European Patent EP 0 017 152 and U.S. Pat. No. 3,544,571. For instance, intermediate 1 can be reacted with intermediate 2, where A is as defined hereinbefore, in the presence of triethylamine in organic solvent to provide compound 3 as the free base. The free base can then be converted to a salt form by treatment with an appropriate acid. Intermediates can be prepared from methods known by those skilled in the art or are commercially-available.

organic solvent to provide Intermediate 3. Subsequent deprotection of Intermediate 3 using conventional deprotection techniques affords Intermediate 4. Intermediate 4 may be reacted with $M_2$-J where $M_2$ is hereinbefore defined to provide compound 5. P represents a standard amine protecting group, e.g., Boc, CBz, acetate, and deprotection is by standard means. J represents a group capable of reacting with amines, e.g., halogen, thioether, carboxylic acid, isocyanate, sulfonyl chlorides, aldehydes and ketones.

Scheme 1

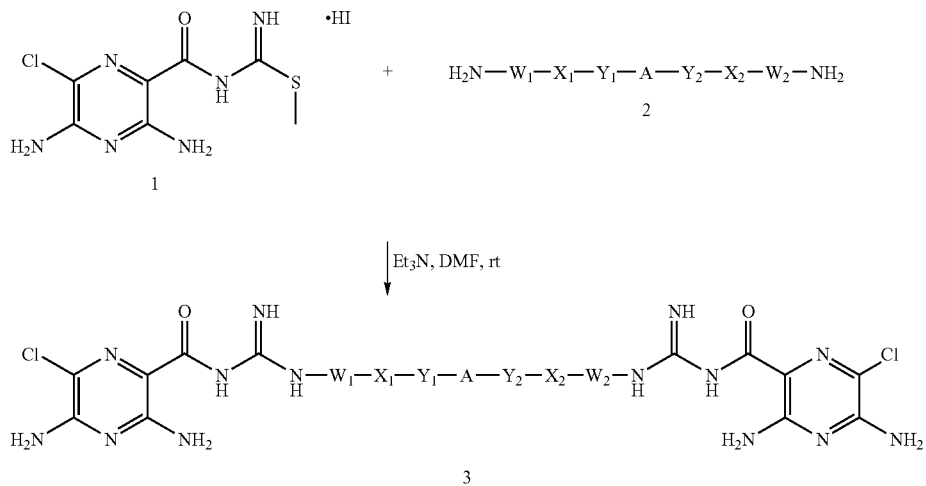

Compounds of formula (I) can also be prepared according to Scheme 2 by reacting Intermediate 1 with a mono protected diamine (Intermediate 2) in the presence of triethylamine in Scheme 2

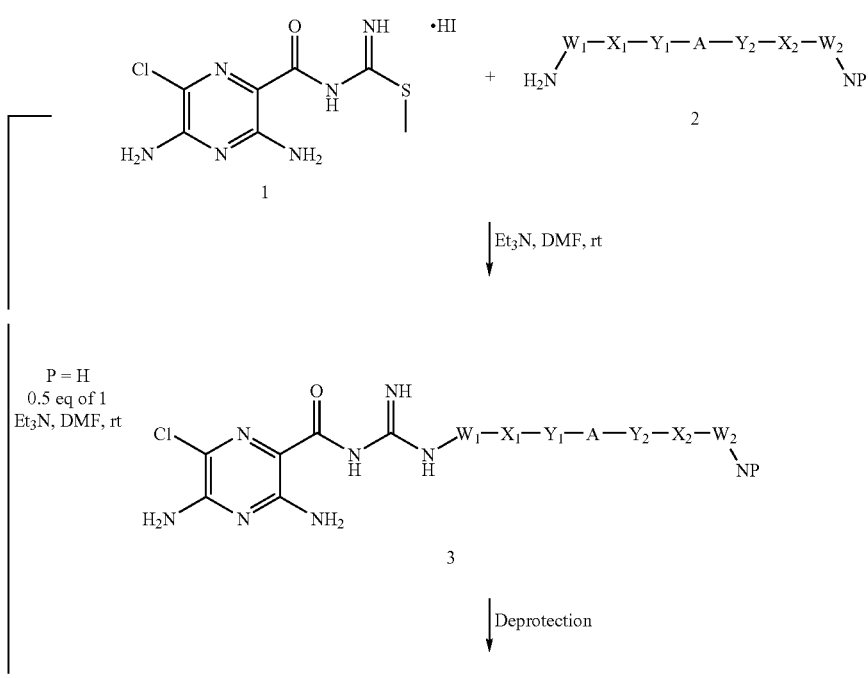

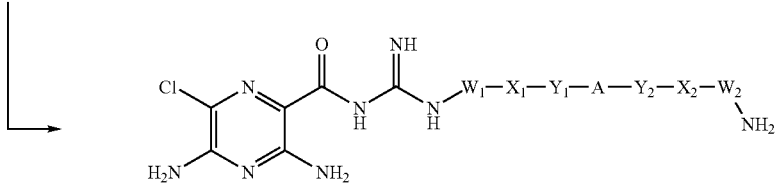

4

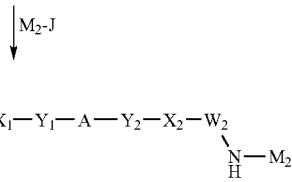

5

Compounds of formula (I), in free form, may be converted into salt form, and vice versa, in a conventional manners understood by those skilled in the art. The compounds in free or salt form can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

Pharmacological Activity

Having regard to their blockade of the epithelial sodium channel (ENaC), compounds of formula (I), in free or pharmaceutically acceptable salt form, hereinafter alternately referred to as "agents of the invention", are useful in the treatment of conditions which respond to the blockade of the epithelial sodium channel, particularly conditions benefiting from mucosal hydration.

Diseases mediated by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Treatment in accordance with the invention may be symptomatic or prophylactic.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

The suitability of epithelial sodium channel blocker as a treatment of a disease benefiting from mucosal hydration, may be tested by determining the inhibitory effect of the channel activating protease inhibitor on: the ion channel/ion transport function in suitable isolated cells or confluent epithelia using the methods described in Bridges et al., Am J Physiol Lung Cell Mol Physiol, Vol. 281, No. 1, pp. L16-23 (2001); and Donaldson et al., J Biol Chem, Vol. 277, No. 10, pp. 8338-8345 (2002).

Epithelial sodium channel blockers, including the compounds of formula (I), are also useful as co-therapeutic agents for use in combination with other drug substances, such as anti-inflammatory, bronchodilatory, antihistamine or anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

The epithelial sodium channel blocker may be mixed with the other drug substance in a fixed pharmaceutical composition or it may be administered separately, before, simultaneously with or after the other drug substance.

Accordingly, the invention includes a combination of epithelial sodium channel blocker with an antiinflammatory, bronchodilatory, antihistamine, anti-tussive, antibiotic or DNase drug substance, said epithelial sodium channel blocker and said drug substance being in the same or different pharmaceutical composition.

Suitable antibiotics include macrolide antibiotics, e.g., tobramycin (TOBI™)

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl phenyl)-5H-benzo-cyclohepten-8-yl]carbonyl]amino]phenyl]-methyl] tetrahydro-N,N-dimethyl-2H-pyran-4-aminium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID (TM) CC-10004 (Ceigene), VM554/UM565 (Vemalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula

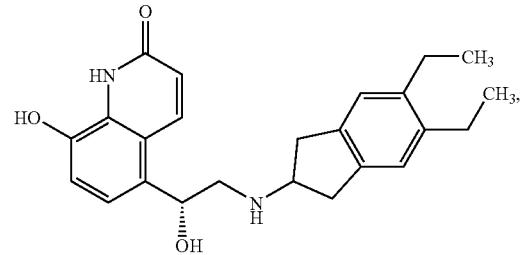

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. Nos. 3,714,357, 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Other useful combinations of agents of the invention with anti-inflammatory drugs are those with antagonists of chemokine receptors, e.g., CCR-1, CCR-2, CCR-3, CCR4, CCR-5, CCR-6, CCR-7, CCR8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methylphenyl)-5H-benzo-cyclohepten 8-yl]carbonyl]amino]phenyl]-methyl]tetrahydro-N,N-dimethyl-2H-pyran-4--amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition responsive to blockade of the epithelial sodium channel, e.g., diseases associated with the regulation of fluid volumes across epithelial membranes, particularly an obstructive airways disease, which comprises administering to a subject, particularly a human subject, in need thereof a compound of formula (I), in free form or in the form of a pharmaceutically acceptable salt. In another aspect the invention provides a compound of formula (I), in free form or in the form of a pharmaceutically acceptable salt, for use in the manufacture of a medicament for the treatment of a condition responsive to blockade of the epithelial sodium channel, particularly an obstructive airways disease, e.g., Cystic Fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

The invention includes:
(a) a compound of formula (I) in inhalable form, e.g., in an aerosol or other atomisable composition or in inhalable particulate, e.g., micronised form;
(b) an inhalable medicament comprising a compound of formula (I) in inhalable form;
(c) a pharmaceutical product comprising a compound of formula (I) in inhalable form in association with an inhalation device; and
(d) an inhalation device containing a compound of formula I in inhalable form.

Dosages of compounds of formula (I) employed in practising the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I) and their pharmaceutically acceptable salts, hereinafter referred to alternatively as "agents of the invention", are useful as pharmaceuticals. In particular, the compounds have good ENaC blocker activity and may be tested in the following assays.

Cell Culture

Human Bronchial Epithelial cells (HBECS) (Cambrex) were cultured under air-liquid interface conditions to provide a well differentiated mucociliary phenotype.

HBECs were cultured using a modification of the method described by Gray and colleagues (Gray et al., 1996). Cells were seeded in plastic T-162 flasks and were grown in bronchial epithelial cell growth medium (BEGM; Cambrex) supplemented with bovine pituitary extract (52 µg/mL), hydrocortisone (0.5 µg/mL), human recombinant epidermal growth factor (0.5 ng/mL), epinephrine (0.5 µg/mL), transferrin (10 µg/mL), insulin (5 µg/mL), retinoic acid (0.1 µg/mL), triiodothyronine (6.5 µg/mL), gentamycin (50 µg/mL) and amphotericin B (50 ng/mL). Medium was changed every 48 hours until cells were 90% confluent. Cells were then passaged and seeded ($8.25 \times 10^5$ cells/insert) on polycarbonate Snapwell inserts (Costar) in differentiation media containing 50% DMEM in BEGM with the same supplements as above but without triiodothyronine and a final retinoic acid concentration of 50 nM (all-trans retinoic acid). Cells were maintained submerged for the first 7 days in culture, after which time they were exposed to an apical air interface for the remainder of the culture period. At this time, media was changed to DMEM:F12 media containing 2% v/v Ultroser G for the remainder of culture. Amphotericin B was removed from all media 3 feeds prior to use in the Ussing Chambers. Cells were used between days 7 and 21 after establishment of the apical-air interface. At all stages of culture, cells were maintained at 37° C. in 5% $CO_2$ in an air incubator.

Short Circuit Current (ISC) Measurements

Snapwell inserts were mounted in Vertical Diffusion Chambers (Costar) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$, and 10 glucose. The solution osmolarity was between 280 and 300 mOsmol/kg $H_2O$ for all physiological salt solutions used. Cells were voltage clamped to 0 mV (model EVC4000; WPI). RT was measured by applying a 1- or 2-mV pulse at 30-s intervals and calculating RT by Ohm's law. Data were recorded using a PowerLab workstation (ADInstruments).

Test compounds were prepared as a 10 mM stock solution in DMSO (95%). Serial 3-fold dilutions were freshly prepared in an appropriate vehicle (distilled $H_2O$ or Ringers solution). The initial concentration was added to the apical chamber as a 1000× concentrate in 5 µL, resulting in a final 1× concentration the 5 mL volume of the Ussing chamber. Subsequent additions of compound were added in a 3.3 µL volume of the 1000× serially diluted stock solution. At the completion of the concentration-response experiment, amiloride (10 µM) was added into the apical chamber to enable the total amiloride-sensitive current to be measured. An amiloride control $IC_{50}$ was established at the start of each experiment.

Results are expressed as the mean % inhibition of the amiloride-sensitive ISC. Concentration-response curves were plotted and $IC_{50}$ values generated using GraphPad Prism 3.02. Cell inserts were typically run in duplicate and the $IC_{50}$ calculated on the mean % inhibition data.

Compounds of the Examples, herein below, generally have $IC_{50}$ values in the data measurements described above below 10 μM. For example, the compounds of Examples 2, and 5 have $IC_{50}$ values of 0.0057 and 0.0002 μM, respectively.

The invention is illustrated by the following Examples.

EXAMPLES

General Conditions

LCMS are recorded on an Agilent 1100 LC system with a Waters Xterra MS C18 4.6×100 5 μM column, eluting with 5-95% 10 mM aqueous ammonium bicarbonate in acetonitrile over 2.5 minutes, with negative ion electrospray ionization or 5-95% water+0.1% TFA in acetonitrile with positive ion electrospray ionization. [M+H]+ and [M−H]− refer to monoisotopic molecular weights DMF dimethylformamide
DMSO dimethyl sulfoxide
$Et_3N$ triethylamine
EtOAc ethyl acetate
HPLC high performance liquid chromatography
MeOH methanol
RT room temperature
TFA trifluoroacetic acid
HATU O-(7-azabenzotriazol-1-yl)-N,N,-N',N'-tetramethyl-uronium hexafluorophophate The following examples have been prepared using the process described herein.

TABLE 1

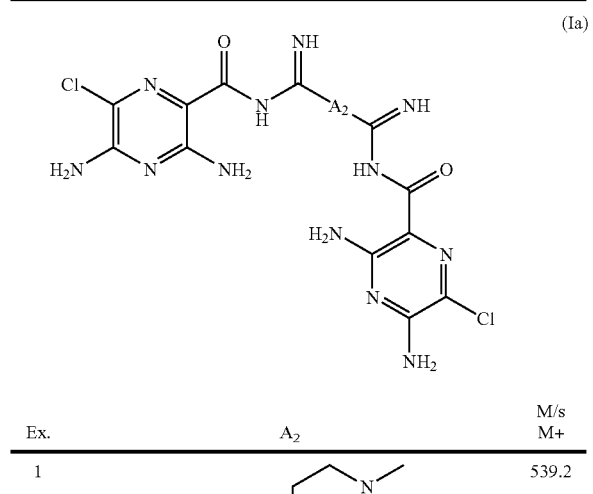

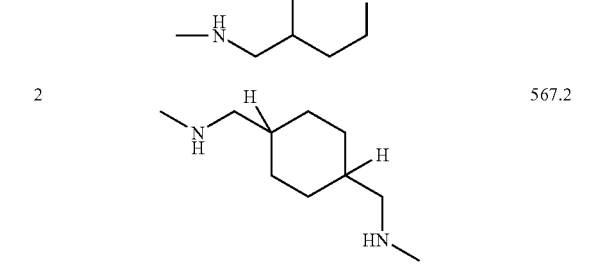

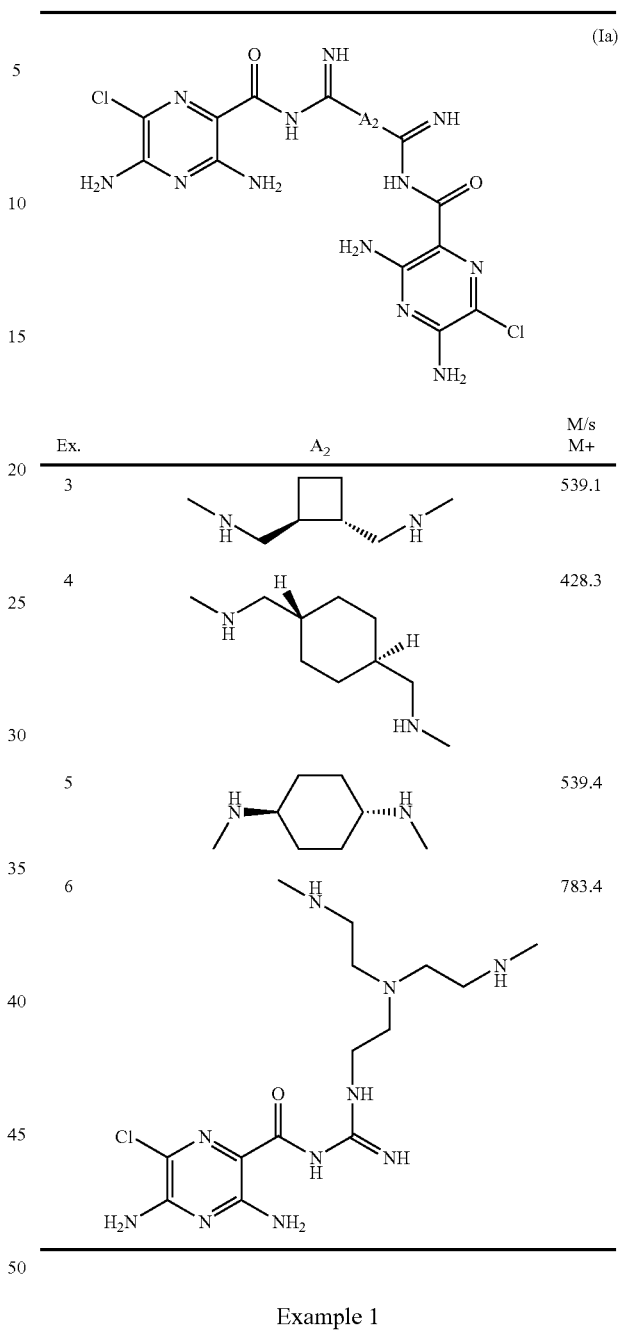

Example 1

3,5-Diamino-chloro-pyrazine-2-carboxylic acid ({4-[N'-3,5-diamino-6-chloro-pyrazine-2-carbonyl)-guanidinomethyl]-piperidin-1-yl}-imino-methyl)-amide To a solution of 1-(3,5diamino-6-chloropyrazinoyl)-2-methyl-2-thioseudourea (II) (100 mg, 0.26 mmol) dissolved in DMF (1 mL) is added 4-aminomethyl piperidine (14.8 mg, 0.13 mmol) and $Et_3N$ (146 μL, 1.04 mmol). Stirring is continued at RT for 18 hours. The product is purified by reverse phase column chromatography (0-100% acetonitrile gradient over 20 minutes and 0.05% TFA modifier in both aqueous and organic phases) to give the title product as the trifluoroacetate salt.

Examples 2-5 are Prepared Analogously Using the Appropriate Starting Compounds as Example 1

Example 6

N-[2-(Bis-{2-[N'-(3,5-diamino-6-chloro-pyrazine-2-carbonyl)-guanidino]-ethyl}-amino)-ethyl]-N'-(3,5-diamino-6-chloro-pyrazine-2-carbonyl)-guanidine To a solution of 1-(3,5-diamino-6-chloropyrazinoyl)-2-methyl-2-thioseudourea (II) (1 g, 2.58 mmol) dissolved in DMF (5 mL) is added tris(2-aminoethyl)amine (125.8 mg, 0.86 mmol) and Et$_3$N (386 μL, 1.04 mmol). Stirring is continued at RT for 18 hours. The reaction is filtered in vacuo and the filtrate concentrated and the product is purified by reverse phase column chromatography (0-100% acetonitrile gradient over 20 minutes) to give the title product as the free base.

Further preferred compounds of formula (Ia) and are as shown in Table 2 below. The method of preparation being described thereinafter.

TABLE 2

| Ex. | Structure | M/s [M + H]$^+$ |
|---|---|---|
| 7 | 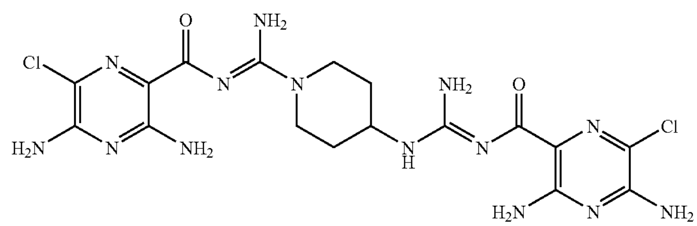 | 525.28 |
| 8 | 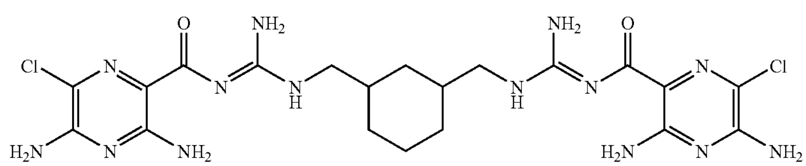 | 567.33 |
| 9 | 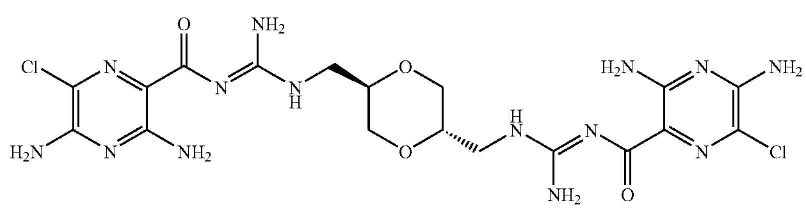 | 571.35 |
| 10 | 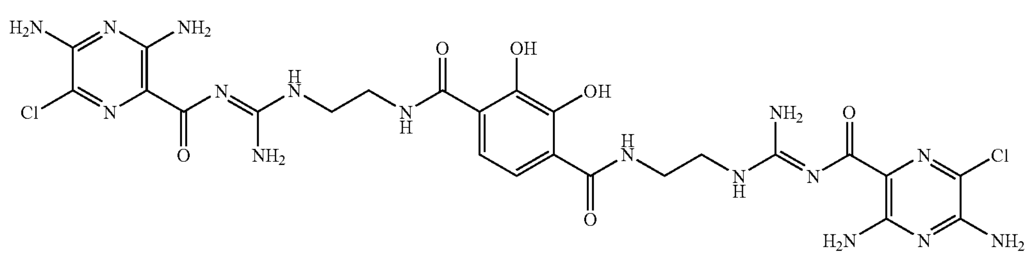 | 707.30 |

TABLE 2-continued (Ia)

| Ex. | Structure | M/s [M + H]+ |
|---|---|---|
| 11 | 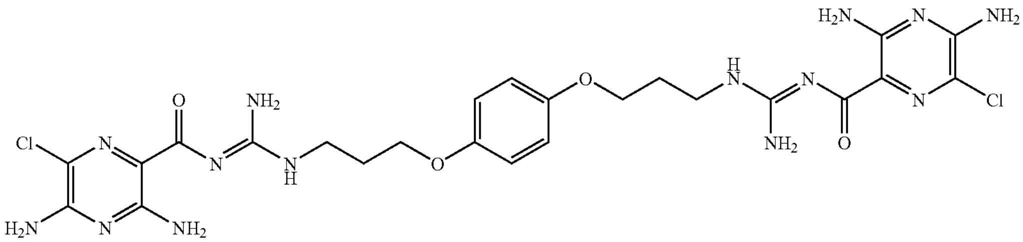 | 649.36 |
| 12 | 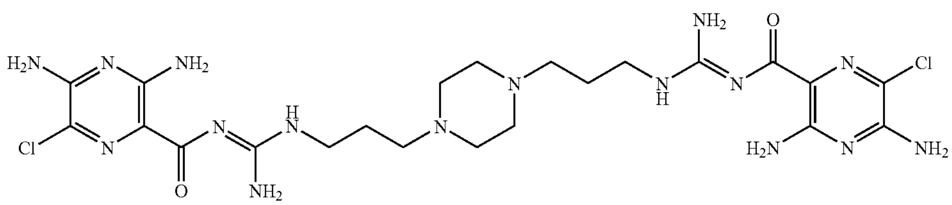 | 625.38 |
| 13 | 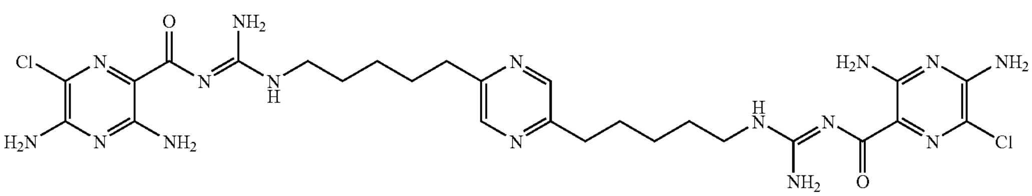 | 675.42 |
| 14 | 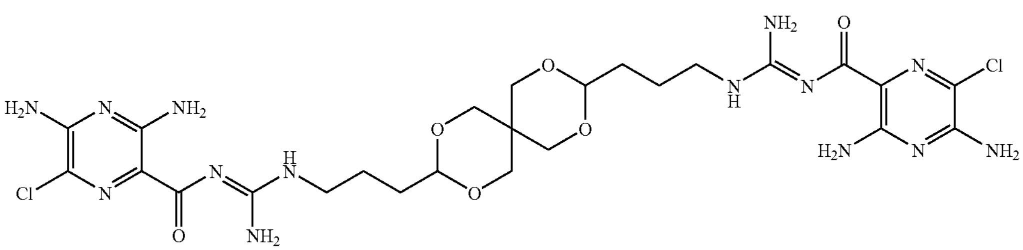 | 699.42 |
| 15 | 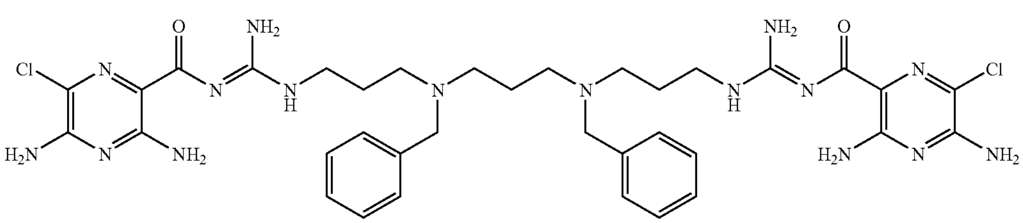 | 793.49 |

TABLE 2-continued
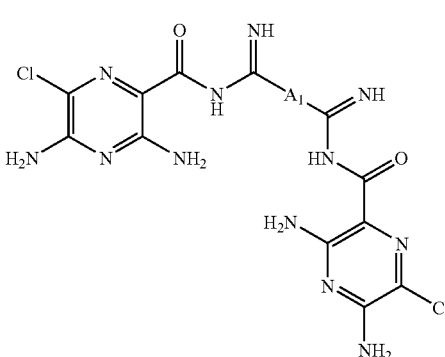
(Ia)
| Ex. | Structure | M/s [M + H]+ |
|---|---|---|
| 16 | 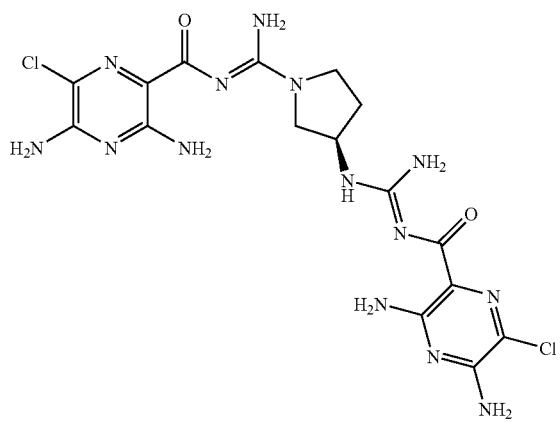 | 511.31 |
| 17 | 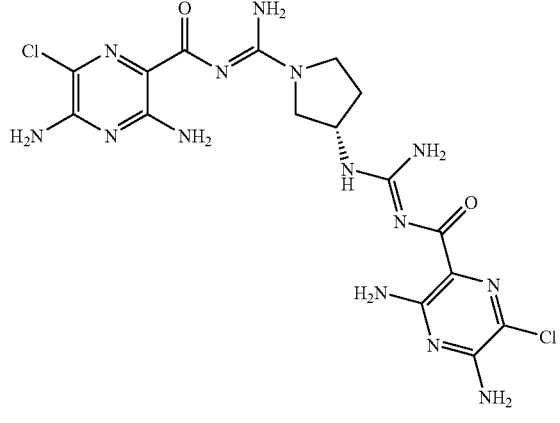 | 511.35 |
| 18 | 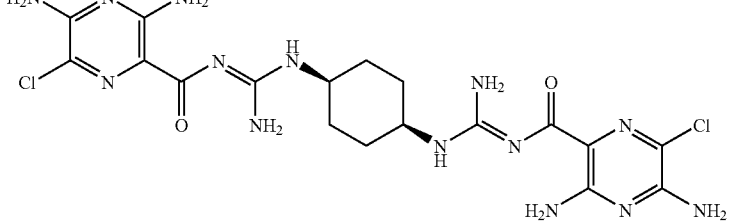 | 539.37 |

TABLE 2-continued
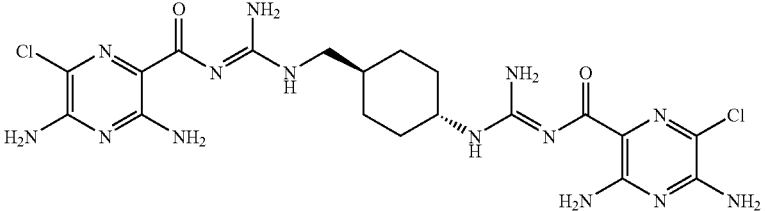
(Ia)
| Ex. | Structure | M/s [M + H]+ |
|---|---|---|
| 19 | 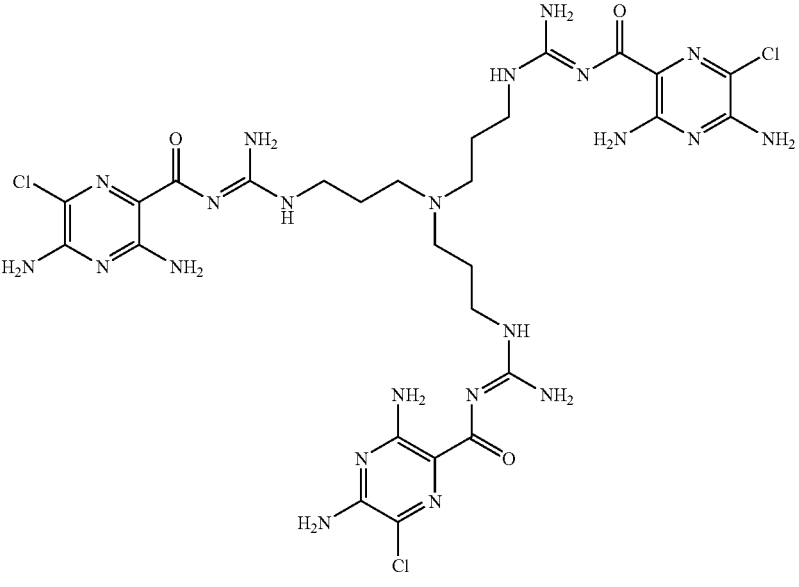 | 553.34 |
| 20 | 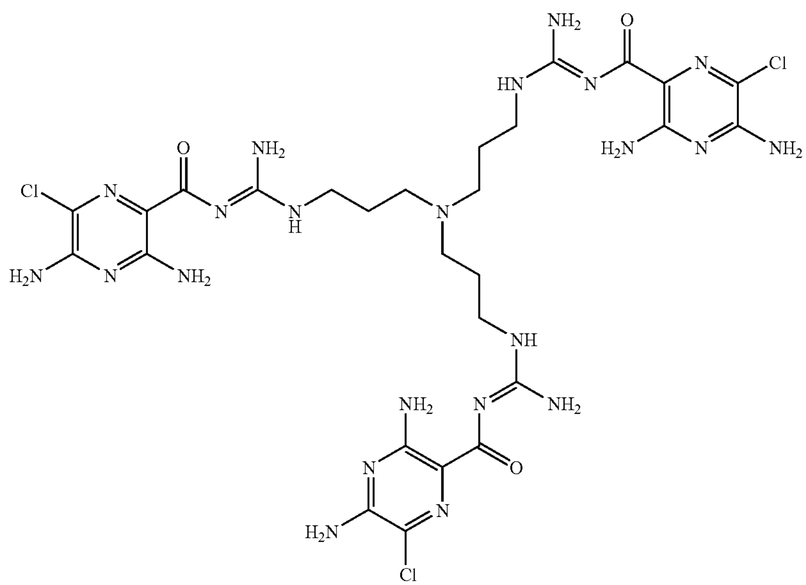 | 825 |
| 21 | 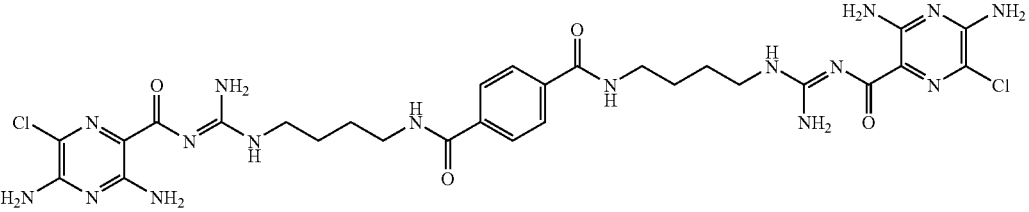 | 731.29 |

TABLE 2-continued (Ia)

| Ex. | Structure | M/s [M + H]+ |
|---|---|---|
| 22 | 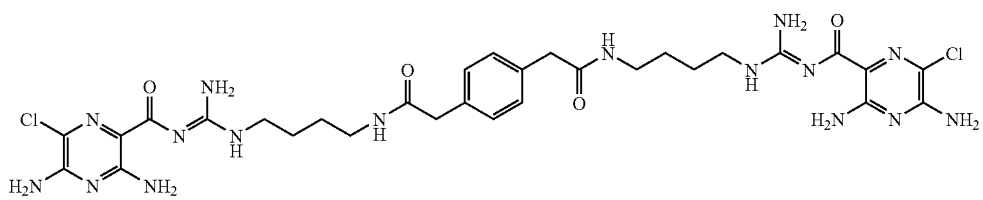 | 759.56 |
| 23 | 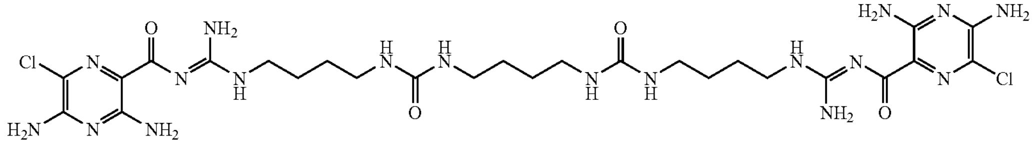 | 741.34 |
| 24 | 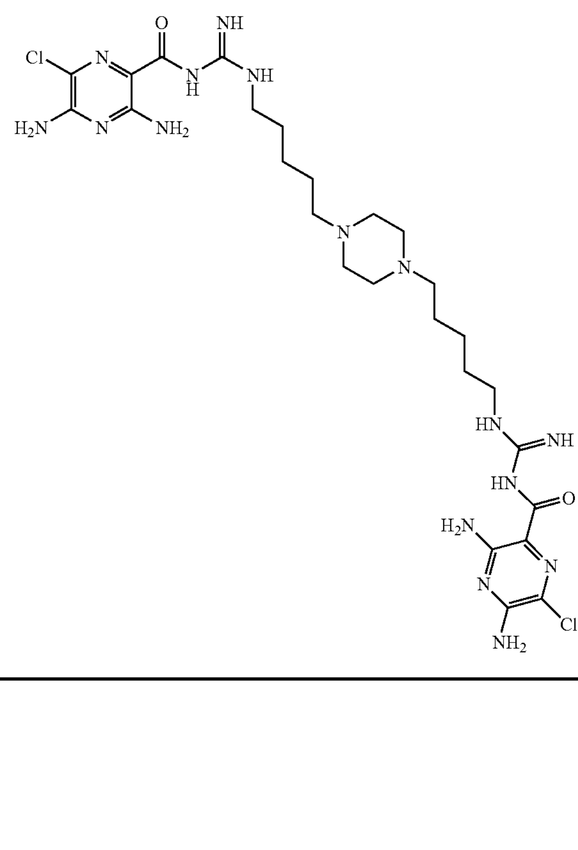 | 680.97 |

Example 7

3,5-Diamino-6-chloro-pyrazine-2-carboxylic acid 1-amino-1-{4-[N'-(3,5-diamino-6-chloro-pyrazine-2-carbonyl)-guanidino]-piperidin-1-yl}-meth-(E)-ylideneamide trifluoroacetate

Step 1

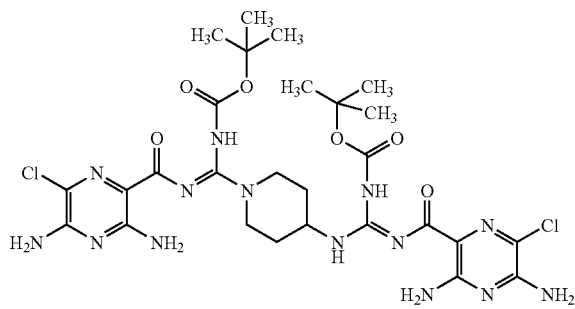

Piperidin 4-ylamine (5.0 mg, 0.05 mmol) is treated with a solution of Intermediate A (0.06 g, 0.16 mmol) in DMF (1.0 mL) followed by Et$_3$N (25.3 mg, 0.25 mmol) and the reaction mixture is stirred at RT overnight. Aminomethylpolystyrene and macroporous isocyanate (scavenger resins) are added and the mixture is allowed to shake at RT overnight. The mixtures are filtered and concentrated in vacuo to afford the product.

Step 2: 3,5-Diamino-6-chloro-pyrazine-2-carboxylic acid 1-amino-1-{4-[N'-(3,5-diamino-6-chloro-pyrazine-2-carbonyl)-guanidino]-piperidin-1-yl}-meth-(E)-ylideneamide trifluoroacetate Example 7, Step 1 (0.05 mmol) is treated with 10% TFA in DCM (0.9 mL) and allowed to stand at RT for 1 hour. The solvent is removed in vacuo and purification of the crude product by preparative HPLC eluting with 10-100% MeCN in water (0.1% TFA) affords the title compound.

Examples 8-15

These examples namely,

N-(3,5-Diamino-6-chloro-pyrazine-2-carbonyl)N'-{3-[N'-(3,5-diamino-6-chloro-pyrazine-2-carbonyl)guanidinomethyl]-cyclohexylmethyl}guanidine trifluoroacetate (Example 8), N-(3,5-Diamino-6-chloro-pyrazine-2-carbonyl)-N'-{(2R,5S)-5-[N'-(3,5-diamino-6-chloro-pyrazine-2-carbonyl)guanidinomethyl]-[1,4]dioxan-2-ylmethyl}-guanidine trifluoroacetate (Example 9), N,N'-Bis-{2-[N'-(3,5-diamino-6-chloro-pyrazine-2-carbonyl)guanidino]-ethyl}-2,3-dihydroxy-terephthalamide trifluoroacetate (Example 10), N-(3,5-Diamino-6-chloro-pyrazine-2-carbonyl)-N'-[3-(4-{3-[N'-(3,5-diamino-6-chloro-pyrazine-2-carbonyl)-guanidino]-propoxy}-phenoxy)-propyl]-guanidine trifluoroacetate (Example 11), N-(3,5-Diamino-6-chloro-pyrazine-2-carbonyl)-N'-[3-(4-{3-[N'(3,5-diamino-6-chloro-pyrazine-2-carbonyl)-guanidino]-propyl}-piperazin-1-yl)-propyl]guanidine trifluoroacetate (Example 12), N-(3,5-Diamino-6-chloro-pyrazine-2-carbonyl)-N'-[5-(5-{5-[N'-(3,5-diamino-6-chloro-pyrazine-2-carbonyl)-guanidino]-pentyl}-pyrazin-2-yl)-pentyl]guanidine trifluoroacetate (Example 13), N-(3,5-Diamino-6-chloro-pyrazine-2-carbonyl)-N'-[3-(9-{3-[N'-(3,5-diamino-6-chloro-pyrazine-2-carbonyl)-guanidino]-propyl}-2,4,8,10-tetraoxa-spiro[5.5]undec-3-yl)-propyl]-guanidine trifluoroacetate (Example 14) and N-(3-{Benzyl-[3-(benzyl-{3-[N'-(3,5-diamino-6-chloro-pyrazine-2-carbonyl)-guanidino]-propyl}-amino)-propyl]-amino}-propyl)-N'-(3,5-diamino-6-chloro-pyrazine-2-carbonyl)-guanidine trifluoroacetate (Example 15), are prepared analogously to Example 7 with the appropriate diamine.

Examples 16-19

These compounds namely, 3,5-Diamino-6-chloro-pyrazine-2-carboxylic acid 1-amino-1-{(R)-3-[N'-(3,5-diamino-6-chloro-pyrazine-2-carbonyl)-guanidino]-pyrrolidin-1-yl}-meth-(E)-ylideneamide trifluoroacetate (Example 16), 3,5-Diamino-6-chloro-pyrazine-2-carboxylic acid 1-amino-1-{(S)-3-[N'-(3,5-diamino-6-chloro-pyrazine-2-carbonyl)-guanidino]-pyrrolidin-1-yl}-meth-(E)-ylideneamide trifluoroacetate (Example 17), N-(3,5-Diamino-6-chloro-pyrazine-2-carbonyl)-N-'-{4-[N'-(3,5-diamino-6-chloro-pyrazine-2-carbonyl)-guanidino]-cyclohexyl}-guanidine trifluoroacetate (Example 18) and N-(3,5-Diamino-6-chloro-pyrazine-2-carbonyl)-N'-{4-[N'-(3,5-diamino-6-chloro-pyrazine-2-carbonyl)-guanidinomethyl]-cyclohexyl}-guanidine trifluoroacetate (Example 19), are prepared analogously to Example 7 with the appropriate diamine with the exception that mercury dichloride (2 eq) in DMF is added to the reaction mixture. Reaction byproducts are removed during purification by addition of scavenger resins, such as aminomethylpolystyrene, macroporous isocyanate and solid supported silica 1-propanethiol.

Example 20

N-[3-(Bis-{3-[N'-3,5-diamino-6-chloro-pyrazine-2-carbonyl)-guanidino]-propyl}-amino)-propyl]N'-(3,5-diamino-6-chloro-pyrazine-2-carbonyl)-guanidine trifluoroacetate This compound is prepared from Intermediate A (3 eq) analogously to Example 7 by replacing piperidin-4-ylamine with tris(2-aminoethyl)amine.

Example 21

N,N'-Bis-{4-[N'-(3,5-diamino-6-chloro-pyrazine-2-carbonyl)-guanidino]-butyl}terephthalamide bromide This compound is prepared analogously to Example 1 by replacing 1-(3,5-diamino-6-chloro-pyrazine-2-carbonyl)-2-methyl-isothiourea hydroiodide with Intermediate A. The boc-protected intermediate that is formed is deprotected using 33% HBr in acetic acid. Reaction by-products are removed during purification by addition of scavenger resins such as aminomethylpolystyrene and macroporous isocyanate.

Example 22

N-{4-[N'-(3,5-Diamino-6-chloro-pyrazine-2-carbonyl)-guanidino]-butyl}-2-[4-({4-[N'-(3,5-diamino-6-chloro-pyrazine-2-carbonyl)-guanidino]-butylcarbamoyl}-methyl)-phenyl]-acetamide trifluoroacetate Step 1: Preparation of Following Compound

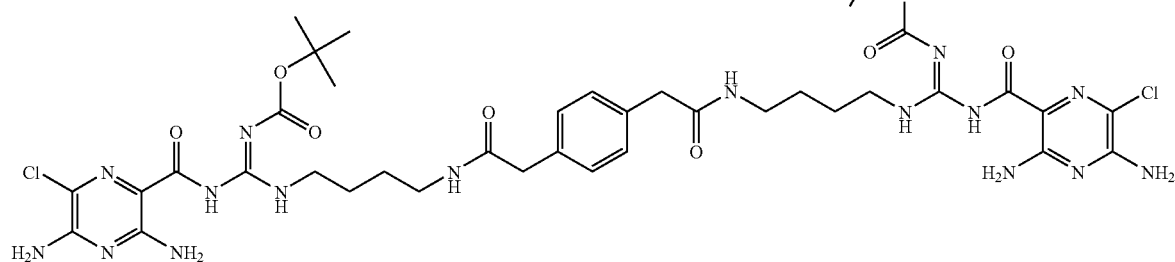

A solution of 1,4-phenylenediacetic acid (24 mg, 0.125 mmol) in DMF (0.75 mL) and Et$_3$N (0.2 mL) is treated with HATU (95 mg, 0.25 mmol) and stirred at RT for 30 minutes. To this mixture is added Intermediate B (0.1 g, 0.25 mmol) and stirring continued for a further 30 minutes. The reaction mixture is passed through a 1 g AL-B Solid Phase Extraction cartridge, eluting with DMF (1.5 mL). The solvent is removed in vacuo and recrystallisation of the crude residue from MeOH affords the product. [M+H]$^+$ 959.74.

Step 2: N-{4-[N'-(3,5-Diamino 6-chloro-pyrazine-2-carbonyl)-guanidino]-butyl}-2-[4-({4-[N'-(3,5-diamino-6-chloro-pyrazine-2-carbonyl)-guanidino]-butylcarbamoyl}-methyl)-phenyl]-acetamide trifluoroacetate Example 22, Step 1 (20 mg, 0.021 mmol) is treated with 10% TFA in DCM (2 mL) and allowed to stand at RT overnight. The solvent is removed in vacuo and purification of the crude product by preparative HPLC eluting with 10-100% MeCN in water (0.1% TFA) affords the title compound.

Example 23

1-{4-[N'-(3,5-Diamino-6-chloro-pyrazine-2-carbonyl)-guanidino]-butyl}-3-[4-(3-{4-[N'-(3,5-diamino-6-chloro-pyrazine-2-carbonyl)-guanidino]-butyl}-ureido)-butyl]-urea A solution of Intermediate B (0.1 g, 0.25 mmol) in DMF (1 mL) is treated with 1,4-diisocyanatobutane (17.5 mg, 0.125 mmol) and stirred at RT over night. The reaction mixture is treated with 0.1 g aminomethylpolystyrene and (0.1 g) macroporous isocyanate (scavenger resins) and stirred at RT for 3 days. The mixture is filtered and purification by preparative HPLC affords the title compound. [M+H]$^+$ 741.34

Example 24

N-(3,5-Diamino-6-chloro-pyrazine-2-carbonyl)-N'-[5-(4-{5-[N'-(3,5-diamino-6-chloro-pyrazine-2-carbonyl)-guanidino]-pentyl}-piperazin-1-yl)-pentyl]-guanidine 5-[4-(5-Amino-pentyl)-piperazin-1-yl]pentylamine trifluoroacetate (Intermediate P) (172 mg, 0.24 mmol) is added to a stirring solution of 1-(3,5-diamino-6-chloro-pyrazine-2-carbonyl)-2-methyl-isothiourea hydroiodide (93 mg, 0.48 mmol) in DMF (1 mL). The resulting mixture is heated to 50° C. for 8 hours and then allowed to cool to RT. The reaction mixture is quenched with 5% citric acid solution and addition of DCM results in the formation of a gum. The gum is isolated and dissolved in MeOH (2 mL). The solution is passed through a "capture release" SCX-2 cartridge eluting with 1 N ammonia in MeOH followed by 1:1 MeOH:ammonia solution to afford the title compound.

Yet further preferred compounds of the present invention include compounds of formula (Ib) and are as shown in Table 3 below. The method of preparation being described thereinafter.

TABLE 3
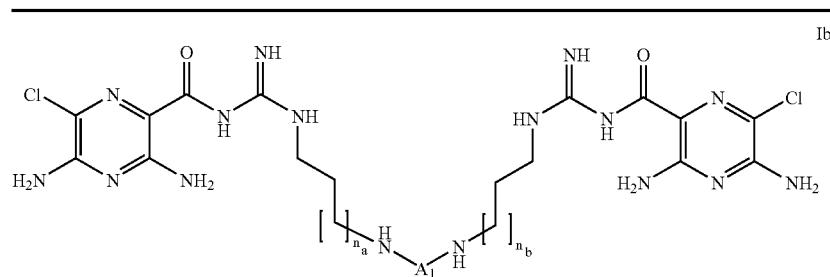
$n_a$ and $n_b$ are independantly = 1-3
| Ex. | A₁ | Viable Preparation Routes | $n_a$ | $n_b$ |
|---|---|---|---|---|
| 25 | (1,2-diacetylbenzene) | 1 or 2 or 8a or 8b | 1 | 1 |
| 26 | (1,2-diacetylbenzene) | 1 or 2 or 8a or 8b | 1 | 2 |
| 27 | (1,2-diacetylbenzene) | 1 or 2 or 8a or 8b | 1 | 3 |
| 28 | (1,2-diacetylbenzene) | 1 or 2 or 8a or 8b | 2 | 2 |
| 29 | (1,2-diacetylbenzene) | 1 or 2 or 8a or 8b | 2 | 3 |
| 30 | (1,2-diacetylbenzene) | 1 or 2 or 8a or 8b | 3 | 3 |

TABLE 3-continued
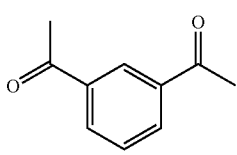
$n_a$ and $n_b$ are independantly = 1-3
| Ex. | A₁ | Viable Preparation Routes | $n_a$ | $n_b$ |
|---|---|---|---|---|
| 31 | 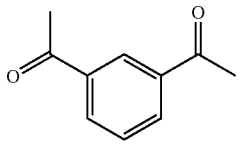 | 1 or 2 or 8a or 8b | 1 | 1 |
| 32 | 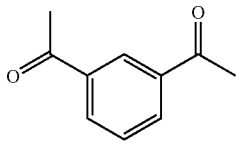 | 1 or 2 or 8a or 8b | 1 | 2 |
| 33 | 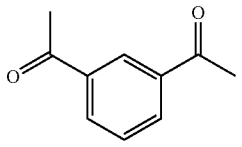 | 1 or 2 or 8a or 8b | 1 | 3 |
| 34 | 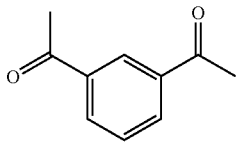 | 1 or 2 or 8a or 8b | 2 | 2 |
| 35 | 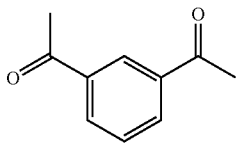 | 1 or 2 or 8a or 8b | 2 | 3 |
| 36 | 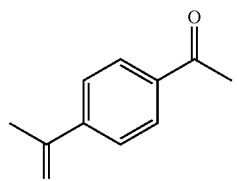 | 1 or 2 or 8a or 8b | 3 | 3 |
| 37 |  | 1 or 2 or 8a or 8b | 1 | 1 |

TABLE 3-continued
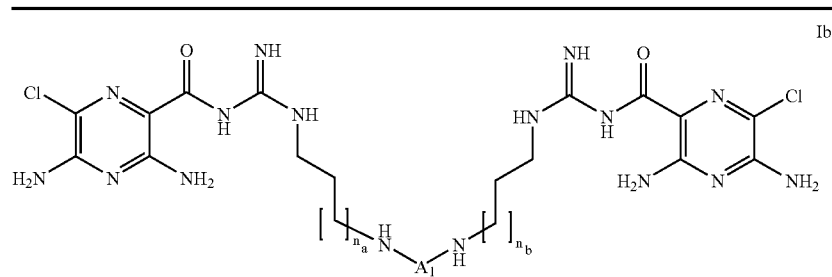
$n_a$ and $n_b$ are independantly = 1-3
| Ex. | A$_1$ | Viable Preparation Routes | $n_a$ | $n_b$ |
|---|---|---|---|---|
| 38 | (1,4-diacetylbenzene) | 1 or 2 or 8a or 8b | 1 | 2 |
| 39 | (1,4-diacetylbenzene) | 1 or 2 or 8a or 8b | 1 | 3 |
| 40 | (1,4-diacetylbenzene) | 1 or 2 or 8a or 8b | 2 | 2 |
| 41 | (1,4-diacetylbenzene) | 1 or 2 or 8a or 8b | 2 | 3 |
| 42 | (1,4-diacetylbenzene) | 1 or 2 or 8a or 8b | 3 | 3 |
| 43 | (long chain diketone, [ ]$_7$) | 1 or 2 or 8a or 8b | 1 | 1 |
| 44 | (long chain diketone, [ ]$_7$) | 1 or 2 or 8a or 8b | 1 | 2 |

TABLE 3-continued

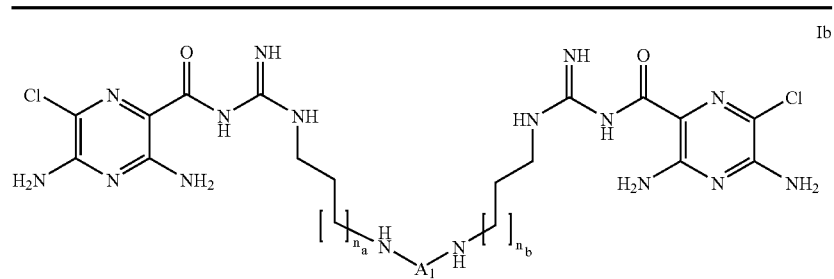

$n_a$ and $n_b$ are independantly = 1-3

| Ex. | A₁ | Viable Preparation Routes | $n_a$ | $n_b$ |
|---|---|---|---|---|
| 45 | (structure with [ ]₇) | 1 or 2 or 8a or 8b | 1 | 3 |
| 46 | (structure with [ ]₇) | 1 or 2 or 8a or 8b | 2 | 2 |
| 47 | (structure with [ ]₇) | 1 or 2 or 8a or 8b | 2 | 3 |
| 48 | (structure with [ ]₇) | 1 or 2 or 8a or 8b | 3 | 3 |
| 49 | (structure with [ ]₅) | 1 or 2 or 8a or 8b | 1 | 1 |
| 50 | (structure with [ ]₅) | 1 or 2 or 8a or 8b | 1 | 2 |
| 51 | (structure with [ ]₅) | 1 or 2 or 8a or 8b | 1 | 3 |
| 52 | (structure with [ ]₅) | 1 or 2 or 8a or 8b | 2 | 2 |
| 53 | (structure with [ ]₅) | 1 or 2 or 8a or 8b | 2 | 3 |
| 54 | (structure with [ ]₅) | 1 or 2 or 8a or 8b | 3 | 3 |
| 55 | (structure with [ ]₈) | 1 or 2 or 8a or 8b | 1 | 1 |

TABLE 3-continued
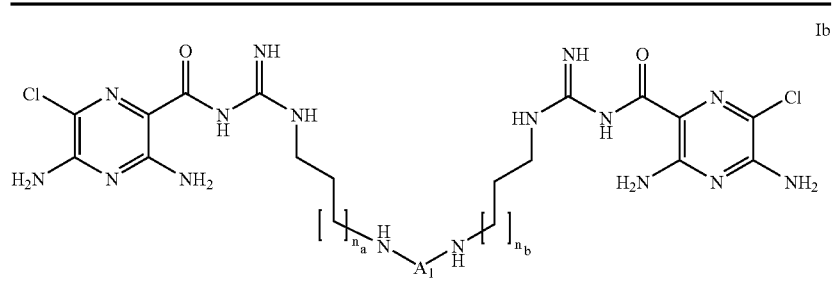
$n_a$ and $n_b$ are independantly = 1-3
| Ex. | A₁ | Viable Preparation Routes | $n_a$ | $n_b$ |
|---|---|---|---|---|
| 56 | 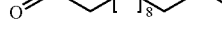 | 1 or 2 or 8a or 8b | 1 | 2 |
| 57 |  | 1 or 2 or 8a or 8b | 1 | 3 |
| 59 | 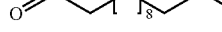 | 1 or 2 or 8a or 8b | 2 | 2 |
| 60 |  | 1 or 2 or 8a or 8b | 2 | 3 |
| 61 |  | 1 or 2 or 8a or 8b | 3 | 3 |
| 62 |  | 1 or 2 or 8a or 8b | 1 | 1 |
| 63 |  | 1 or 2 or 8a or 8b | 1 | 2 |
| 64 |  | 1 or 2 or 8a or 8b | 1 | 3 |
| 65 |  | 1 or 2 or 8a or 8b | 2 | 2 |
| 66 |  | 1 or 2 or 8a or 8b | 2 | 3 |
| 67 |  | 1 or 2 or 8a or 8b | 3 | 3 |

TABLE 3-continued
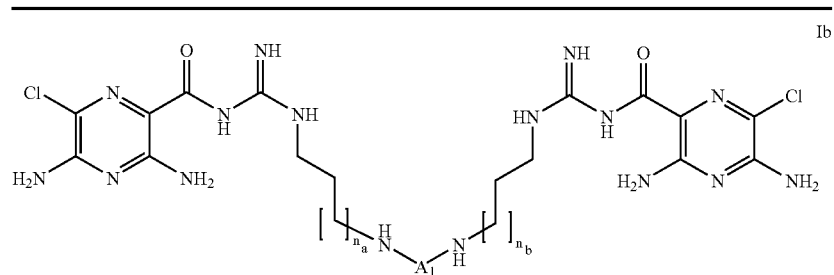
$n_a$ and $n_b$ are independantly = 1-3
| Ex. | A₁ | Viable Preparation Routes | $n_a$ | $n_b$ |
|---|---|---|---|---|
| 68 | 2,6-diacetylpyridine | 1 or 2 or 8a or 8b | 1 | 1 |
| 69 | 2,6-diacetylpyridine | 1 or 2 or 8a or 8b | 1 | 2 |
| 70 | 2,6-diacetylpyridine | 1 or 2 or 8a or 8b | 1 | 3 |
| 71 | 2,6-diacetylpyridine | 1 or 2 or 8a or 8b | 2 | 2 |
| 72 | 2,6-diacetylpyridine | 1 or 2 or 8a or 8b | 2 | 3 |
| 73 | 2,6-diacetylpyridine | 1 or 2 or 8a or 8b | 3 | 3 |
| 74 | 2,5-diacetylthiophene | 1 or 2 or 8a or 8b | 1 | 1 |
| 75 | 2,5-diacetylthiophene | 1 or 2 or 8a or 8b | 1 | 2 |

TABLE 3-continued
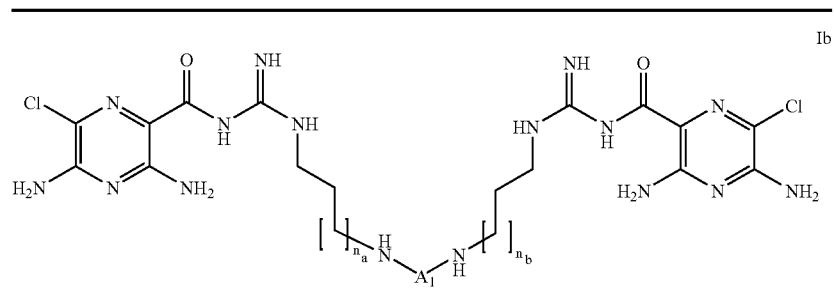
$n_a$ and $n_b$ are independantly = 1-3
| Ex. | $A_1$ | Viable Preparation Routes | $n_a$ | $n_b$ |
|---|---|---|---|---|
| 76 | | 1 or 2 or 8a or 8b | 1 | 3 |
| 77 | | 1 or 2 or 8a or 8b | 2 | 2 |
| 78 | | 1 or 2 or 8a or 8b | 2 | 3 |
| 79 | | 1 or 2 or 8a or 8b | 3 | 3 |
| 80 | | 1 or 2 or 8a or 8b | 1 | 1 |
| 81 | | 1 or 2 or 8a or 8b | 1 | 2 |
| 82 | | 1 or 2 or 8a or 8b | 1 | 3 |

TABLE 3-continued
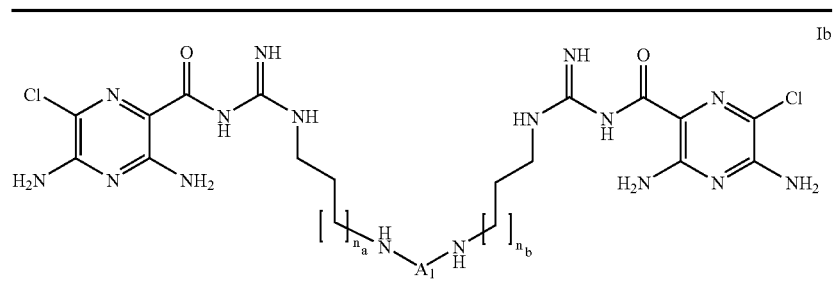
$n_a$ and $n_b$ are independantly = 1-3
| Ex. | A₁ | Viable Preparation Routes | $n_a$ | $n_b$ |
|---|---|---|---|---|
| 83 | | 1 or 2 or 8a or 8b | 2 | 2 |
| 84 | | 1 or 2 or 8a or 8b | 2 | 3 |
| 85 | | 1 or 2 or 8a or 8b | 3 | 3 |
| 86 | | 1 or 2 or 8a or 8b | 1 | 1 |
| 87 | | 1 or 2 or 8a or 8b | 1 | 2 |
| 88 | | 1 or 2 or 8a or 8b | 1 | 3 |
| 89 | | 1 or 2 or 8a or 8b | 2 | 2 |
| 90 | | 1 or 2 or 8a or 8b | 2 | 3 |
| 91 | | 1 or 2 or 8a or 8b | 3 | 3 |

TABLE 3-continued

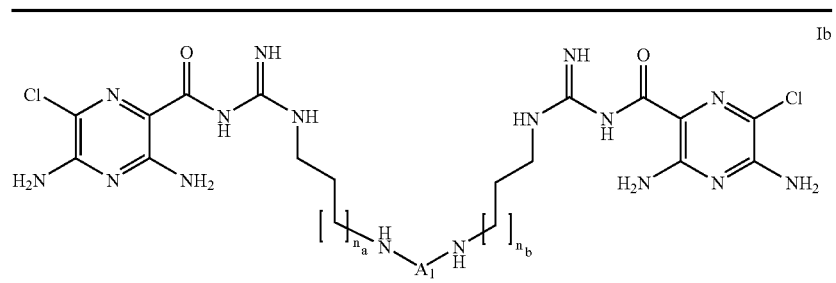

$n_a$ and $n_b$ are independantly = 1-3

| Ex. | A₁ | Viable Preparation Routes | $n_a$ | $n_b$ |
|---|---|---|---|---|
| 92 | (2,3-dimethyl-pentane-2,4-dione linker) | 1 or 2 or 8a or 8b | 1 | 1 |
| 93 | (2,3-dimethyl-pentane-2,4-dione linker) | 1 or 2 or 8a or 8b | 1 | 2 |
| 94 | (2,3-dimethyl-pentane-2,4-dione linker) | 1 or 2 or 8a or 8b | 1 | 3 |
| 95 | (2,3-dimethyl-pentane-2,4-dione linker) | 1 or 2 or 8a or 8b | 2 | 2 |
| 96 | (2,3-dimethyl-pentane-2,4-dione linker) | 1 or 2 or 8a or 8b | 2 | 3 |
| 97 | (2,3-dimethyl-pentane-2,4-dione linker) | 1 or 2 or 8a or 8b | 3 | 3 |
| 98 | (3,3-diethyl-pentane-2,4-dione linker) | 1 or 2 or 8a or 8b | 1 | 1 |
| 99 | (3,3-diethyl-pentane-2,4-dione linker) | 1 or 2 or 8a or 8b | 1 | 2 |

TABLE 3-continued
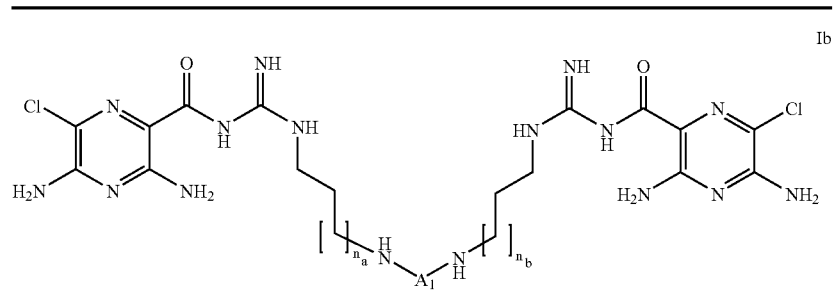
$n_a$ and $n_b$ are independantly = 1-3
| Ex. | A₁ | Viable Preparation Routes | $n_a$ | $n_b$ |
|---|---|---|---|---|
| 100 | | 1 or 2 or 8a or 8b | 1 | 3 |
| 101 | | 1 or 2 or 8a or 8b | 2 | 2 |
| 102 | | 1 or 2 or 8a or 8b | 2 | 3 |
| 103 | | 1 or 2 or 8a or 8b | 3 | 3 |
| 104 | | 1 or 2 or 8a or 8b | 1 | 1 |
| 105 | | 1 or 2 or 8a or 8b | 1 | 2 |

TABLE 3-continued
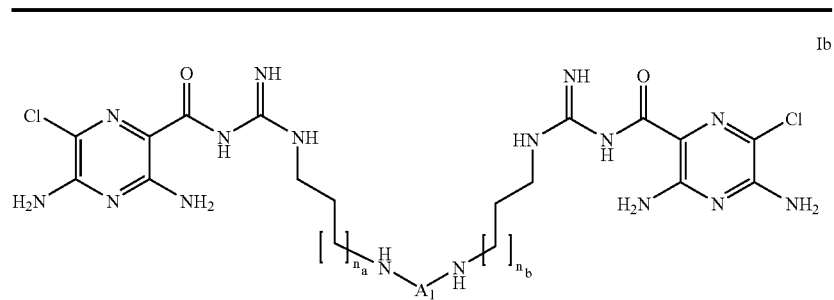
Ib
$n_a$ and $n_b$ are independantly = 1-3
| Ex. | A₁ | Viable Preparation Routes | $n_a$ | $n_b$ |
|-----|----|-----|-----|-----|
| 106 | (4-methyl-2,5-diacetylthiazole) | 1 or 2 or 8a or 8b | 1 | 3 |
| 107 | (4-methyl-2,5-diacetylthiazole) | 1 or 2 or 8a or 8b | 2 | 1 |
| 108 | (4-methyl-2,5-diacetylthiazole) | 1 or 2 or 8a or 8b | 2 | 2 |
| 109 | (4-methyl-2,5-diacetylthiazole) | 1 or 2 or 8a or 8b | 2 | 3 |
| 110 | (4-methyl-2,5-diacetylthiazole) | 1 or 2 or 8a or 8b | 3 | 1 |

TABLE 3-continued
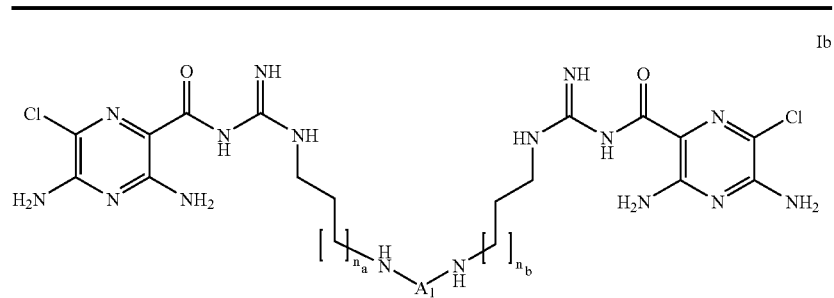
$n_a$ and $n_b$ are independantly = 1-3
| Ex. | A₁ | Viable Preparation Routes | $n_a$ | $n_b$ |
|-----|----|--------------------------|-------|-------|
| 111 | ![structure: 4-methyl-2,5-diacetylthiazole] | 1 or 2 or 8a or 8b | 3 | 2 |
| 112 | ![structure: 4-methyl-2,5-diacetylthiazole] | 1 or 2 or 8a or 8b | 3 | 3 |
| 113 | ![structure: 3,5-diacetylpyrazole] | 1 or 2 or 8a or 8b | 1 | 1 |
| 114 | ![structure: 3,5-diacetylpyrazole] | 1 or 2 or 8a or 8b | 1 | 2 |
| 115 | ![structure: 3,5-diacetylpyrazole] | 1 or 2 or 8a or 8b | 1 | 3 |

TABLE 3-continued
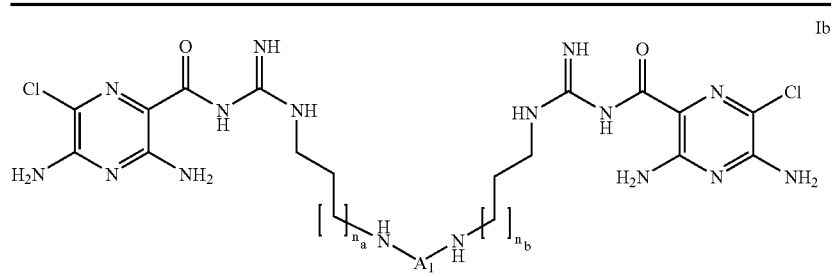
$n_a$ and $n_b$ are independantly = 1-3
| Ex. | A₁ | Viable Preparation Routes | $n_a$ | $n_b$ |
|---|---|---|---|---|
| 116 | | 1 or 2 or 8a or 8b | 2 | 2 |
| 117 | | 1 or 2 or 8a or 8b | 2 | 3 |
| 118 | | 1 or 2 or 8a or 8b | 3 | 3 |
| 119 | | 1 or 2 or 8a or 8b | 1 | 1 |
| 120 | | 1 or 2 or 8a or 8b | 1 | 2 |
| 121 | | 1 or 2 or 8a or 8b | 1 | 3 |

TABLE 3-continued
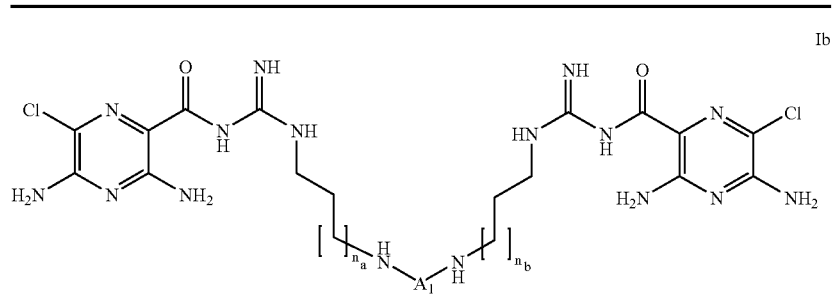
$n_a$ and $n_b$ are independantly = 1-3
| Ex. | $A_1$ | Viable Preparation Routes | $n_a$ | $n_b$ |
|---|---|---|---|---|
| 122 | ![structure] | 1 or 2 or 8a or 8b | 2 | 2 |
| 123 | ![structure] | 1 or 2 or 8a or 8b | 2 | 3 |
| 124 | ![structure] | 1 or 2 or 8a or 8b | 3 | 3 |
| 125 | ![structure] | 1 or 2 or 8a or 8b | 1 | 1 |
| 126 | ![structure] | 1 or 2 or 8a or 8b | 1 | 2 |

TABLE 3-continued
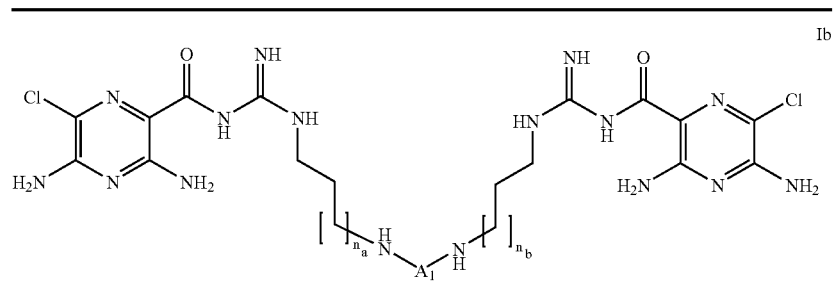
$n_a$ and $n_b$ are independantly = 1-3
| Ex. | $A_1$ | Viable Preparation Routes | $n_a$ | $n_b$ |
|---|---|---|---|---|
| 127 | *trans-1,4-diacetylcyclohexane* | 1 or 2 or 8a or 8b | 1 | 3 |
| 128 | *trans-1,4-diacetylcyclohexane* | 1 or 2 or 8a or 8b | 2 | 2 |
| 129 | *trans-1,4-diacetylcyclohexane* | 1 or 2 or 8a or 8b | 2 | 3 |
| 130 | *trans-1,4-diacetylcyclohexane* | 1 or 2 or 8a or 8b | 3 | 3 |
| 131 | *1,4-phenylenediacetone* | 1 or 2 or 8a or 8b | 1 | 1 |
| 132 | *1,4-phenylenediacetone* | 1 or 2 or 8a or 8b | 1 | 2 |
| 133 | *1,4-phenylenediacetone* | 1 or 2 or 8a or 8b | 1 | 3 |

TABLE 3-continued $n_a$ and $n_b$ are independantly = 1-3

| Ex. | $A_1$ | Viable Preparation Routes | $n_a$ | $n_b$ |
|---|---|---|---|---|
| 134 | (1,4-phenylene-bis(acetone)) | 1 or 2 or 8a or 8b | 2 | 2 |
| 135 | (1,4-phenylene-bis(acetone)) | 1 or 2 or 8a or 8b | 2 | 3 |
| 136 | (1,4-phenylene-bis(acetone)) | 1 or 2 or 8a or 8b | 3 | 3 |
| 137 | (2,5-diacetylpyrazine) | 1 or 2 or 8a or 8b | 1 | 1 |
| 138 | (2,5-diacetylpyrazine) | 1 or 2 or 8a or 8b | 1 | 2 |
| 139 | (2,5-diacetylpyrazine) | 1 or 2 or 8a or 8b | 1 | 3 |
| 140 | (2,5-diacetylpyrazine) | 1 or 2 or 8a or 8b | 2 | 2 |

TABLE 3-continued
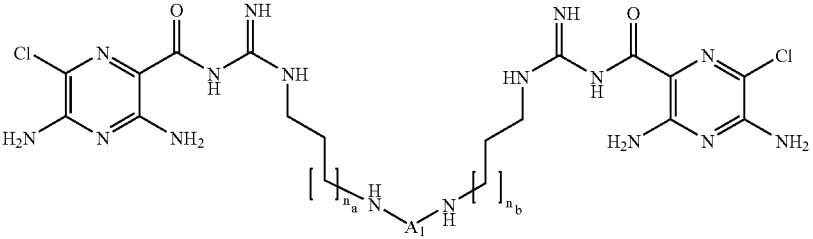
$n_a$ and $n_b$ are independantly = 1-3
| Ex. | $A_1$ | Viable Preparation Routes | $n_a$ | $n_b$ |
|---|---|---|---|---|
| 141 | 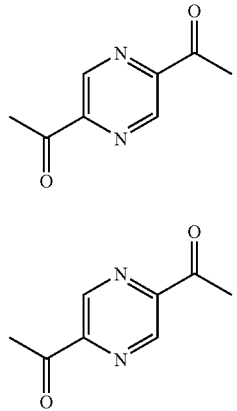 | 1 or 2 or 8a or 8b | 2 | 3 |
| 142 | 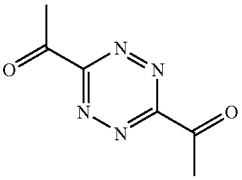 | 1 or 2 or 8a or 8b | 3 | 3 |
| 143 | 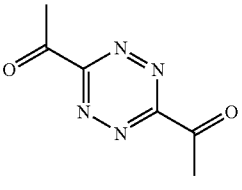 | 1 or 2 or 8a or 8b | 1 | 1 |
| 144 | 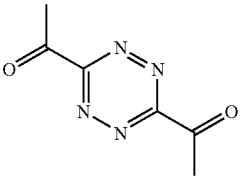 | 1 or 2 or 8a or 8b | 1 | 2 |
| 145 | 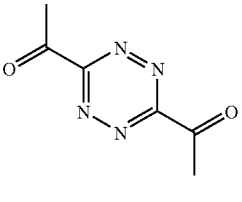 | 1 or 2 or 8a or 8b | 1 | 3 |
| 146 |  | 1 or 2 or 8a or 8b | 2 | 2 |

TABLE 3-continued
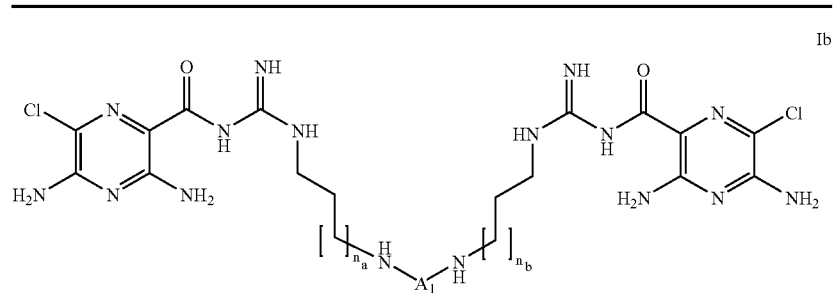
Ib
$n_a$ and $n_b$ are independantly = 1-3
| Ex. | $A_1$ | Viable Preparation Routes | $n_a$ | $n_b$ |
|---|---|---|---|---|
| 147 | (diacetyl tetrazine) | 1 or 2 or 8a or 8b | 2 | 3 |
| 148 | (diacetyl tetrazine) | 1 or 2 or 8a or 8b | 3 | 3 |
| 149 | (2,4-diacetyl pyridine) | 1 or 2 or 8a or 8b | 1 | 1 |
| 150 | (2,4-diacetyl pyridine) | 1 or 2 or 8a or 8b | 1 | 2 |
| 151 | (2,4-diacetyl pyridine) | 1 or 2 or 8a or 8b | 1 | 3 |

TABLE 3-continued
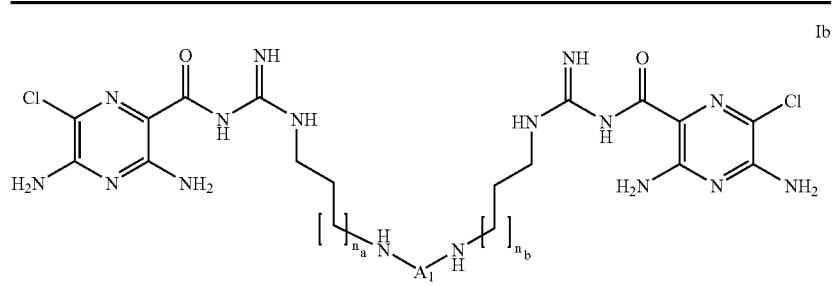
$n_a$ and $n_b$ are independantly = 1-3
| Ex. | A$_1$ | Viable Preparation Routes | n$_a$ | n$_b$ |
|---|---|---|---|---|
| 152 | 2,4-diacetylpyridine | 1 or 2 or 8a or 8b | 2 | 1 |
| 153 | 2,4-diacetylpyridine | 1 or 2 or 8a or 8b | 2 | 2 |
| 154 | 2,4-diacetylpyridine | 1 or 2 or 8a or 8b | 2 | 3 |
| 155 | 2,4-diacetylpyridine | 1 or 2 or 8a or 8b | 3 | 1 |
| 156 | 2,4-diacetylpyridine | 1 or 2 or 8a or 8b | 3 | 2 |

TABLE 3-continued
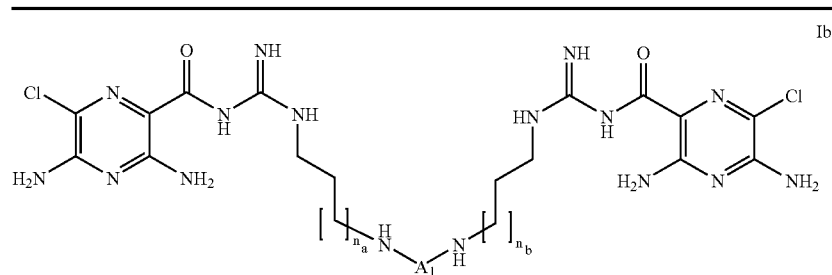
$n_a$ and $n_b$ are independantly = 1-3
| Ex. | A₁ | Viable Preparation Routes | $n_a$ | $n_b$ |
|---|---|---|---|---|
| 157 | (2,4-diacetylpyridine) | 1 or 2 or 8a or 8b | 3 | 3 |
| 158 | (1,4-diacetyltetralin) | 1 or 2 or 8a or 8b | 1 | 1 |
| 159 | (1,4-diacetyltetralin) | 1 or 2 or 8a or 8b | 1 | 2 |
| 160 | (1,4-diacetyltetralin) | 1 or 2 or 8a or 8b | 1 | 3 |
| 161 | (1,4-diacetyltetralin) | 1 or 2 or 8a or 8b | 2 | 2 |

TABLE 3-continued
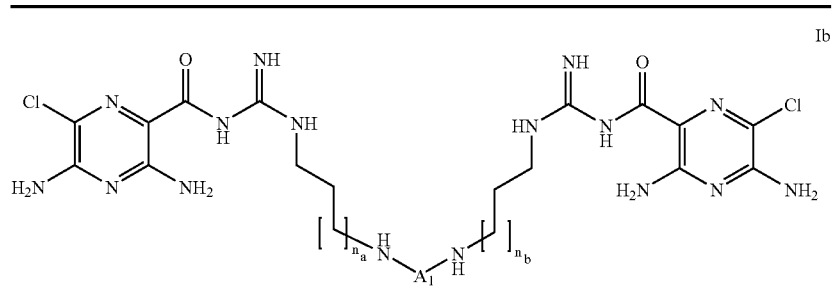
$n_a$ and $n_b$ are independantly = 1-3
| Ex. | A₁ | Viable Preparation Routes | $n_a$ | $n_b$ |
|---|---|---|---|---|
| 162 | (1,4-diacetyl tetralin) | 1 or 2 or 8a or 8b | 2 | 3 |
| 163 | (1,4-diacetyl tetralin) | 1 or 2 or 8a or 8b | 3 | 3 |
| 164 | (2,7-diacetyl biphenylene) | 1 or 2 or 8a or 8b | 1 | 1 |
| 165 | (2,7-diacetyl biphenylene) | 1 or 2 or 8a or 8b | 1 | 2 |
| 166 | (2,7-diacetyl biphenylene) | 1 or 2 or 8a or 8b | 1 | 3 |

TABLE 3-continued $n_a$ and $n_b$ are independantly = 1-3

| Ex. | A₁ | Viable Preparation Routes | $n_a$ | $n_b$ |
|---|---|---|---|---|
| 167 | (2,7-diacetyl biphenylene) | 1 or 2 or 8a or 8b | 2 | 2 |
| 168 | (2,7-diacetyl biphenylene) | 1 or 2 or 8a or 8b | 2 | 3 |
| 169 | (2,7-diacetyl biphenylene) | 1 or 2 or 8a or 8b | 3 | 3 |
| 170 | (3,6-diacetyl pyridazine) | 1 or 2 or 8a or 8b | 1 | 1 |
| 171 | (3,6-diacetyl pyridazine) | 1 or 2 or 8a or 8b | 1 | 2 |
| 172 | (3,6-diacetyl pyridazine) | 1 or 2 or 8a or 8b | 1 | 3 |

TABLE 3-continued
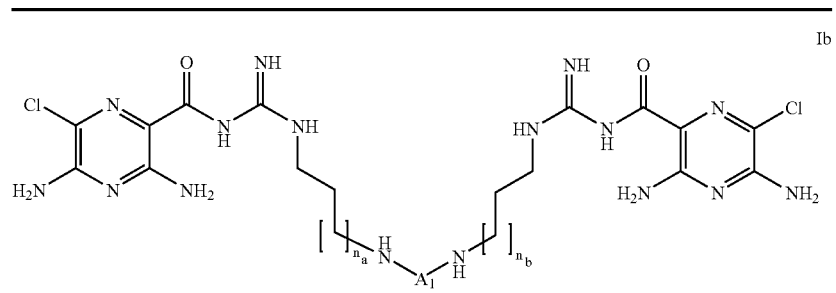
$n_a$ and $n_b$ are independantly = 1-3
| Ex. | A₁ | Viable Preparation Routes | $n_a$ | $n_b$ |
|---|---|---|---|---|
| 173 | (3,6-diacetyl pyridazine) | 1 or 2 or 8a or 8b | 2 | 2 |
| 174 | (3,6-diacetyl pyridazine) | 1 or 2 or 8a or 8b | 2 | 3 |
| 175 | (3,6-diacetyl pyridazine) | 1 or 2 or 8a or 8b | 3 | 3 |
| 176 | (3,4-diacetyl furazan) | 1 or 2 or 8a or 8b | 1 | 1 |
| 177 | (3,4-diacetyl furazan) | 1 or 2 or 8a or 8b | 1 | 2 |
| 178 | (3,4-diacetyl furazan) | 1 or 2 or 8a or 8b | 1 | 3 |

TABLE 3-continued
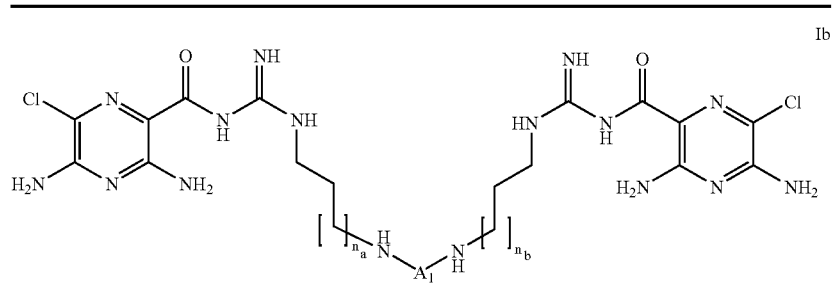
$n_a$ and $n_b$ are independantly = 1-3
| Ex. | A₁ | Viable Preparation Routes | $n_a$ | $n_b$ |
|---|---|---|---|---|
| 180 | | 1 or 2 or 8a or 8b | 2 | 2 |
| 181 | | 1 or 2 or 8a or 8b | 2 | 3 |
| 182 | | 1 or 2 or 8a or 8b | 3 | 3 |
| 183 | | 1 or 2 or 8a or 8b | 1 | 1 |
| 184 | | 1 or 2 or 8a or 8b | 1 | 2 |
| 185 | | 1 or 2 or 8a or 8b | 1 | 3 |

TABLE 3-continued
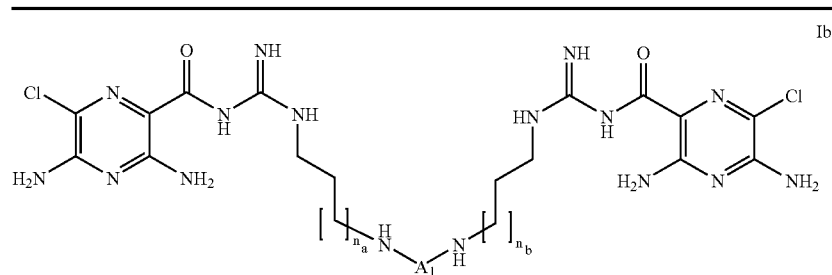
$n_a$ and $n_b$ are independantly = 1-3
| Ex. | A₁ | Viable Preparation Routes | $n_a$ | $n_b$ |
|---|---|---|---|---|
| 186 | (norbornene with two acetyl groups) | 1 or 2 or 8a or 8b | 2 | 2 |
| 187 | (norbornene with two acetyl groups) | 1 or 2 or 8a or 8b | 2 | 3 |
| 188 | (norbornene with two acetyl groups) | 1 or 2 or 8a or 8b | 3 | 3 |
| 189 | (1,3-diacetylcyclohexane) | 1 or 2 or 8a or 8b | 1 | 1 |
| 190 | (1,3-diacetylcyclohexane) | 1 or 2 or 8a or 8b | 1 | 2 |
| 191 | (1,3-diacetylcyclohexane) | 1 or 2 or 8a or 8b | 1 | 3 |
| 192 | (1,3-diacetylcyclohexane) | 1 or 2 or 8a or 8b | 2 | 2 |

TABLE 3-continued
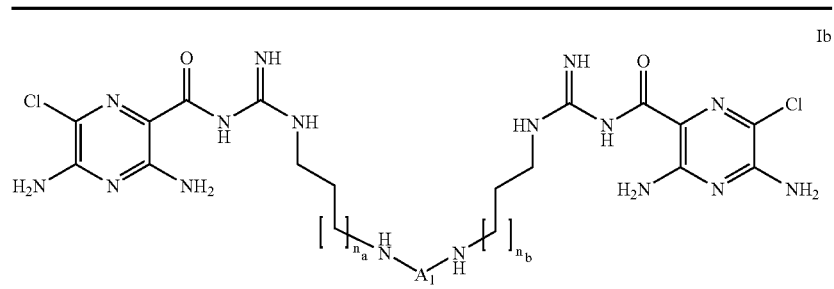
$n_a$ and $n_b$ are independantly = 1-3
| Ex. | $A_1$ | Viable Preparation Routes | $n_a$ | $n_b$ |
|---|---|---|---|---|
| 193 | | 1 or 2 or 8a or 8b | 2 | 3 |
| 194 | | 1 or 2 or 8a or 8b | 3 | 3 |
| 195 | | 1 or 2 or 8a or 8b | 1 | 1 |
| 196 | | 1 or 2 or 8a or 8b | 1 | 2 |
| 197 | | 1 or 2 or 8a or 8b | 1 | 3 |
| 198 | | 1 or 2 or 8a or 8b | 2 | 2 |

TABLE 3-continued
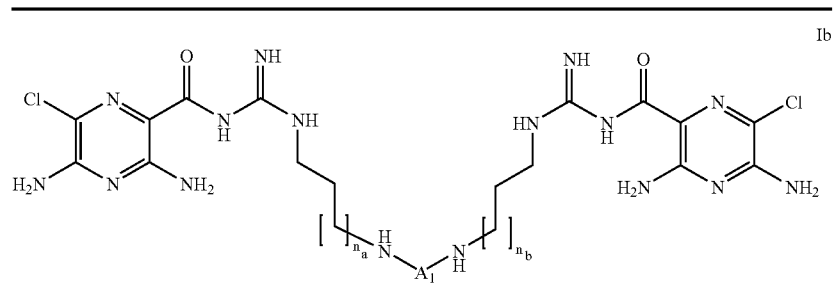
$n_a$ and $n_b$ are independantly = 1-3
| Ex. | A₁ | Viable Preparation Routes | $n_a$ | $n_b$ |
|---|---|---|---|---|
| 199 | | 1 or 2 or 8a or 8b | 2 | 3 |
| 200 | | 1 or 2 or 8a or 8b | 3 | 3 |
| 201 | | 1 or 2 or 8a or 8b | 1 | 1 |
| 202 | | 1 or 2 or 8a or 8b | 1 | 2 |
| 203 | | 1 or 2 or 8a or 8b | 1 | 3 |
| 204 | | 1 or 2 or 8a or 8b | 2 | 2 |

TABLE 3-continued $n_a$ and $n_b$ are independantly = 1-3

| Ex. | $A_1$ | Viable Preparation Routes | $n_a$ | $n_b$ |
|---|---|---|---|---|
| 205 | (diacetyl tetrazine) | 1 or 2 or 8a or 8b | 2 | 3 |
| 206 | (diacetyl tetrazine) | 1 or 2 or 8a or 8b | 3 | 3 |
| 207 | (diacetyl furan) | 1 or 2 or 8a or 8b | 1 | 1 |
| 208 | (diacetyl furan) | 1 or 2 or 8a or 8b | 1 | 2 |
| 209 | (diacetyl furan) | 1 or 2 or 8a or 8b | 1 | 3 |
| 210 | (diacetyl furan) | 1 or 2 or 8a or 8b | 2 | 2 |
| 211 | (diacetyl furan) | 1 or 2 or 8a or 8b | 2 | 3 |
| 212 | (diacetyl furan) | 1 or 2 or 8a or 8b | 3 | 3 |

TABLE 3-continued
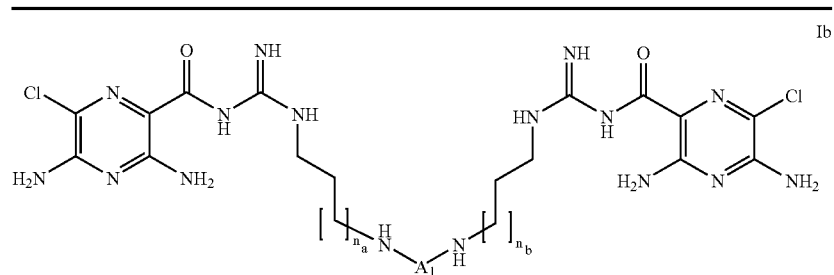
Ib
$n_a$ and $n_b$ are independantly = 1-3
| Ex. | $A_1$ | Viable Preparation Routes | $n_a$ | $n_b$ |
|---|---|---|---|---|
| 213 | 2,6-diacetylnaphthalene | 1 or 2 or 8a or 8b | 1 | 1 |
| 214 | 2,6-diacetylnaphthalene | 1 or 2 or 8a or 8b | 1 | 2 |
| 215 | 2,6-diacetylnaphthalene | 1 or 2 or 8a or 8b | 1 | 3 |
| 216 | 2,6-diacetylnaphthalene | 1 or 2 or 8a or 8b | 2 | 2 |
| 217 | 2,6-diacetylnaphthalene | 1 or 2 or 8a or 8b | 2 | 3 |
| 218 | 2,6-diacetylnaphthalene | 1 or 2 or 8a or 8b | 3 | 3 |

TABLE 3-continued $n_a$ and $n_b$ are independantly = 1-3

| Ex. | $A_1$ | Viable Preparation Routes | $n_a$ | $n_b$ |
|---|---|---|---|---|
| 219 | 3,5-diacetylpyridine | 1 or 2 or 8a or 8b | 1 | 1 |
| 220 | 3,5-diacetylpyridine | 1 or 2 or 8a or 8b | 1 | 2 |
| 221 | 3,5-diacetylpyridine | 1 or 2 or 8a or 8b | 1 | 3 |
| 222 | 3,5-diacetylpyridine | 1 or 2 or 8a or 8b | 2 | 2 |
| 223 | 3,5-diacetylpyridine | 1 or 2 or 8a or 8b | 2 | 3 |
| 224 | 3,5-diacetylpyridine | 1 or 2 or 8a or 8b | 3 | 3 |
| 225 | diacetyl-oxabicyclic | 1 or 2 or 8a or 8b | 1 | 1 |

TABLE 3-continued
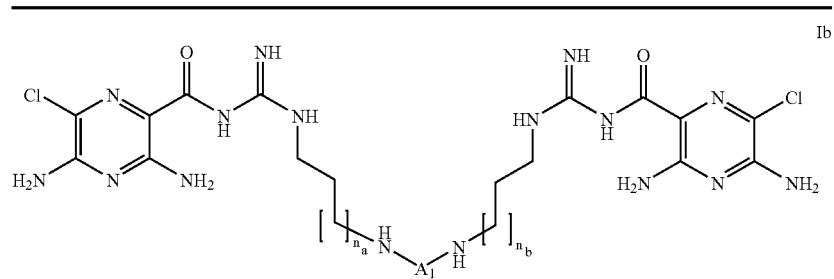
$n_a$ and $n_b$ are independantly = 1-3
| Ex. | A$_1$ | Viable Preparation Routes | n$_a$ | n$_b$ |
|---|---|---|---|---|
| 226 | | 1 or 2 or 8a or 8b | 1 | 2 |
| 227 | | 1 or 2 or 8a or 8b | 1 | 3 |
| 228 | | 1 or 2 or 8a or 8b | 2 | 2 |
| 229 | | 1 or 2 or 8a or 8b | 2 | 3 |
| 230 | | 1 or 2 or 8a or 8b | 3 | 3 |
| 231 | | 1 or 2 or 8a or 8b | 1 | 1 |

TABLE 3-continued
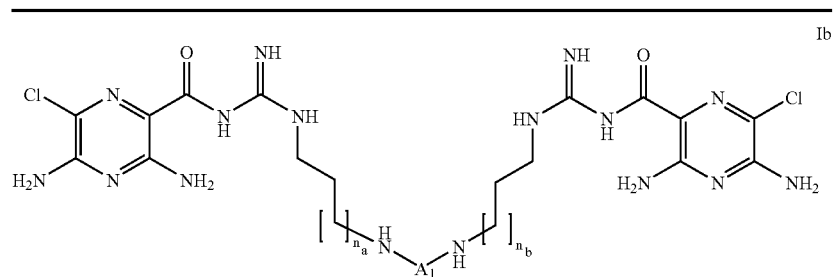
$n_a$ and $n_b$ are independantly = 1-3
| Ex. | $A_1$ | Viable Preparation Routes | $n_a$ | $n_b$ |
|---|---|---|---|---|
| 232 | | 1 or 2 or 8a or 8b | 1 | 2 |
| 233 | | 1 or 2 or 8a or 8b | 1 | 3 |
| 234 | | 1 or 2 or 8a or 8b | 2 | 2 |
| 235 | | 1 or 2 or 8a or 8b | 2 | 3 |
| 237 | | 1 or 2 or 8a or 8b | 3 | 3 |
| 238 | | 1 or 2 or 8a or 8b | 1 | 1 |

TABLE 3-continued
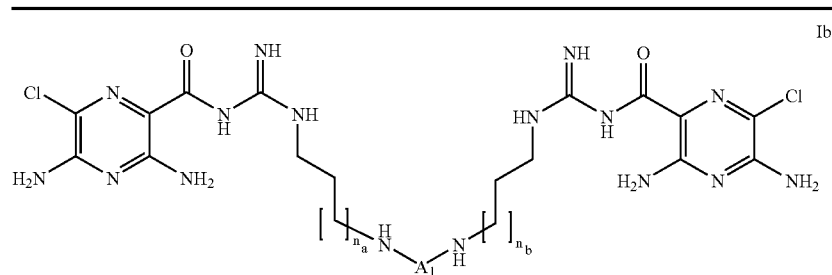
$n_a$ and $n_b$ are independantly = 1-3
| Ex. | A₁ | Viable Preparation Routes | $n_a$ | $n_b$ |
|---|---|---|---|---|
| 239 | | 1 or 2 or 8a or 8b | 1 | 2 |
| 240 | | 1 or 2 or 8a or 8b | 1 | 3 |
| 241 | | 1 or 2 or 8a or 8b | 2 | 2 |
| 242 | | 1 or 2 or 8a or 8b | 3 | 2 |
| 243 | | 1 or 2 or 8a or 8b | 3 | 3 |
| 244 | | 1 or 2 or 8a or 8b | 1 | 1 |
| 245 | | 1 or 2 or 8a or 8b | 1 | 2 |
| 246 | | 1 or 2 or 8a or 8b | 1 | 3 |

TABLE 3-continued
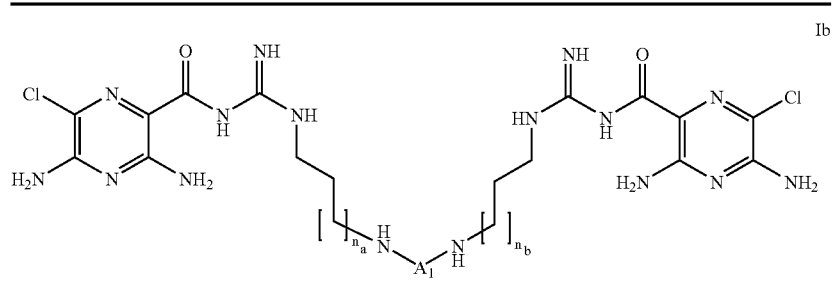
$n_a$ and $n_b$ are independantly = 1-3
| Ex. | $A_1$ | Viable Preparation Routes | $n_a$ | $n_b$ |
|---|---|---|---|---|
| 247 | | 1 or 2 or 8a or 8b | 2 | 2 |
| 248 | | 1 or 2 or 8a or 8b | 2 | 3 |
| 249 | | 1 or 2 or 8a or 8b | 3 | 3 |
| 250 | | 1 or 2 or 8a or 8b | 1 | 1 |
| 251 | | 1 or 2 or 8a or 8b | 1 | 2 |
| 252 | | 1 or 2 or 8a or 8b | 1 | 3 |
| 253 | | 1 or 2 or 8a or 8b | 2 | 2 |

TABLE 3-continued
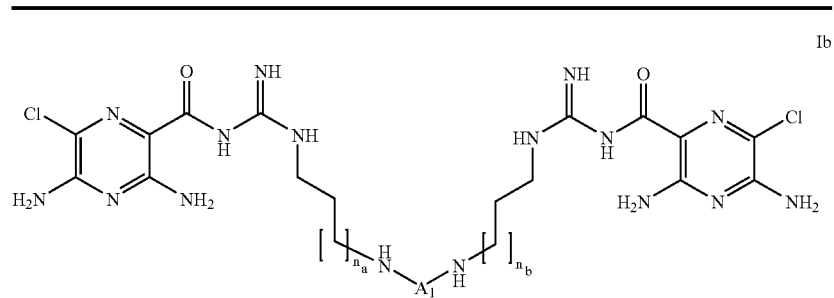
$n_a$ and $n_b$ are independantly = 1-3
| Ex. | $A_1$ | Viable Preparation Routes | $n_a$ | $n_b$ |
|---|---|---|---|---|
| 254 | | 1 or 2 or 8a or 8b | 2 | 3 |
| 255 | | 1 or 2 or 8a or 8b | 3 | 3 |
| 256 | | 3 or 8c | 1 | 1 |
| 257 | | 3 or 8c | 1 | 2 |
| 259 | | 3 or 8c | 1 | 3 |

TABLE 3-continued
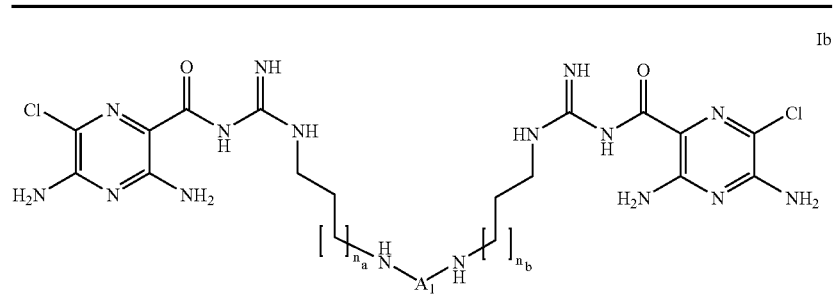
$n_a$ and $n_b$ are independantly = 1-3
| Ex. | $A_1$ | Viable Preparation Routes | $n_a$ | $n_b$ |
|---|---|---|---|---|
| 260 | | 3 or 8c | 2 | 2 |
| 261 | | 3 or 8c | 2 | 3 |
| 262 | | 3 or 8c | 3 | 3 |
| 263 | | 3 or 8c | 1 | 1 |

TABLE 3-continued
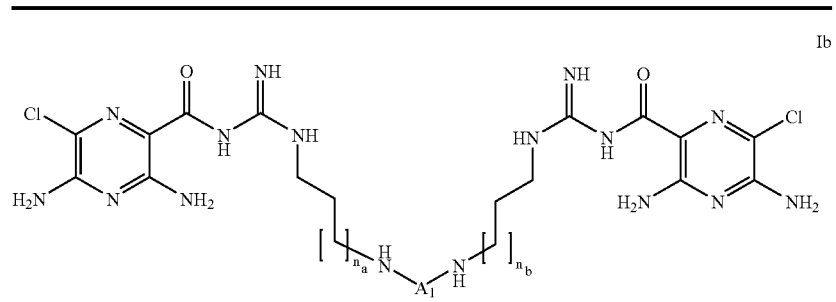
Ib
$n_a$ and $n_b$ are independantly = 1-3
| Ex. | $A_1$ | Viable Preparation Routes | $n_a$ | $n_b$ |
|---|---|---|---|---|
| 264 | | 3 or 8c | 1 | 2 |
| 265 | | 3 or 8c | 1 | 3 |
| 266 | | 3 or 8c | 2 | 2 |

TABLE 3-continued
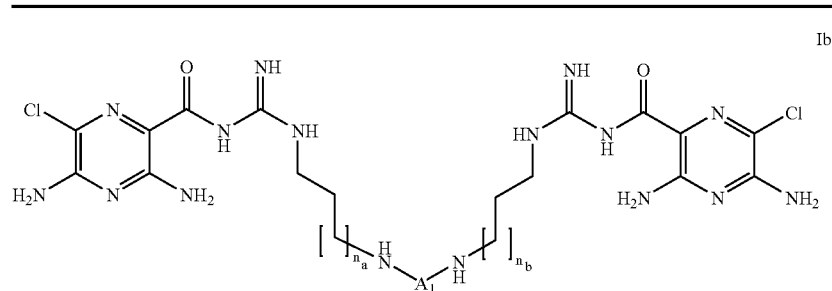
$n_a$ and $n_b$ are independantly = 1-3
| Ex. | A₁ | Viable Preparation Routes | $n_a$ | $n_b$ |
|---|---|---|---|---|
| 267 | (1,5-naphthalene bis-acetamide) | 3 or 8c | 2 | 3 |
| 268 | (1,5-naphthalene bis-acetamide) | 3 or 8c | 3 | 3 |
| 269 | (1,4-phenylene bis-acetamide) | 3 or 8c | 1 | 1 |
| 270 | (1,4-phenylene bis-acetamide) | 3 or 8c | 1 | 2 |

TABLE 3-continued
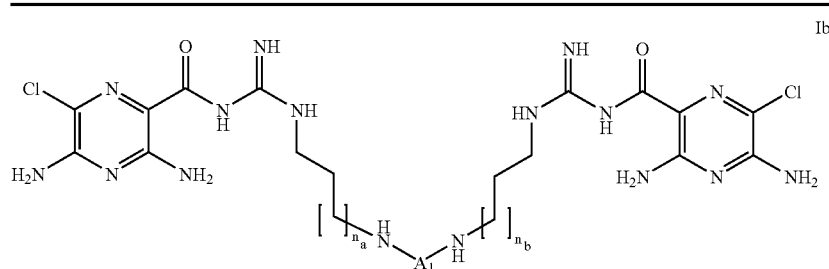
$n_a$ and $n_b$ are independantly = 1-3
| Ex. | A₁ | Viable Preparation Routes | $n_a$ | $n_b$ |
|---|---|---|---|---|
| 271 | | 3 or 8c | 1 | 3 |
| 272 | | 3 or 8c | 2 | 2 |
| 273 | | 3 or 8c | 2 | 3 |
| 274 | | 3 or 8c | 3 | 3 |
| 275 | | 3 or 8c | 1 | 1 |
| 276 | | 3 or 8c | 1 | 2 |

TABLE 3-continued
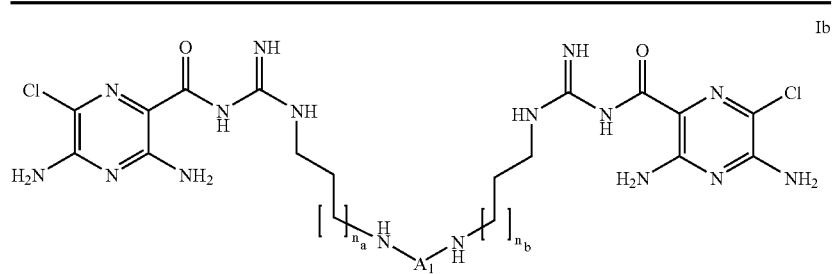
$n_a$ and $n_b$ are independantly = 1-3
| Ex. | A₁ | Viable Preparation Routes | $n_a$ | $n_b$ |
|---|---|---|---|---|
| 277 | (3-acetamidophenyl)acetamide | 3 or 8c | 1 | 3 |
| 278 | (3-acetamidophenyl)acetamide | 3 or 8c | 2 | 2 |
| 279 | (3-acetamidophenyl)acetamide | 3 or 8c | 2 | 3 |
| 280 | (3-acetamidophenyl)acetamide | 3 or 8c | 3 | 3 |
| 281 | (4-acetamidocyclohexyl)acetamide | 3 or 8c | 1 | 1 |
| 282 | (4-acetamidocyclohexyl)acetamide | 3 or 8c | 1 | 2 |

TABLE 3-continued
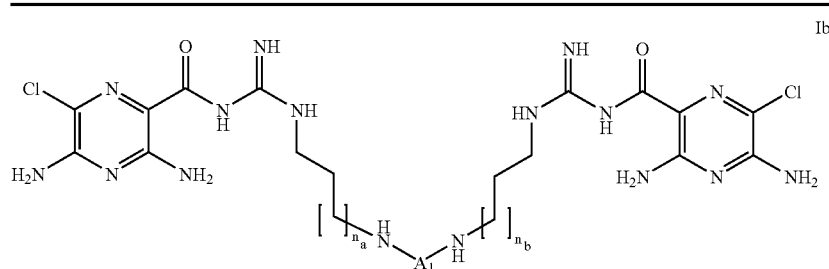
$n_a$ and $n_b$ are independantly = 1-3
| Ex. | A₁ | Viable Preparation Routes | $n_a$ | $n_b$ |
|---|---|---|---|---|
| 283 | | 3 or 8c | 1 | 3 |
| 284 | | 3 or 8c | 2 | 2 |
| 285 | | 3 or 8c | 3 | 2 |
| 286 | | 3 or 8c | 3 | 3 |
| 287 | | 3 or 8c | 1 | 1 |
| 288 | | 3 or 8c | 1 | 2 |

TABLE 3-continued
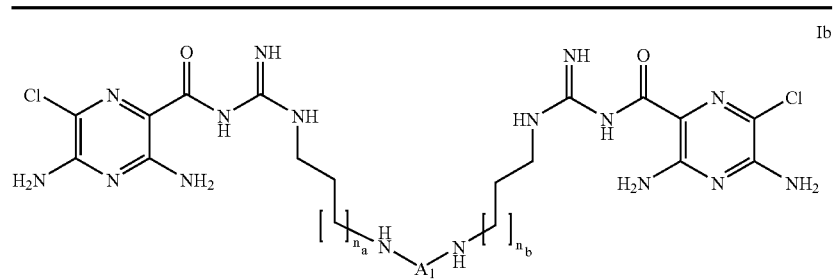
$n_a$ and $n_b$ are independantly = 1-3
| Ex. | A₁ | Viable Preparation Routes | $n_a$ | $n_b$ |
|---|---|---|---|---|
| 289 | | 3 or 8c | 1 | 3 |
| 290 | | 3 or 8c | 2 | 2 |
| 291 | | 3 or 8c | 2 | 3 |
| 292 | | 3 or 8c | 3 | 3 |
| 293 | | 3 or 8c | 1 | 1 |
| 294 | | 3 or 8c | 1 | 2 |

TABLE 3-continued
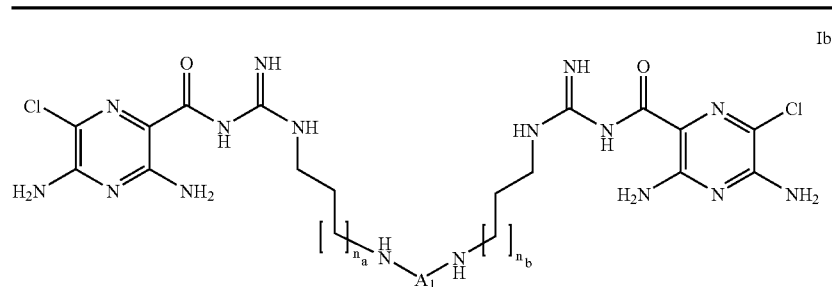
$n_a$ and $n_b$ are independantly = 1-3
| Ex. | $A_1$ | Viable Preparation Routes | $n_a$ | $n_b$ |
|---|---|---|---|---|
| 295 | | 3 or 8c | 1 | 3 |
| 296 | | 3 or 8c | 2 | 2 |
| 297 | | 3 or 8c | 2 | 3 |
| 298 | | 3 or 8c | 3 | 3 |
| 299 | | 3 or 8c | 1 | 1 |

TABLE 3-continued
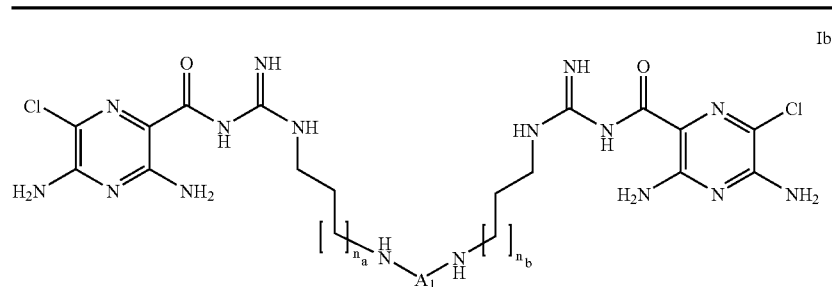
Ib
$n_a$ and $n_b$ are independantly = 1-3
| Ex. | A₁ | Viable Preparation Routes | $n_a$ | $n_b$ |
|---|---|---|---|---|
| 300 | | 3 or 8c | 1 | 2 |
| 301 | | 3 or 8c | 1 | 3 |
| 302 | | 3 or 8c | 2 | 2 |
| 303 | | 3 or 8c | 2 | 3 |
| 304 | | 3 or 8c | 3 | 3 |

TABLE 3-continued
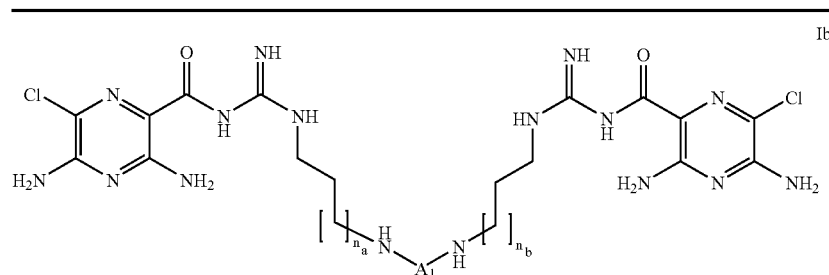
$n_a$ and $n_b$ are independantly = 1-3
| Ex. | $A_1$ | Viable Preparation Routes | $n_a$ | $n_b$ |
|---|---|---|---|---|
| 305 | | 4 or 8d | 1 | 1 |
| 306 | | 4 or 8d | 1 | 2 |
| 307 | | 4 or 8d | 1 | 3 |
| 308 | | 4 or 8d | 2 | 2 |
| 309 | | 4 or 8d | 2 | 3 |
| 310 | | 4 or 8d | 3 | 3 |
| 311 | | 4 or 8d | 1 | 1 |

TABLE 3-continued
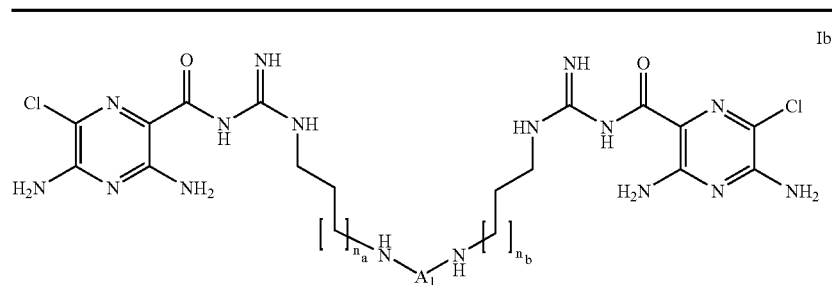
$n_a$ and $n_b$ are independantly = 1-3
| Ex. | $A_1$ | Viable Preparation Routes | $n_a$ | $n_b$ |
|---|---|---|---|---|
| 312 | | 4 or 8d | 1 | 2 |
| 313 | | 4 or 8d | 1 | 3 |
| 314 | | 4 or 8d | 2 | 2 |
| 318 | | 4 or 8d | 2 | 3 |
| 319 | | 4 or 8d | 3 | 3 |
| 320 | | 4 or 8d | 1 | 1 |
| 321 | | 4 or 8d | 1 | 2 |
| 322 | | 4 or 8d | 1 | 3 |

TABLE 3-continued
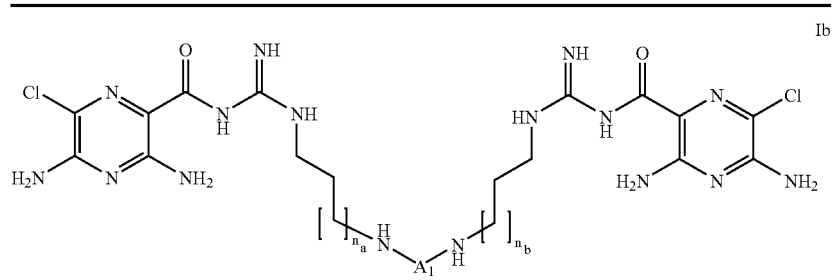
$n_a$ and $n_b$ are independantly = 1-3
| Ex. | A₁ | Viable Preparation Routes | $n_a$ | $n_b$ |
|---|---|---|---|---|
| 323 | | 4 or 8d | 2 | 2 |
| 324 | | 4 or 8d | 2 | 3 |
| 325 | | 4 or 8d | 3 | 3 |
| 326 | | 4 or 8d | 1 | 1 |
| 327 | | 4 or 8d | 1 | 2 |
| 328 | | 4 or 8d | 1 | 3 |

TABLE 3-continued
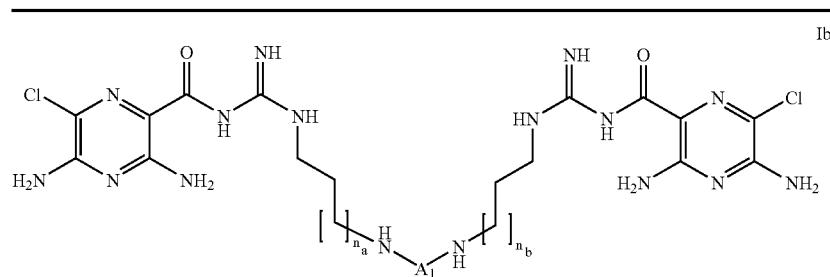
$n_a$ and $n_b$ are independantly = 1-3
| Ex. | $A_1$ | Viable Preparation Routes | $n_a$ | $n_b$ |
|---|---|---|---|---|
| 329 | ![tetrazine with two acetamido groups] | 4 or 8d | 2 | 2 |
| 330 | ![tetrazine with two acetamido groups] | 4 or 8d | 2 | 3 |
| 331 | ![tetrazine with two acetamido groups] | 4 or 8d | 3 | 3 |
| 332 | ![pyridine with two acetamido groups] | 4 or 8d | 1 | 1 |
| 333 | ![pyridine with two acetamido groups] | 4 or 8d | 1 | 2 |

TABLE 3-continued
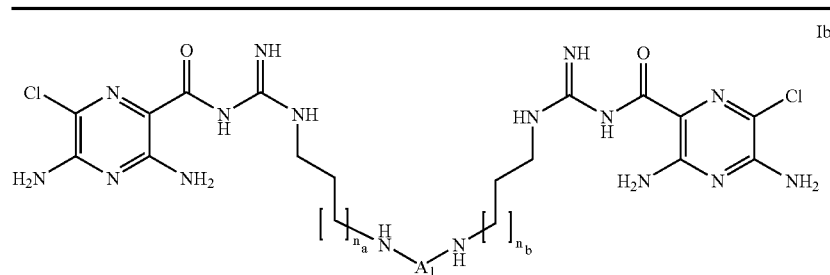
$n_a$ and $n_b$ are independantly = 1-3
| Ex. | A₁ | Viable Preparation Routes | $n_a$ | $n_b$ |
|---|---|---|---|---|
| 334 | (2,4-diacetamidopyridinyl) | 4 or 8d | 1 | 3 |
| 335 | (2,4-diacetamidopyridinyl) | 4 or 8d | 2 | 1 |
| 336 | (2,4-diacetamidopyridinyl) | 4 or 8d | 2 | 2 |
| 337 | (2,4-diacetamidopyridinyl) | 4 or 8d | 2 | 3 |
| 338 | (2,4-diacetamidopyridinyl) | 4 or 8d | 3 | 1 |

TABLE 3-continued
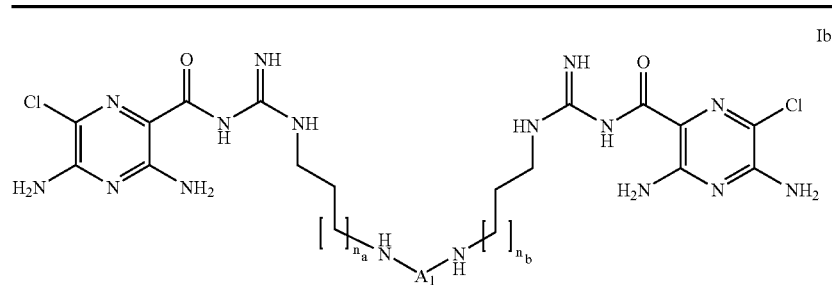
$n_a$ and $n_b$ are independantly = 1-3
| Ex. | A₁ | Viable Preparation Routes | $n_a$ | $n_b$ |
|---|---|---|---|---|
| 339 | | 4 or 8d | 3 | 2 |
| 340 | | 4 or 8d | 3 | 3 |
| 341 | | 4 or 8d | 1 | 1 |
| 342 | | 4 or 8d | 1 | 2 |

TABLE 3-continued
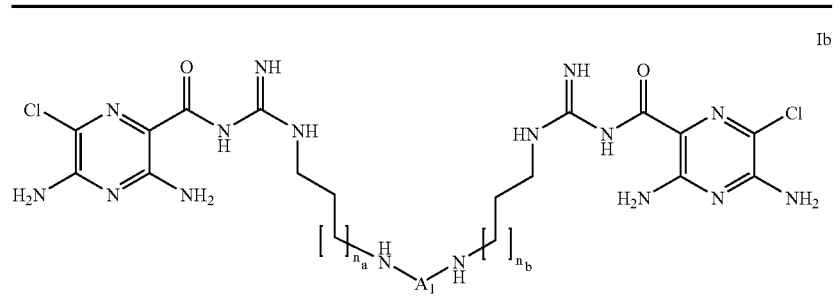
$n_a$ and $n_b$ are independantly = 1-3
| Ex. | $A_1$ | Viable Preparation Routes | $n_a$ | $n_b$ |
|---|---|---|---|---|
| 343 | | 4 or 8d | 1 | 3 |
| 344 | | 4 or 8d | 2 | 2 |
| 345 | | 4 or 8d | 2 | 3 |

TABLE 3-continued
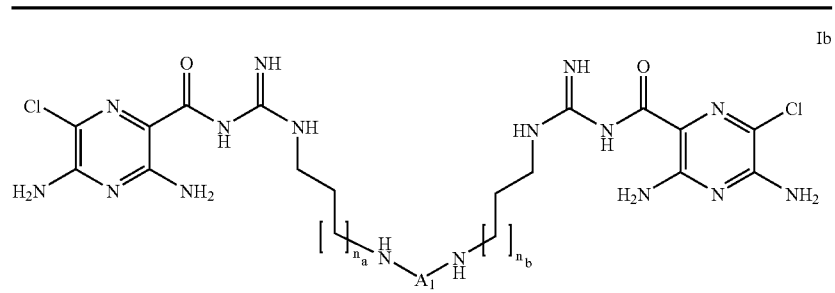
Ib
$n_a$ and $n_b$ are independantly = 1-3
| Ex. | $A_1$ | Viable Preparation Routes | $n_a$ | $n_b$ |
|---|---|---|---|---|
| 346 | (1,4-diacetamido-tetrahydronaphthalene) | 4 or 8d | 3 | 3 |
| 347 | (2,7-diacetamido-biphenylene) | 4 or 8d | 1 | 1 |
| 348 | (2,7-diacetamido-biphenylene) | 4 or 8d | 1 | 2 |
| 349 | (2,7-diacetamido-biphenylene) | 4 or 8d | 1 | 3 |
| 350 | (2,7-diacetamido-biphenylene) | 4 or 8d | 2 | 2 |
| 351 | (2,7-diacetamido-biphenylene) | 4 or 8d | 2 | 3 |

TABLE 3-continued
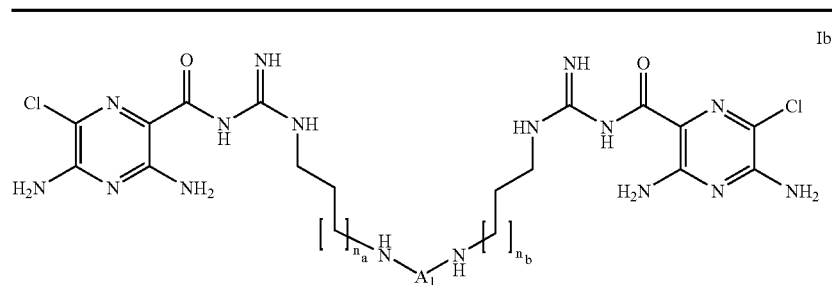
$n_a$ and $n_b$ are independantly = 1-3
| Ex. | A₁ | Viable Preparation Routes | $n_a$ | $n_b$ |
|---|---|---|---|---|
| 352 | | 4 or 8d | 3 | 3 |
| 353 | | 4 or 8d | 1 | 1 |
| 354 | | 4 or 8d | 1 | 2 |
| 355 | | 4 or 8d | 1 | 3 |
| 356 | | 4 or 8d | 2 | 2 |

TABLE 3-continued
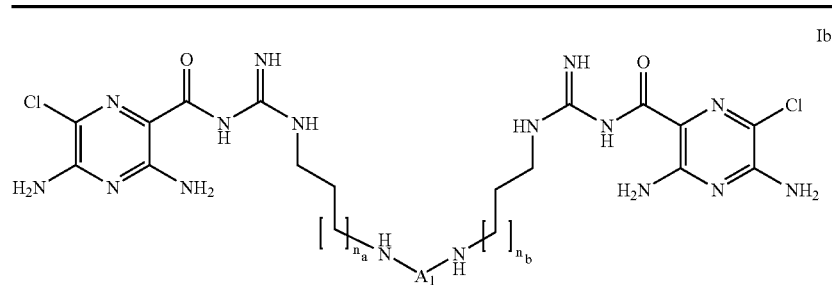
$n_a$ and $n_b$ are independantly = 1-3
| Ex. | A₁ | Viable Preparation Routes | $n_a$ | $n_b$ |
|---|---|---|---|---|
| 357 | (3,6-diacetamidopyridazine) | 4 or 8d | 2 | 3 |
| 359 | (3,6-diacetamidopyridazine) | 4 or 8d | 3 | 3 |
| 360 | (3,4-diacetamidofurazan) | 4 or 8d | 1 | 1 |
| 361 | (3,4-diacetamidofurazan) | 4 or 8d | 1 | 2 |
| 362 | (3,4-diacetamidofurazan) | 4 or 8d | 1 | 3 |

TABLE 3-continued
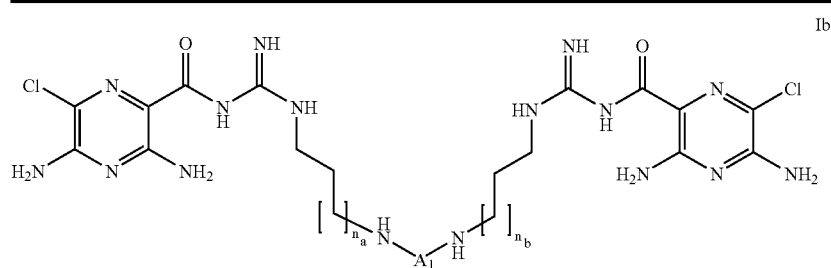
$n_a$ and $n_b$ are independantly = 1-3
| Ex. | A₁ | Viable Preparation Routes | $n_a$ | $n_b$ |
|---|---|---|---|---|
| 364 | | 4 or 8d | 2 | 2 |
| 365 | | 4 or 8d | 2 | 3 |
| 366 | | 4 or 8d | 3 | 3 |
| 367 | | 4 or 8d | 1 | 1 |
| 368 | | 4 or 8d | 1 | 2 |
| 369 | | 4 or 8d | 1 | 3 |

TABLE 3-continued
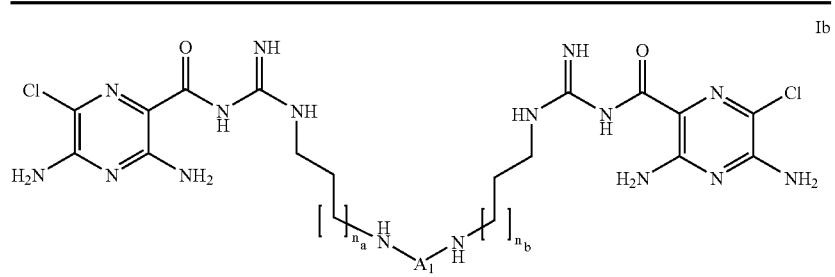
$n_a$ and $n_b$ are independantly = 1-3
| Ex. | A₁ | Viable Preparation Routes | $n_a$ | $n_b$ |
|---|---|---|---|---|
| 370 | | 4 or 8d | 2 | 2 |
| 371 | | 4 or 8d | 2 | 3 |
| 372 | | 4 or 8d | 3 | 3 |
| 373 | | 4 or 8d | 1 | 1 |
| 374 | | 4 or 8d | 1 | 2 |
| 375 | | 4 or 8d | 1 | 3 |

TABLE 3-continued
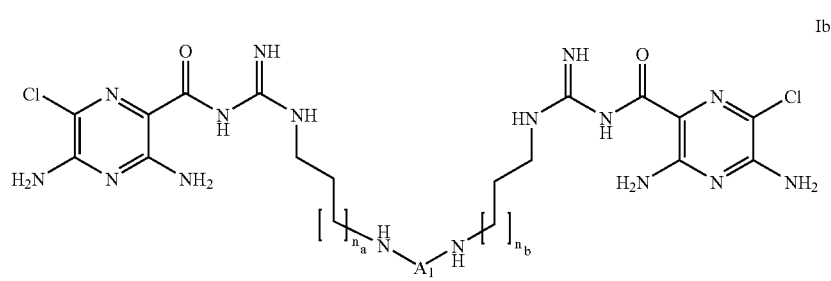
Ib
$n_a$ and $n_b$ are independantly = 1-3
| Ex. | $A_1$ | Viable Preparation Routes | $n_a$ | $n_b$ |
|---|---|---|---|---|
| 376 | | 4 or 8d | 2 | 2 |
| 377 | | 4 or 8d | 2 | 3 |
| 378 | | 4 or 8d | 3 | 3 |
| 379 | | 4 or 8d | 1 | 1 |
| 380 | | 4 or 8d | 1 | 2 |

TABLE 3-continued
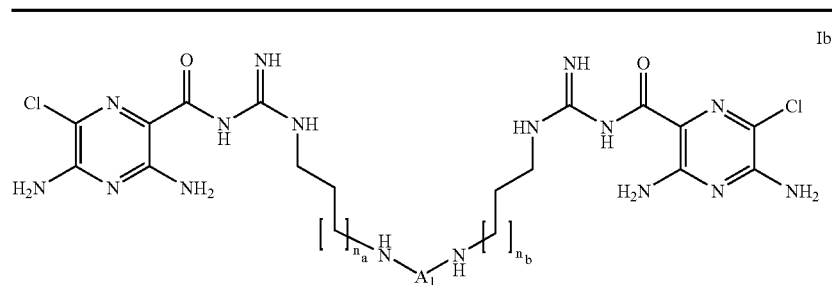
$n_a$ and $n_b$ are independantly = 1-3
| Ex. | $A_1$ | Viable Preparation Routes | $n_a$ | $n_b$ |
|---|---|---|---|---|
| 381 | | 4 or 8d | 1 | 3 |
| 382 | | 4 or 8d | 2 | 2 |
| 383 | | 4 or 8d | 2 | 3 |
| 384 | | 4 or 8d | 3 | 3 |
| 385 | | 4 or 8d | 1 | 1 |

TABLE 3-continued
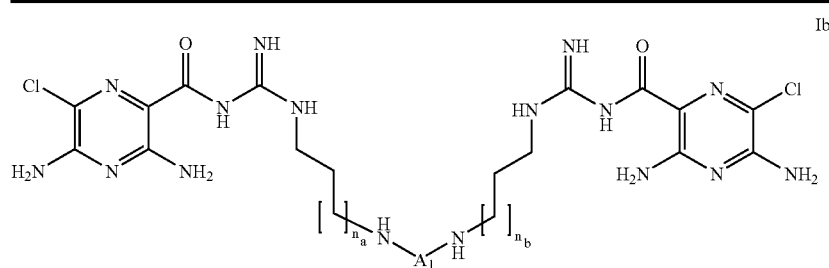
$n_a$ and $n_b$ are independantly = 1-3
| Ex. | $A_1$ | Viable Preparation Routes | $n_a$ | $n_b$ |
|---|---|---|---|---|
| 386 | | 4 or 8d | 1 | 2 |
| 387 | | 4 or 8d | 1 | 3 |
| 388 | | 4 or 8d | 2 | 2 |
| 389 | | 4 or 8d | 2 | 3 |
| 390 | | 4 or 8d | 3 | 3 |
| 391 | | 4 or 8d | 1 | 1 |
| 392 | | 4 or 8d | 1 | 2 |
| 393 | | 4 or 8d | 1 | 3 |

TABLE 3-continued
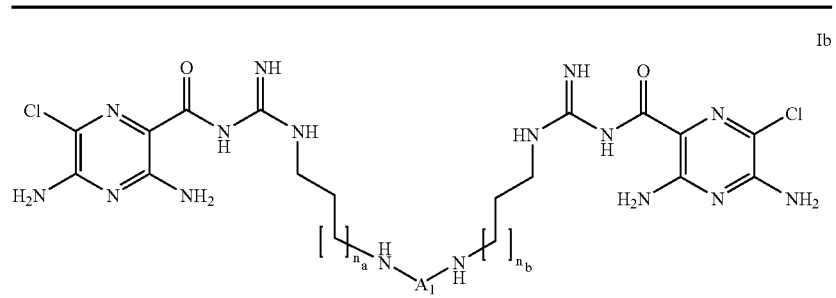
$n_a$ and $n_b$ are independantly = 1-3
| Ex. | A₁ | Viable Preparation Routes | $n_a$ | $n_b$ |
|---|---|---|---|---|
| 394 | | 4 or 8d | 2 | 2 |
| 395 | | 4 or 8d | 2 | 3 |
| 396 | | 4 or 8d | 3 | 3 |
| 397 | | 4 or 8d | 1 | 1 |
| 398 | | 4 or 8d | 1 | 2 |
| 399 | | 4 or 8d | 1 | 3 |

TABLE 3-continued
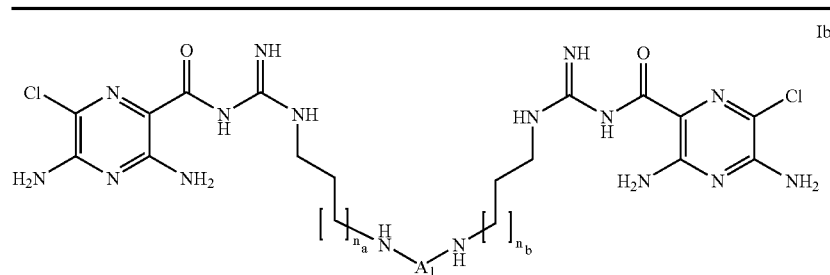
$n_a$ and $n_b$ are independantly = 1-3
| Ex. | A₁ | Viable Preparation Routes | $n_a$ | $n_b$ |
|---|---|---|---|---|
| 400 | | 4 or 8d | 2 | 2 |
| 401 | | 4 or 8d | 2 | 3 |
| 402 | | 4 or 8d | 3 | 3 |
| 403 | | 4 or 8d | 1 | 1 |
| 404 | | 4 or 8d | 1 | 2 |
| 405 | | 4 or 8d | 1 | 3 |
| 406 | | 4 or 8d | 2 | 2 |

TABLE 3-continued
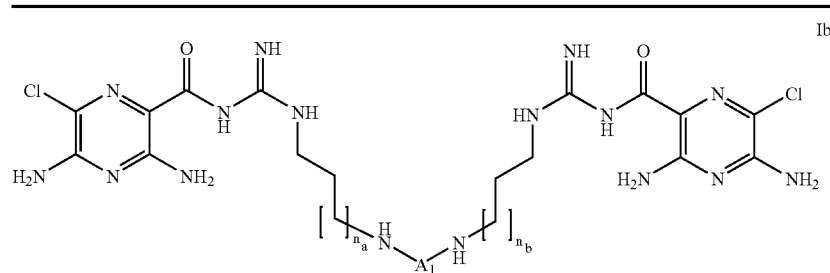
$n_a$ and $n_b$ are independantly = 1-3
| Ex. | A₁ | Viable Preparation Routes | $n_a$ | $n_b$ |
|---|---|---|---|---|
| 407 | | 4 or 8d | 2 | 3 |
| 408 | | 4 or 8d | 3 | 3 |
| 409 | | 4 or 8d | 1 | 1 |
| 410 | | 4 or 8d | 1 | 2 |
| 411 | | 4 or 8d | 1 | 3 |
| 412 | | 4 or 8d | 2 | 2 |
| 413 | | 4 or 8d | 2 | 3 |

TABLE 3-continued
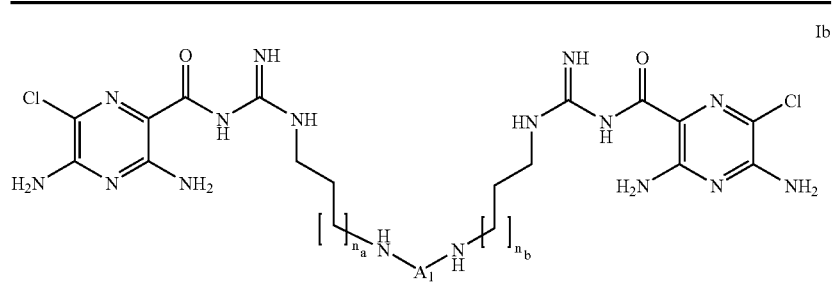
$n_a$ and $n_b$ are independantly = 1-3
| Ex. | $A_1$ | Viable Preparation Routes | $n_a$ | $n_b$ |
|---|---|---|---|---|
| 414 | (3,5-diacetamidopyridine) | 4 or 8d | 3 | 3 |
| 415 | (2,6-diacetamidopyridine) | 4 or 8d | 1 | 1 |
| 416 | (2,6-diacetamidopyridine) | 4 or 8d | 1 | 2 |
| 417 | (2,6-diacetamidopyridine) | 4 or 8d | 1 | 3 |
| 418 | (2,6-diacetamidopyridine) | 4 or 8d | 2 | 2 |
| 419 | (2,6-diacetamidopyridine) | 4 or 8d | 2 | 3 |

TABLE 3-continued
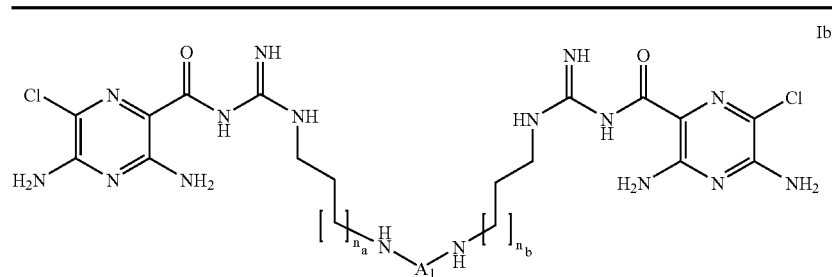
Ib
$n_a$ and $n_b$ are independantly = 1-3
| Ex. | A₁ | Viable Preparation Routes | $n_a$ | $n_b$ |
|---|---|---|---|---|
| 420 | | 4 or 8d | 3 | 3 |
| 421 | | 4 or 8d | 1 | 1 |
| 422 | | 4 or 8d | 1 | 2 |
| 423 | | 4 or 8d | 1 | 3 |
| 423 | | 4 or 8d | 2 | 2 |
| 425 | | 4 or 8d | 2 | 3 |

TABLE 3-continued $n_a$ and $n_b$ are independantly = 1-3

| Ex. | $A_1$ | Viable Preparation Routes | $n_a$ | $n_b$ |
|---|---|---|---|---|
| 426 | (1,1-cyclopentyl bis(methylacetamide)) | 4 or 8d | 3 | 3 |
| 427 | (piperazine bis(methylacetamide)) | 4 or 8d | 1 | 1 |
| 428 | (piperazine bis(methylacetamide)) | 4 or 8d | 1 | 2 |
| 429 | (piperazine bis(methylacetamide)) | 4 or 8d | 1 | 3 |
| 430 | (piperazine bis(methylacetamide)) | 4 or 8d | 2 | 2 |
| 431 | (piperazine bis(methylacetamide)) | 4 or 8d | 2 | 3 |
| 432 | (piperazine bis(methylacetamide)) | 4 or 8d | 3 | 3 |
| 433 | (1,1-cyclohexyl bis(methylacetamide)) | 4 or 8d | 1 | 1 |

TABLE 3-continued
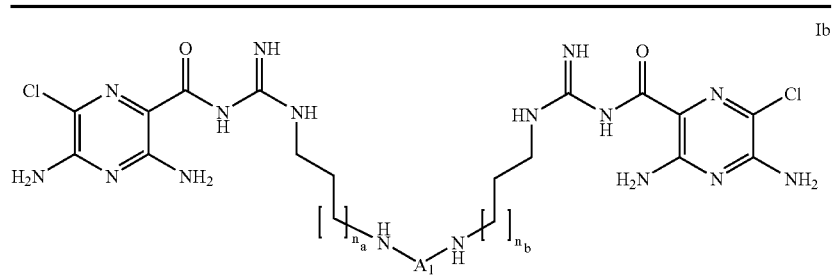
$n_a$ and $n_b$ are independantly = 1-3
| Ex. | A₁ | Viable Preparation Routes | $n_a$ | $n_b$ |
|---|---|---|---|---|
| 434 | | 4 or 8d | 1 | 2 |
| 435 | | 4 or 8d | 1 | 3 |
| 436 | | 4 or 8d | 2 | 2 |
| 437 | | 4 or 8d | 2 | 3 |
| 438 | | 4 or 8d | 3 | 3 |
| 439 | | 5 or 8e | 1 | 1 |

TABLE 3-continued
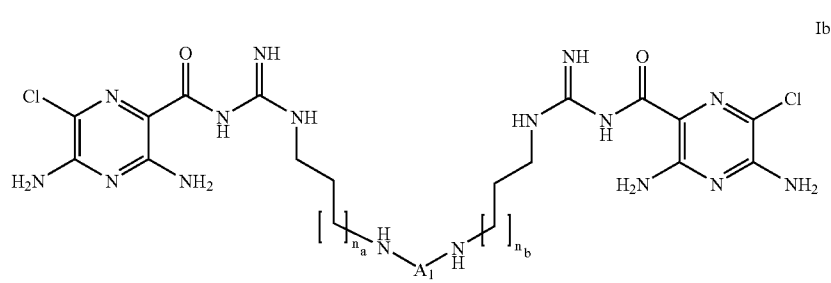
Ib
$n_a$ and $n_b$ are independantly = 1-3
| Ex. | A₁ | Viable Preparation Routes | $n_a$ | $n_b$ |
|---|---|---|---|---|
| 440 | | 5 or 8e | 1 | 2 |
| 441 | | 5 or 8e | 1 | 3 |
| 442 | | 5 or 8e | 2 | 2 |
| 443 | | 5 or 8e | 2 | 3 |
| 444 | | 5 or 8e | 3 | 3 |
| 445 | | 5 or 8e | 1 | 1 |
| 446 | | 5 or 8e | 1 | 2 |

TABLE 3-continued
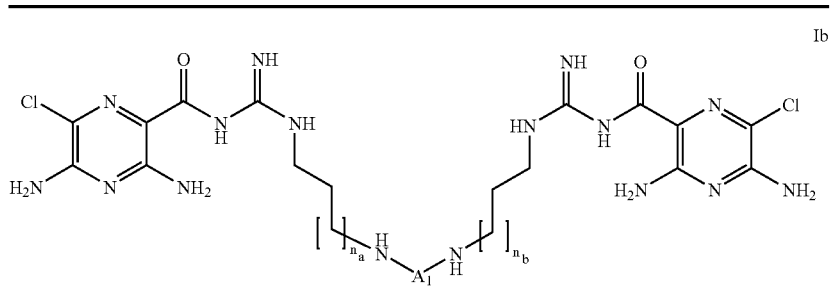
$n_a$ and $n_b$ are independantly = 1-3
| Ex. | $A_1$ | Viable Preparation Routes | $n_a$ | $n_b$ |
|---|---|---|---|---|
| 447 | ![structure] | 5 or 8e | 1 | 3 |
| 448 | ![structure] | 5 or 8e | 2 | 2 |
| 449 | ![structure] | 5 or 8e | 2 | 3 |
| 450 | ![structure] | 5 or 8e | 3 | 3 |
| 451 | ![structure] | 5 or 8e | 1 | 1 |

TABLE 3-continued
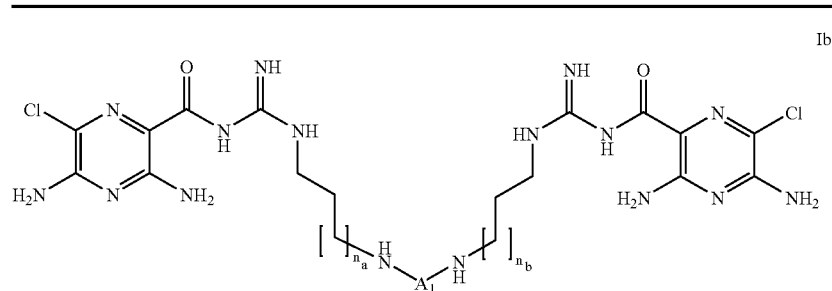
Ib
$n_a$ and $n_b$ are independantly = 1-3
| Ex. | A₁ | Viable Preparation Routes | $n_a$ | $n_b$ |
|---|---|---|---|---|
| 452 | | 5 or 8e | 1 | 2 |
| 453 | | 5 or 8e | 1 | 3 |
| 454 | | 5 or 8e | 2 | 2 |
| 455 | | 5 or 8e | 2 | 3 |
| 456 | | 5 or 8e | 3 | 3 |

TABLE 3-continued
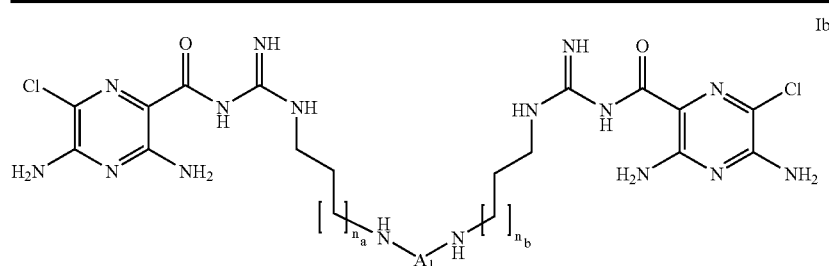
$n_a$ and $n_b$ are independantly = 1-3
| Ex. | A₁ | Viable Preparation Routes | $n_a$ | $n_b$ |
|---|---|---|---|---|
| 457 | piperazine-1,4-diyl bis(acetyl) | 5 or 8e | 1 | 1 |
| 459 | piperazine-1,4-diyl bis(acetyl) | 5 or 8e | 1 | 2 |
| 460 | piperazine-1,4-diyl bis(acetyl) | 5 or 8e | 1 | 3 |
| 461 | piperazine-1,4-diyl bis(acetyl) | 5 or 8e | 2 | 2 |
| 462 | piperazine-1,4-diyl bis(acetyl) | 5 or 8e | 2 | 3 |
| 463 | piperazine-1,4-diyl bis(acetyl) | 5 or 8e | 3 | 3 |

TABLE 3-continued
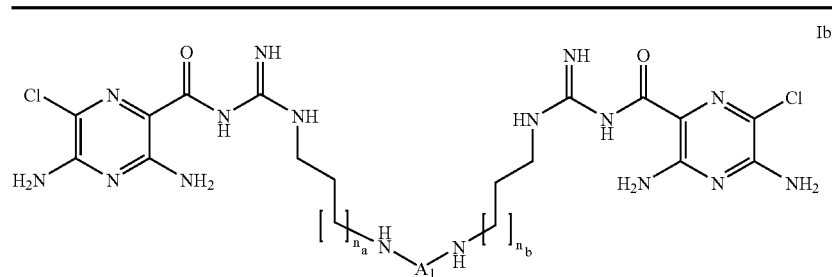
$n_a$ and $n_b$ are independantly = 1-3
| Ex. | A₁ | Viable Preparation Routes | $n_a$ | $n_b$ |
|---|---|---|---|---|
| 464 | | 6 or 8f | 1 | 1 |
| 465 | | 6 or 8f | 1 | 2 |
| 466 | | 6 or 8f | 1 | 3 |
| 467 | | 6 or 8f | 2 | 2 |
| 468 | | 6 or 8f | 2 | 3 |
| 469 | | 6 or 8f | 3 | 3 |
| 470 | | 6 or 8f | 1 | 1 |
| 471 | | 6 or 8f | 1 | 2 |

TABLE 3-continued
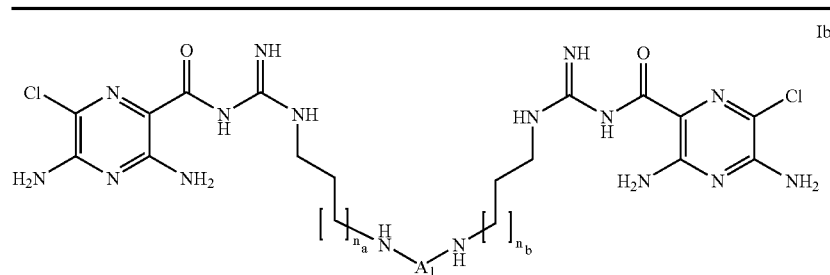
$n_a$ and $n_b$ are independantly = 1-3
| Ex. | A₁ | Viable Preparation Routes | $n_a$ | $n_b$ |
|---|---|---|---|---|
| 472 | | 6 or 8f | 1 | 3 |
| 473 | | 6 or 8f | 2 | 2 |
| 474 | | 6 or 8f | 2 | 3 |
| 475 | | 6 or 8f | 3 | 3 |
| 476 | | 6 or 8f | 1 | 1 |
| 477 | | 6 or 8f | 1 | 2 |
| 478 | | 6 or 8f | 1 | 3 |
| 479 | | 6 or 8f | 2 | 2 |
| 480 | | 6 or 8f | 2 | 3 |

TABLE 3-continued
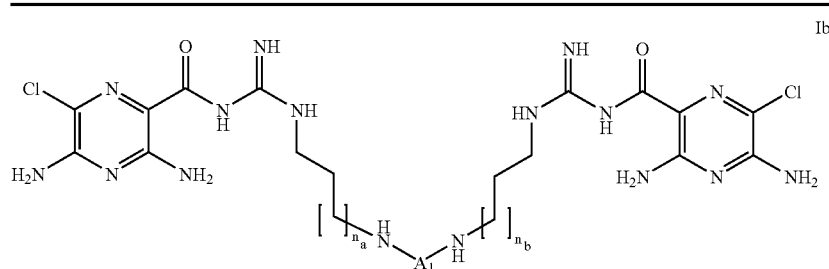
$n_a$ and $n_b$ are independantly = 1-3
| Ex. | A₁ | Viable Preparation Routes | $n_a$ | $n_b$ |
|---|---|---|---|---|
| 481 | | 6 or 8f | 3 | 3 |
| 482 | | 6 or 8f | 1 | 1 |
| 483 | | 6 or 8f | 1 | 2 |
| 484 | | 6 or 8f | 1 | 3 |
| 485 | | 6 or 8f | 2 | 2 |
| 486 | | 6 or 8f | 2 | 3 |
| 487 | | 6 or 8f | 3 | 3 |
| 488 | | 6 or 8f | 1 | 1 |
| 489 | | 6 or 8f | 1 | 2 |
| 490 | | 6 or 8f | 1 | 3 |

TABLE 3-continued
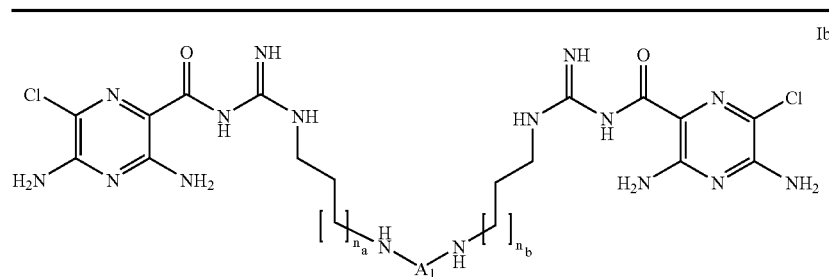
$n_a$ and $n_b$ are independantly = 1-3
| Ex. | A₁ | Viable Preparation Routes | $n_a$ | $n_b$ |
|---|---|---|---|---|
| 491 | 3,4-dimethylthiophene | 6 or 8f | 2 | 2 |
| 492 | 3,4-dimethylthiophene | 6 or 8f | 2 | 3 |
| 493 | 3,4-dimethylthiophene | 6 or 8f | 3 | 3 |
| 494 | 1,5-bis(methylsulfonyl)naphthalene | 7 or 8g | 1 | 1 |
| 495 | 1,5-bis(methylsulfonyl)naphthalene | 7 or 8g | 1 | 2 |
| 496 | 1,5-bis(methylsulfonyl)naphthalene | 7 or 8g | 1 | 3 |

TABLE 3-continued
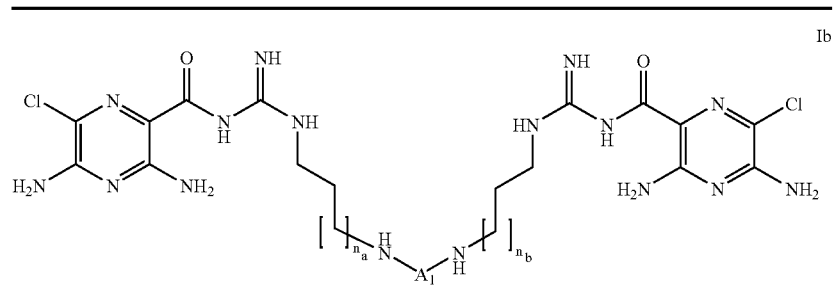
$n_a$ and $n_b$ are independantly = 1-3
| Ex. | A₁ | Viable Preparation Routes | $n_a$ | $n_b$ |
|---|---|---|---|---|
| 497 | 1,5-naphthalene bis(methylsulfonyl) | 7 or 8g | 2 | 2 |
| 498 | 1,5-naphthalene bis(methylsulfonyl) | 7 or 8g | 2 | 3 |
| 499 | 1,5-naphthalene bis(methylsulfonyl) | 7 or 8g | 3 | 3 |
| 500 | 1,3-phenylene bis(methylsulfonyl) | 7 or 8g | 1 | 1 |
| 501 | 1,3-phenylene bis(methylsulfonyl) | 7 or 8g | 1 | 2 |

TABLE 3-continued $n_a$ and $n_b$ are independantly = 1-3

| Ex. | A$_1$ | Viable Preparation Routes | $n_a$ | $n_b$ |
|---|---|---|---|---|
| 502 | 1,3-bis(methylsulfonyl)benzene | 7 or 8g | 1 | 3 |
| 503 | 1,3-bis(methylsulfonyl)benzene | 7 or 8g | 2 | 2 |
| 504 | 1,3-bis(methylsulfonyl)benzene | 7 or 8g | 2 | 3 |
| 505 | 1,3-bis(methylsulfonyl)benzene | 7 or 8g | 3 | 3 |
| 506 | 1,3-bis(methylsulfonyl)propane | 7 or 8g | 1 | 1 |
| 507 | 1,3-bis(methylsulfonyl)propane | 7 or 8g | 1 | 2 |
| 508 | 1,3-bis(methylsulfonyl)propane | 7 or 8g | 1 | 3 |
| 509 | 1,3-bis(methylsulfonyl)propane | 7 or 8g | 2 | 2 |
| 510 | 1,3-bis(methylsulfonyl)propane | 7 or 8g | 2 | 3 |

TABLE 3-continued
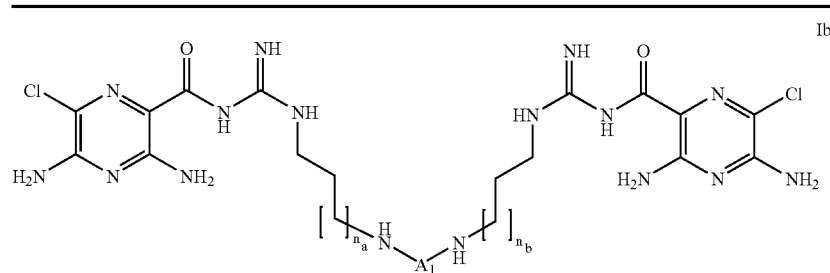
$n_a$ and $n_b$ are independantly = 1-3
| Ex. | A₁ | Viable Preparation Routes | $n_a$ | $n_b$ |
|---|---|---|---|---|
| 511 | | 7 or 8g | 3 | 3 |
| 512 | | 7 or 8g | 1 | 1 |
| 513 | | 7 or 8g | 1 | 2 |
| 514 | | 7 or 8g | 1 | 3 |
| 515 | | 7 or 8g | 2 | 2 |
| 516 | | 7 or 8g | 2 | 3 |
| 517 | | 7 or 8g | 3 | 3 |
| 518 | | 7 or 8g | 1 | 1 |
| 519 | | 7 or 8g | 1 | 2 |

TABLE 3-continued
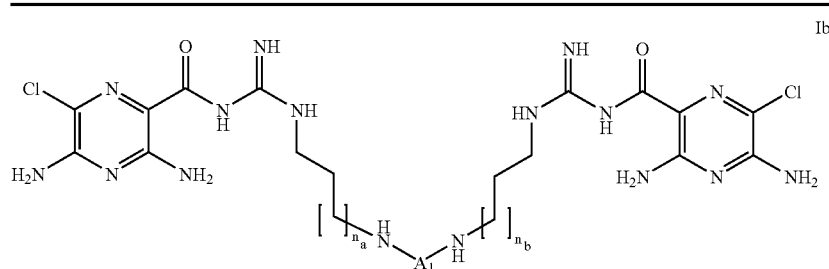
$n_a$ and $n_b$ are independantly = 1-3
| Ex. | $A_1$ | Viable Preparation Routes | $n_a$ | $n_b$ |
|---|---|---|---|---|
| 520 | 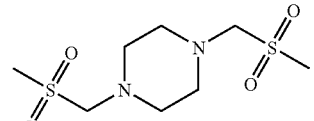 | 7 or 8g | 1 | 3 |
| 521 | 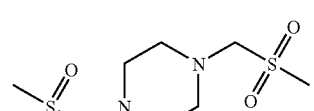 | 7 or 8g | 2 | 2 |
| 522 | 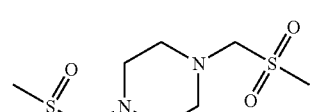 | 7 or 8g | 2 | 3 |
| 523 | 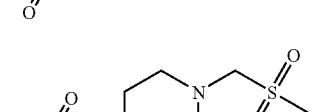 | 7 or 8g | 3 | 3 |
Yet further preferred compounds of the present invention are shown in Table 4 below. The method of preparation being described thereinafter.
TABLE 4
| Ex. | Structure | Viable Preparation Routes |
|---|---|---|
| 524 | 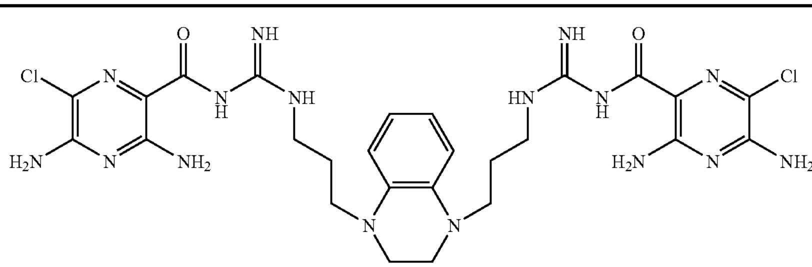 | 6 or 8f |

| Ex. | Structure | Viable Preparation Routes |
|---|---|---|
| 525 | 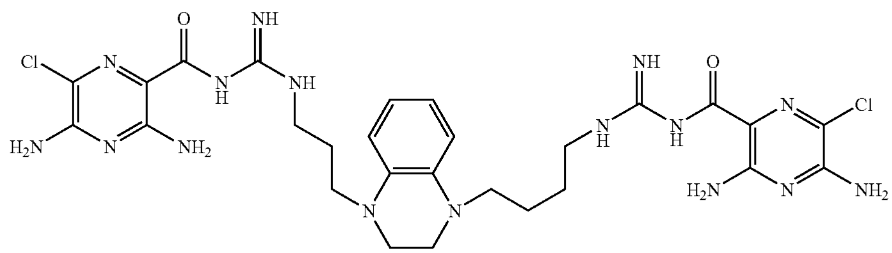 | 6 or 8f |
| 526 | 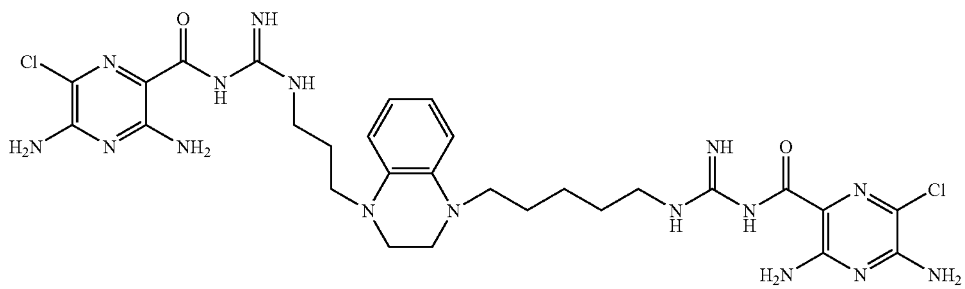 | 6 or 8f |
| 527 | 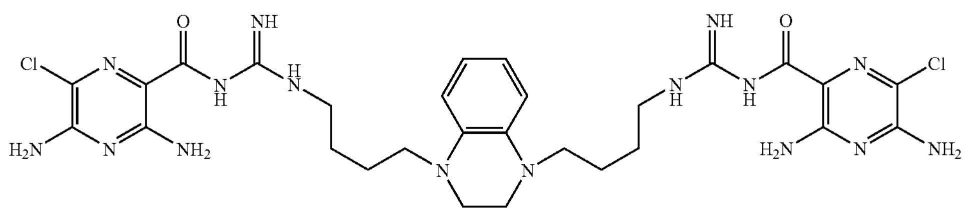 | 6 or 8f |
| 528 | 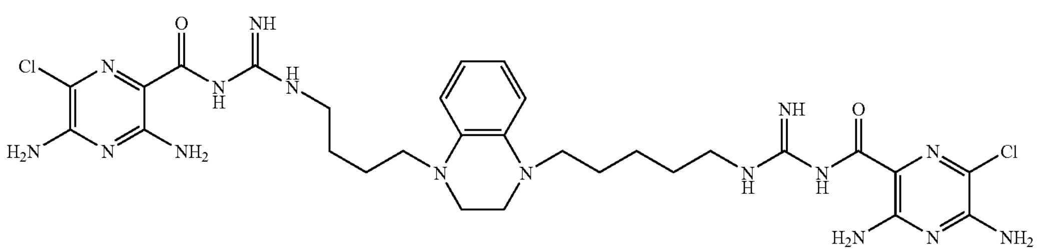 | 6 or 8f |
| 529 | 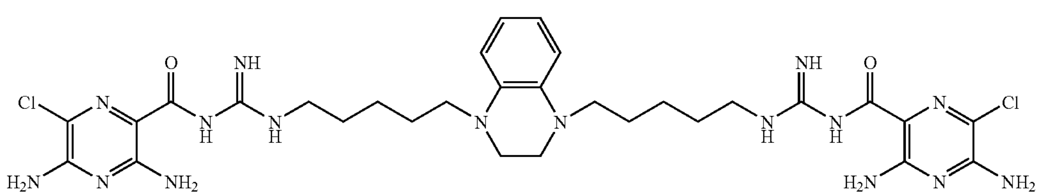 | 6 or 8f |
| 530 | 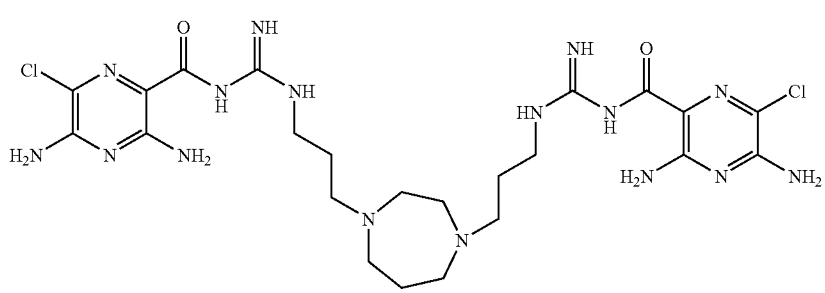 | 6 or 8f |

TABLE 4-continued

| Ex. | Structure | Viable Preparation Routes |
|---|---|---|
| 531 | 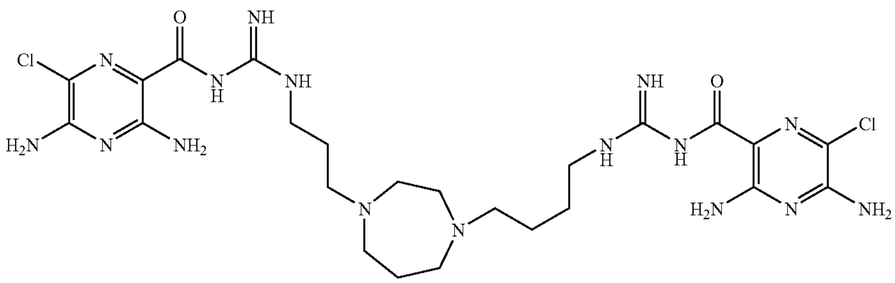 | 6 or 8f |
| 532 | 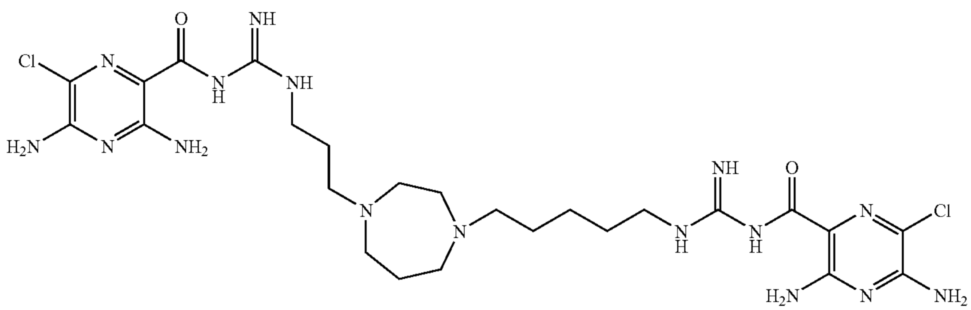 | 6 or 8f |
| 533 | 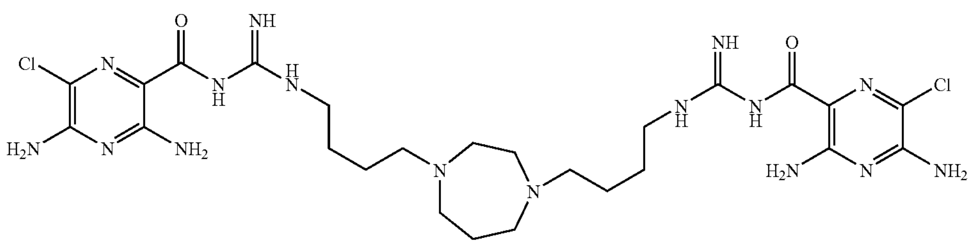 | 6 or 8f |
| 534 | 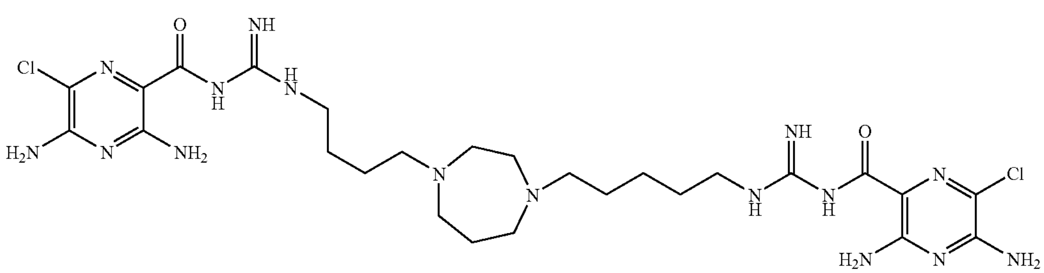 | 6 or 8f |
| 535 | 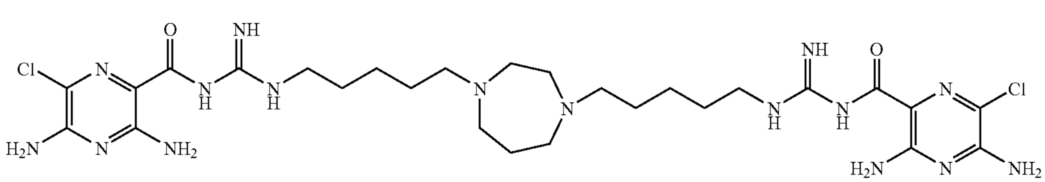 | 6 or 8f |

TABLE 4-continued

| Ex. | Structure | Viable Preparation Routes |
|---|---|---|
| 536 | 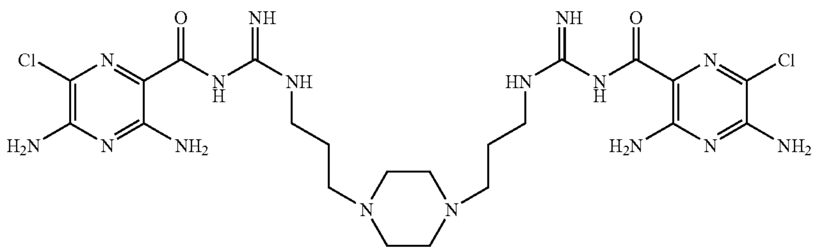 | 6 or 8f |
| 537 | 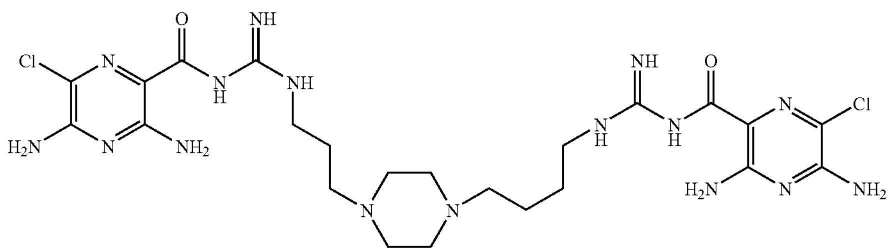 | 6 or 8f |
| 538 | 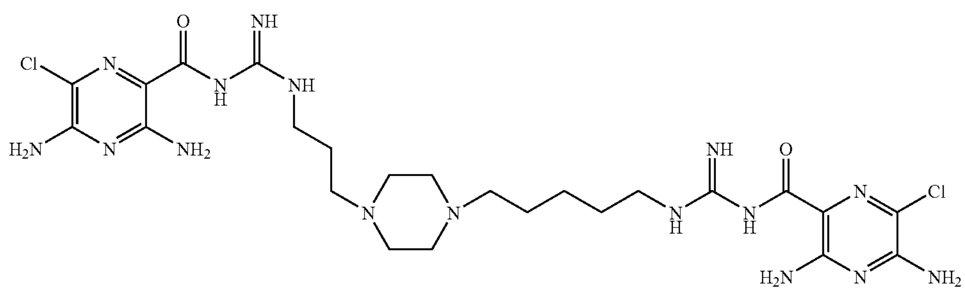 | 6 or 8f |
| 539 | 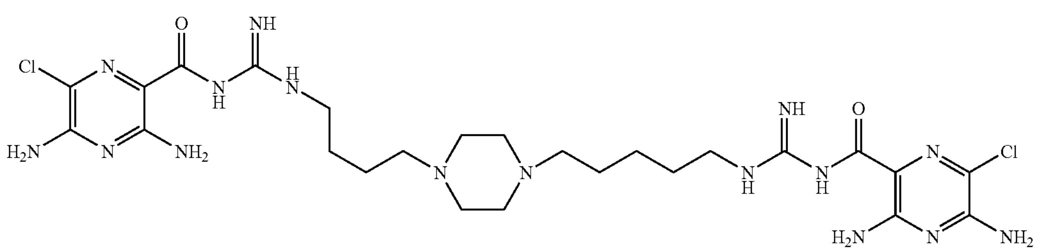 | 6 or 8f |
| 540 | 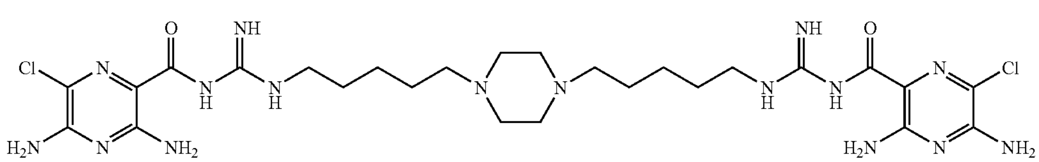 | 6 or 8f |

Yet further preferred compounds of the present invention include compounds of formula (Ic) and are as shown in Table 5 below. The method of preparation being described hereinafter.

TABLE 5
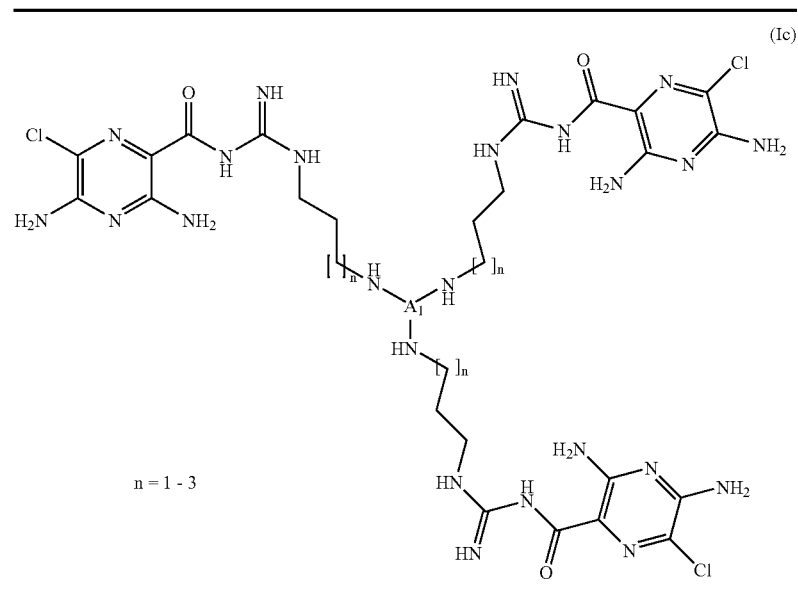
n = 1 - 3
| Ex. | A₁ | Viable Preparation Route | $n_a$ | $n_b$ | $n_c$ |
|---|---|---|---|---|---|
| 541 | 1,3,5-triacetylbenzene | 1 or 2 or 8a | 1 | 1 | 1 |
| 542 | 1,3,5-triacetylbenzene | 1 or 2 or 8a | 1 | 1 | 2 |
| 543 | 1,3,5-triacetylbenzene | 1 or 2 or 8a | 1 | 1 | 3 |
| 544 | 1,3,5-triacetylbenzene | 1 or 2 or 8a | 1 | 2 | 2 |

TABLE 5-continued
| 545 | 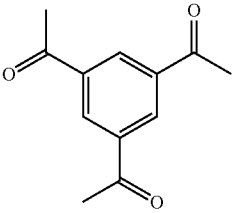 | 1 or 2 or 8a | 1 | 2 | 3 |
| 546 | 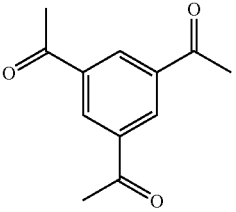 | 1 or 2 or 8a | 1 | 3 | 3 |
| 547 | 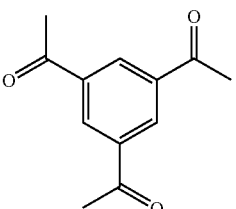 | 1 or 2 or 8a | 2 | 2 | 2 |
| 548 | 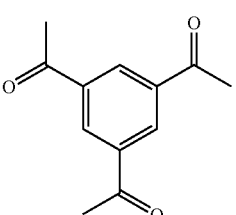 | 1 or 2 or 8a | 2 | 2 | 3 |
| 549 | 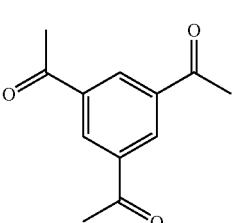 | 1 or 2 or 8a | 2 | 3 | 3 |
| 55 | 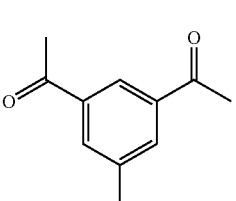 | 1 or 2 or 8a | 3 | 3 | 3 |
| 551 | 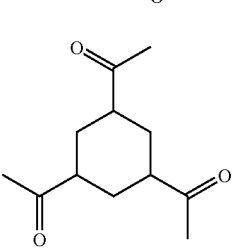 | 2 or 8b | 1 | 1 | 1 |

TABLE 5-continued

| | | | | | |
|---|---|---|---|---|---|
| 552 | (structure) | 2 or 8b | 1 | 1 | 2 |
| 553 | (structure) | 2 or 8b | 1 | 1 | 3 |
| 554 | (structure) | 2 or 8b | 1 | 2 | 2 |
| 555 | (structure) | 2 or 8b | 1 | 2 | 3 |
| 556 | (structure) | 2 or 8b | 1 | 3 | 3 |
| 557 | (structure) | 2 or 8b | 2 | 2 | 2 |
| 558 | (structure) | 2 or 8b | 2 | 2 | 3 |

TABLE 5-continued

| | | | | | |
|---|---|---|---|---|---|
| 559 | (1,3,5-triacetylcyclohexane structure) | 2 or 8b | 2 | 3 | 3 |
| 560 | (1,3,5-triacetylcyclohexane structure) | 2 or 8b | 3 | 3 | 3 |
| 561 | (1,3,5-triacetylcyclohexane structure) | 2 or 8b | 1 | 1 | 1 |
| 562 | (1,3,5-triacetylcyclohexane structure) | 2 or 8b | 1 | 1 | 2 |
| 563 | (1,3,5-triacetylcyclohexane structure) | 2 or 8b | 1 | 1 | 3 |
| 564 | (1,3,5-triacetylcyclohexane structure) | 2 or 8b | 1 | 2 | 2 |
| 565 | (1,3,5-triacetylcyclohexane structure) | 2 or 8b | 1 | 2 | 3 |

TABLE 5-continued

| | | | | | |
|---|---|---|---|---|---|
| 566 | (1,3,5-triacetylcyclohexane) | 2 or 8b | 1 | 3 | 3 |
| 567 | (1,3,5-triacetylcyclohexane) | 2 or 8b | 2 | 2 | 2 |
| 568 | (1,3,5-triacetylcyclohexane) | 2 or 8b | 2 | 2 | 3 |
| 569 | (1,3,5-triacetylcyclohexane) | 2 or 8b | 2 | 3 | 3 |
| 570 | (1,3,5-triacetylcyclohexane) | 2 or 8b | 3 | 3 | 3 |
| 571 | (1,3,5-triacetamidocyclohexane) | 4 or 8d | 1 | 1 | 1 |

TABLE 5-continued
| 572 | 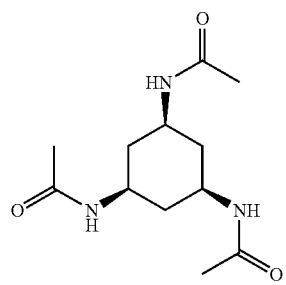 | 4 or 8d | 1 | 1 | 2 |
| 573 | 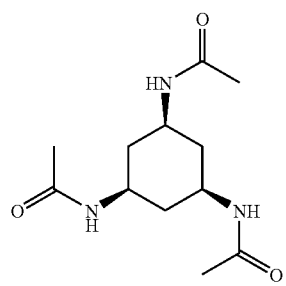 | 4 or 8d | 1 | 1 | 3 |
| 574 | 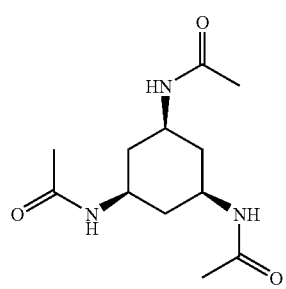 | 4 or 8d | 1 | 2 | 2 |
| 575 | 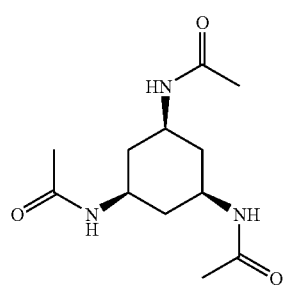 | 4 or 8d | 1 | 2 | 3 |

TABLE 5-continued
| | | | | | |
|---|---|---|---|---|---|
| 576 | 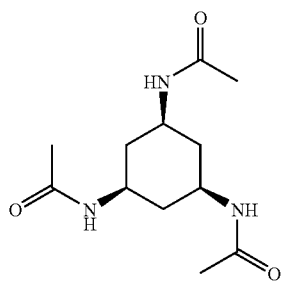 | 4 or 8d | 1 | 3 | 3 |
| 577 | 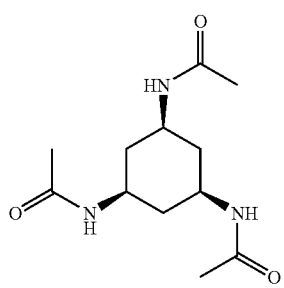 | 4 | 2 | 2 | 2 |
| 578 | 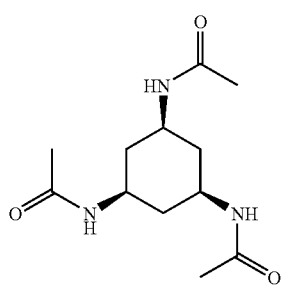 | 4 | 2 | 2 | 3 |
| 579 | 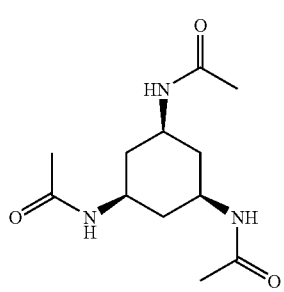 | 4 | 2 | 3 | 3 |
| 580 | 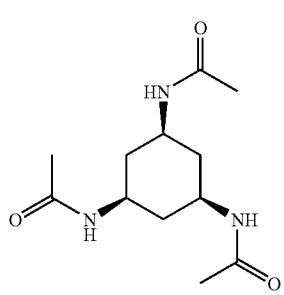 | 4 | 3 | 3 | 3 |

The examples shown in Tables 3-5 are prepared according to the schemes shown below:
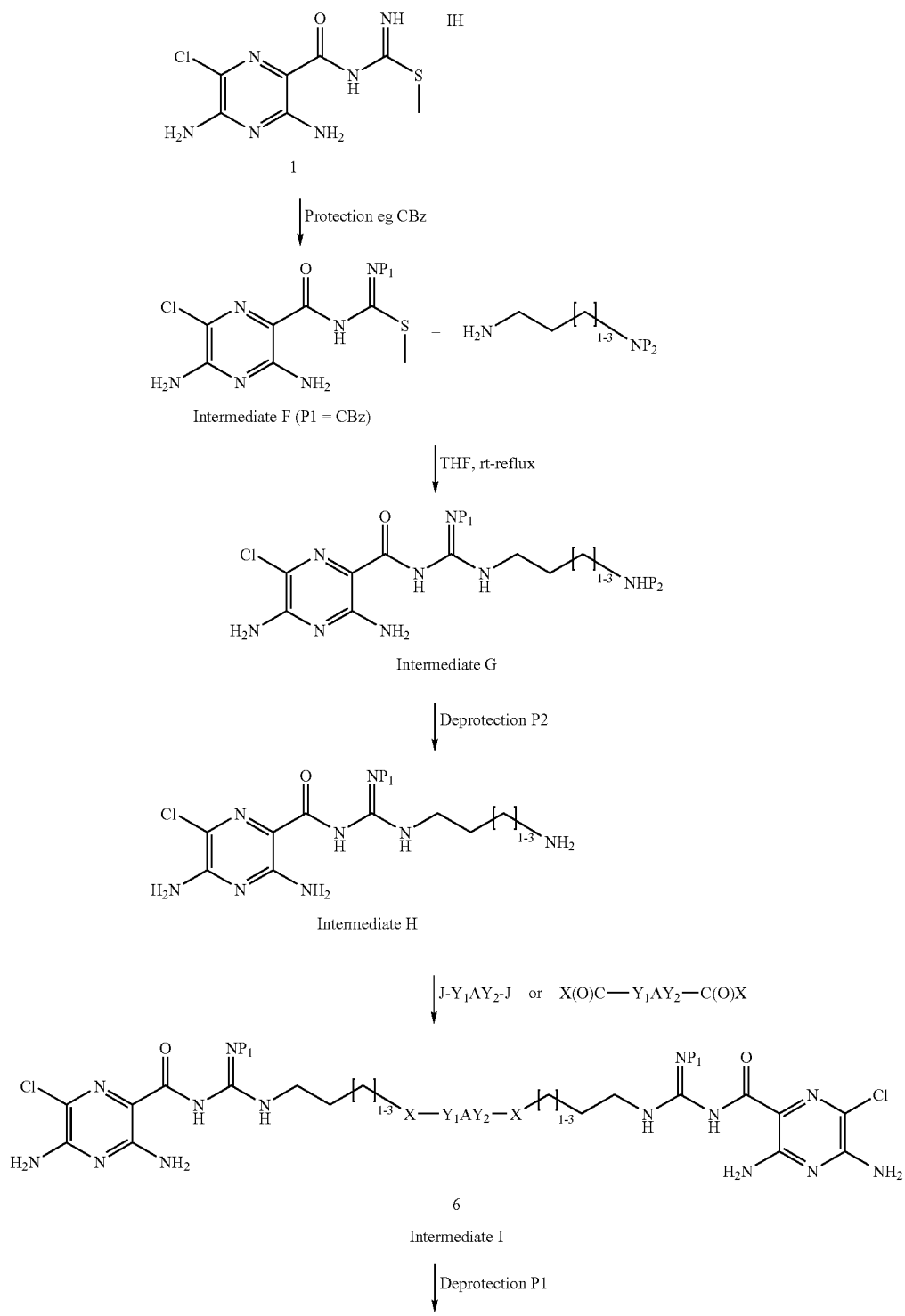

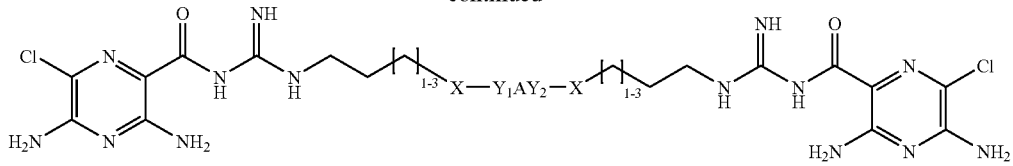

The preparations of the intermediates shown in the schemes are described in the Intermediates section.

$Y_1AY_2$ may be varied utilising mono protected diamines and the Intermediate 2. This is illustrated in the scheme above. Where $P_1$ and $P_2$ represent different standard amine protecting groups, e.g., Boc, CBz, acetate and deprotection is by standard means. Where J represents a group capable of reacting with amines, e.g., halogen, carboxylic acid, isocyanate, sulfonyl chlorides, aldehydes and ketones, methanesulfonate. X represents a halogen, OH, an ester or an activated ester species derived from the use of coupling agents, e.g., EDCl. Where these reagents are unavailable commercially they can be synthesized by general methods known in the art.

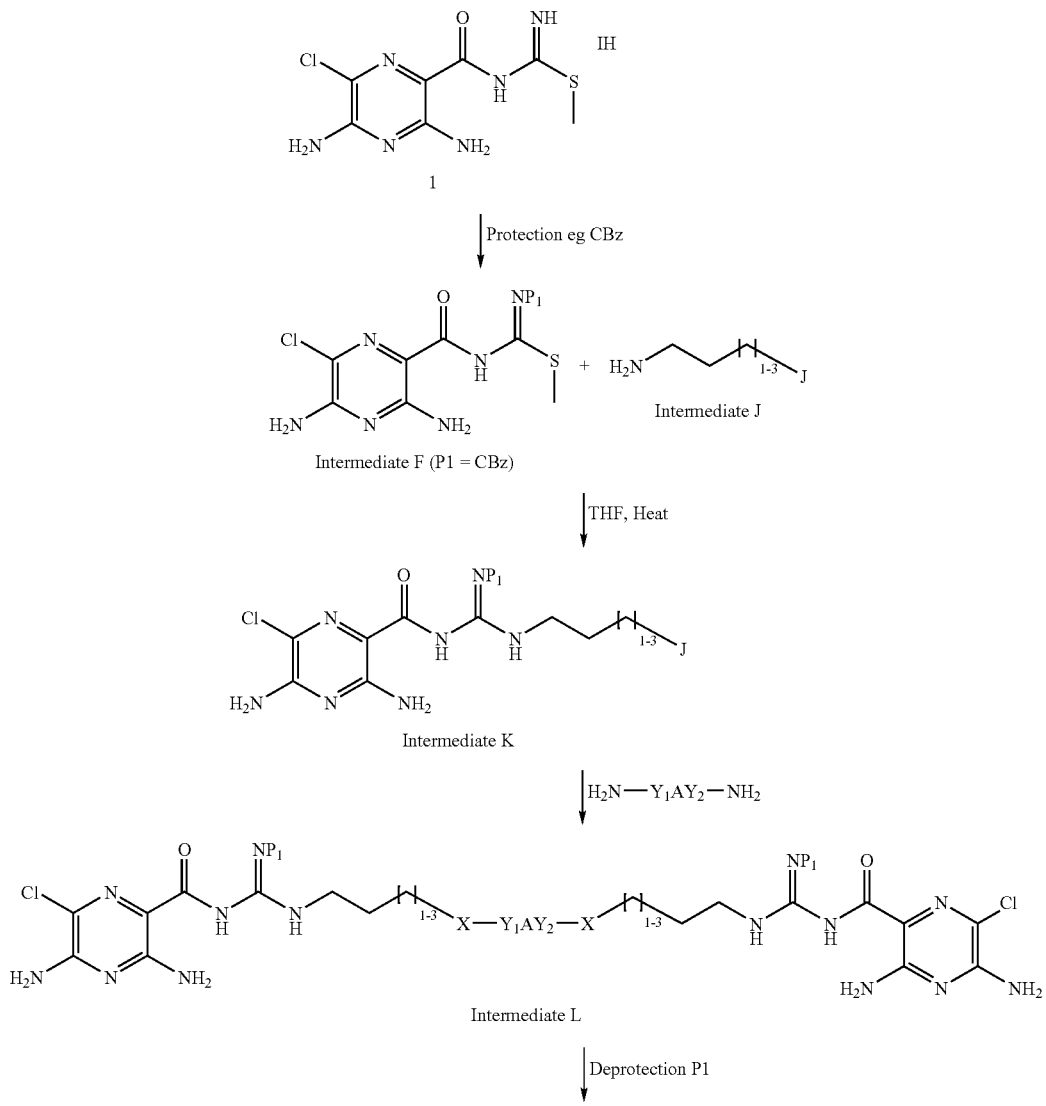

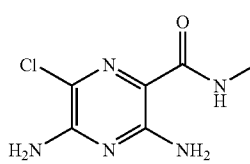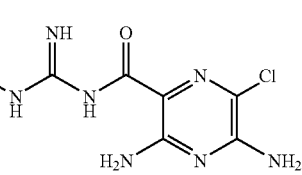

Y$_1$AY$_2$ may be varied utilizing monoamines and the Intermediate 2. J represents a group capable of reacting with amines, e.g., halogen, carboxylic acid.

The examples shown in Tables 3-5 are prepared according to Schemes 3 and 4 using the routes assigned in the table which are described hereinafter with the appropriate Intermediates G, H or K.

Route 1

The di-acid chloride or tri-acid chloride (1 eq) is added to a stirred solution of Intermediate H (2 eq) and Et$_3$N (3 eq) in DMF (10 vol). Upon completion of the reaction the solution is quenched with water and the product (Intermediate I) isolated by filtration.

Route 2

EDCl (1 eq) is added to a stirred solution of the di-acid or tri-acid (1 eq) in DMF (10 vol). N-Ethyl-morpholine (3 eq) and Intermediate G (2 eq) are added and the reaction heated. Upon completion the reaction is quenched with NaHCO$_3$ solution and the product (Intermediate I) isolated by filtration.

Route 3

The di-isocyanate (1 eq) is added to a stirred solution of Intermediate H (2 eq) and Et$_3$N (2.5 eq) in DCM (40 vol). The reaction is heated to reflux for 8 hours and the product (Intermediate I) isolated by filtration.

Route 4

Diphenylphosphorylazide (1 eq) is added to a stirred solution of the di-acid or tri-acid (1 eq) Et$_3$N (2 eq) and Intermediate H in DCM (40 vol). The reaction is heated to reflux for 8 hours. The product (Intermediate I) is isolated from the cooled reaction mixture by filtration.

Route 5

The diamine (1 eq) is added to a solution of bis-4-nitrophenyl carbonate (2 eq) in DMF. The reaction is left to stir for 1-2 hours and Intermediate H is added and the reaction heated. Upon completion the reaction is quenched with water and the crude product (Intermediate I) isolated by filtration and purified by flash column chromatography.

Route 6

Intermediate K (2 eq) is added to a stirring solution of the diamine (1 eq) and triethylaine (2 eq) in DMF. Upon completion the reaction is quenched with water and the product (Intermediate L) isolated by filtration or extraction with DCM.

Route 7

The di-sulfonyl chloride (1 eq) is added to a stirring solution of Intermediate H (2 eq) in DMF. Upon completion the reaction is quenched with water the product (Intermediate I) isolated by filtration.

Note: Sulfonyl chlorides may be obtained by methods known in the literature, e.g., *Org Synth*, coll Vol 1, p. 84 (1941) by reaction of sulfonic acids with a chlorinating agents, e.g., SOCl$_2$, PCl$_5$, POCl$_3$.

Examples of general methods for the deprotection of Intermediate I and Intermediate L to afford the Examples shown in Tables 3-5 are described in Methods 1 and 2:

Method 1

Intermediate I or Intermediate L (1 eq) is dissolved in 33% HBr/Acetic acid (50 vol) and heated at 50° C. for 8 hours. Upon cooling the product is isolated by filtration or by trituration with THF.

Method 2

Intermediate I or Intermediate L is suspended in DCM (20 vol) and TMSI (1.5 eq) added. The reaction was heated to 40° C. for 2-4 hours and then quenched at RT with MeOH. The solution was left to stir at RT for 2-3 hours and the resulting precipitate is filtered and dried under vacuum to produce the product.

Route 8

Alternatively, the compounds shown in Tables 36 may be synthesized analogously to Example 1 using the appropriate diamine. The diamines (Intermediates O) are prepared from Intermediates N which may be synthesized using standard methods known in the literature from mono-protected amines via Steps 1a-e, described hereinafter in the Intermediates section. Deprotection by standard methods and concomitant reaction with 1-(3,5-diamino-6-chloro-pyrazine-2-carbonyl)-2-methyl-isothiourea hydroiodide to produce compound P.

Route 8

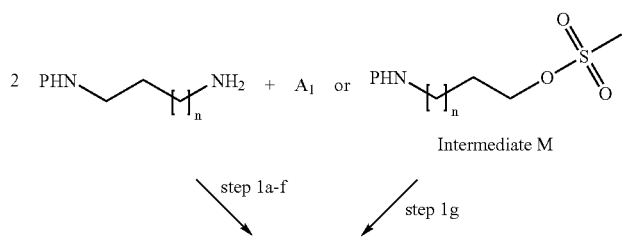

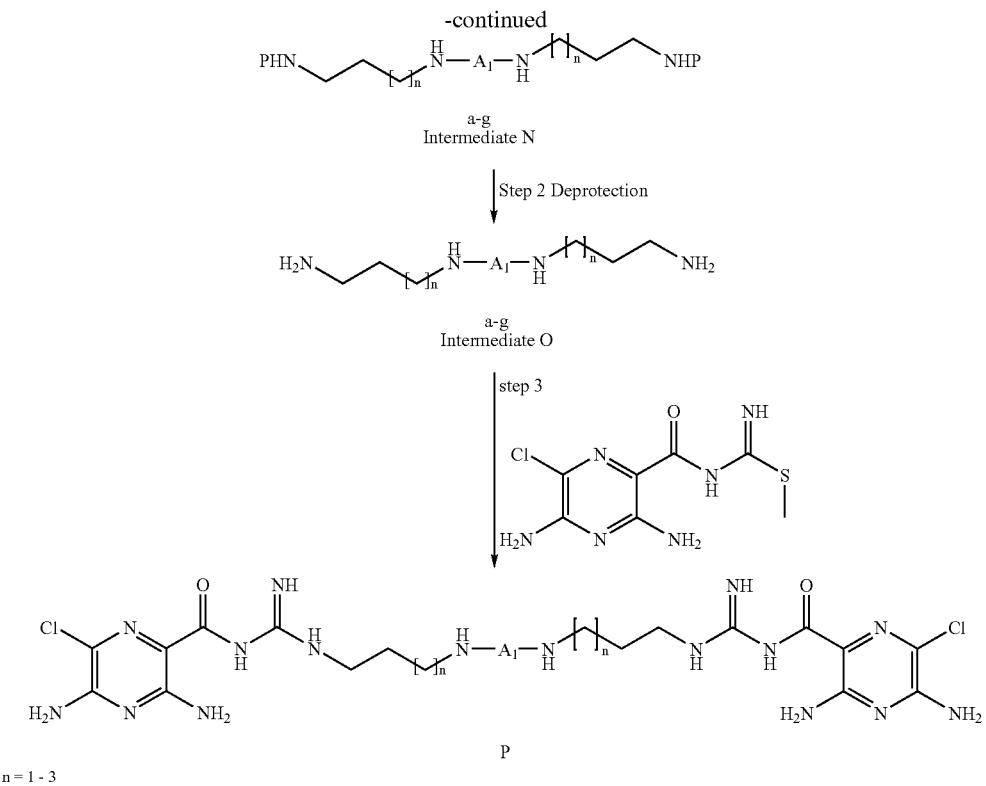

Compounds prepared from Intermediate M are prepared as follows:

Intermediate O (1 eq) is added to a stirring solution of 1-(3,5-diamino-6-chloro-pyrazine-2-carbonyl)-2-methyl-isothiourea hydroiodide (2 eq) in DMF (10 vol). The resulting mixture is heated to 50° C. for 8 hours and then allowed to cool to RT. The reaction mixture is quenched with 5% citric acid solution and the crude product (P) isolated after addition of DCM. Purification by dissolution in MeOH and "capture release" utilizing SCX-2 cartridges affords the title compound upon elution with 1 N ammonia in MeOH.

Compounds prepared from Mono-protected amines are prepared as follows:

Intermediate O (1 eq) is added to a stirring solution of 1-(3,5-diamino-6-chloro-pyrazine-2-carbonyl)-2-methyl-isothiourea hydroiodide (2 eq) in DMF (10 vol). The resulting mixture is heated to 50° C. Upon completion the reaction is quenched with water and the product (P) isolated by filtration.

Further preferred compounds of the present invention include compounds of formula (X) and are as shown in Table 6 below. These compounds are prepared in a multiparallel sequence of reactions as described below in Scheme X. Methods of preparing such compounds are described hereinafter

TABLE 6

(X)

| Ex. | A |
|---|---|
| 581 | —CH$_2$— |
| 582 | CH(CH$_3$)$_2$ (isobutyl group) |

TABLE 6-continued (X)

[Structure: Cl-pyrazine(NH2,NH2)-C(O)-N=C(NH2)-NH-(CH2)4-NH-C(O)-A-NH-C(O)-NH-(CH2)4-NH-C(NH2)=N-C(O)-pyrazine(NH2,NH2)-Cl]

| Ex. | A |
|---|---|
| 583 | isobutyl (CH(CH3)2-CH2-) |
| 584 | isopentyl |
| 585 | sec-butyl-methyl |
| 586 | isopropyl with methyl branch (H3C, CH3) |
| 587 | isopropyl with methyl branch (H3C, CH3) |
| 588 | 2-methylbutyl with methyl, ethyl |
| 589 | 2-methylbutyl with methyl, ethyl |
| 590 | 2,4-dimethylpentyl |
| 591 | 2,4-dimethylpentyl |
| 592 | 2,2,3-trimethylbutyl |

TABLE 6-continued
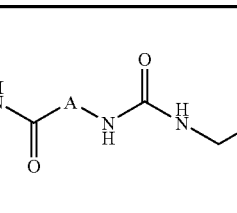
(X)
| Ex. | A |
|---|---|
| 593 | 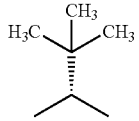 |
| 594 | 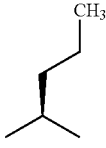 |
| 595 | 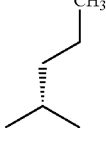 |
| 596 |  |
| 597 | 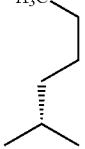 |
| 598 | 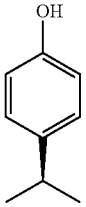 |
| 599 | 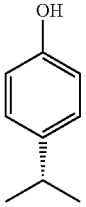 |

TABLE 6-continued
(X)
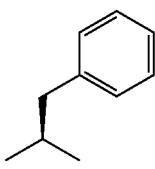
| Ex. | A |
|---|---|
| 600 | 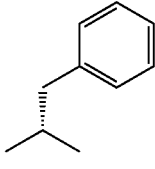 |
| 601 | 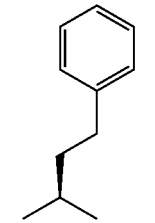 |
| 602 | 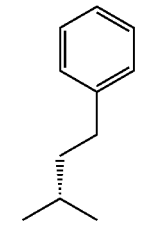 |
| 603 | 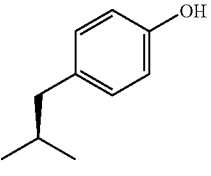 |
| 604 | 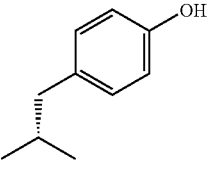 |
| 605 | |

TABLE 6-continued (X)

| Ex. | A |
|---|---|
| 606 | 3,4-dihydroxy-substituted isobutylphenyl |
| 607 | 3,4-dihydroxy-substituted isobutylphenyl |
| 608 | 3-fluoro-4-hydroxy-substituted isobutylphenyl |
| 609 | 3-fluoro-4-hydroxy-substituted isobutylphenyl |
| 610 | 3-iodo-4-hydroxy-substituted isobutylphenyl |
| 611 | 3-iodo-4-hydroxy-substituted isobutylphenyl |

TABLE 6-continued
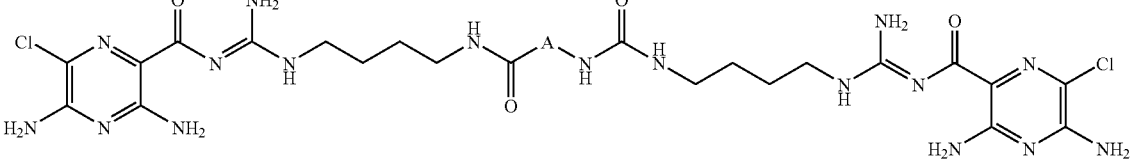
(X)
| Ex. | A |
|---|---|
| 612 | 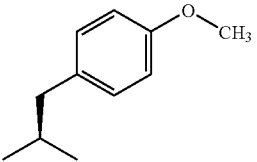 |
| 613 | 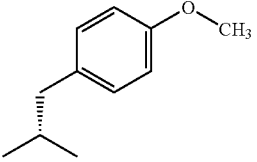 |
| 614 | 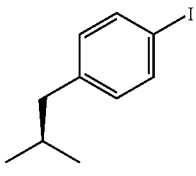 |
| 615 | 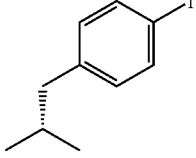 |
| 616 | —CH$_2$CH$_2$— |
| 617 | 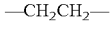 |
| 618 |  |
| 619 |  |
| 620 | 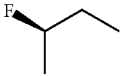 |
| 621 |  |
| 622 | 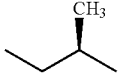 |

TABLE 6-continued
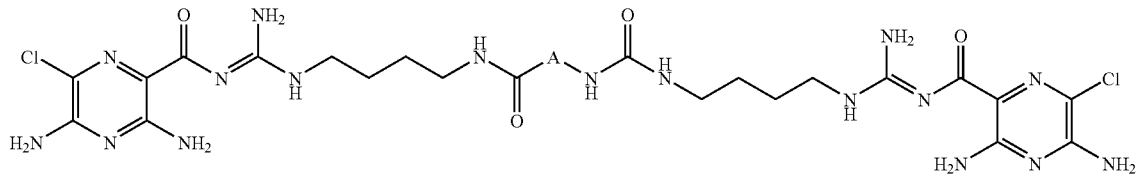
(X)
| Ex. | A |
|---|---|
| 623 | 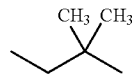 |
| 624 | 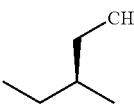 |
| 625 | 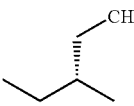 |
| 626 | 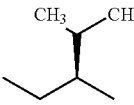 |
| 627 | 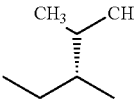 |
| 628 | 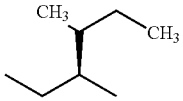 |
| 629 | 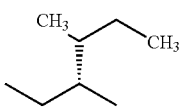 |
| 630 | 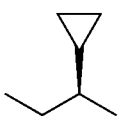 |
| 631 | 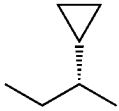 |
| 632 | 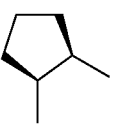 |
| 633 | 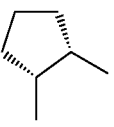 |

TABLE 6-continued
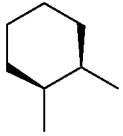
(X)
| Ex. | A |
|---|---|
| 634 | 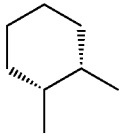 |
| 635 | 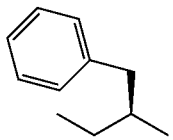 |
| 636 | 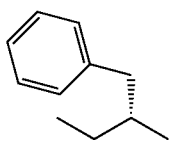 |
| 637 | 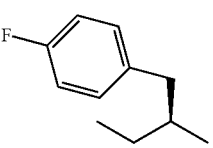 |
| 638 | 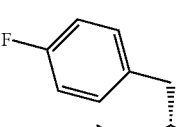 |
| 639 | 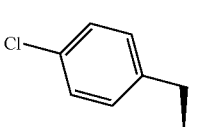 |
| 640 | 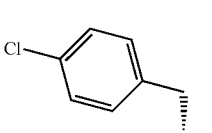 |
| 641 | |

TABLE 6-continued
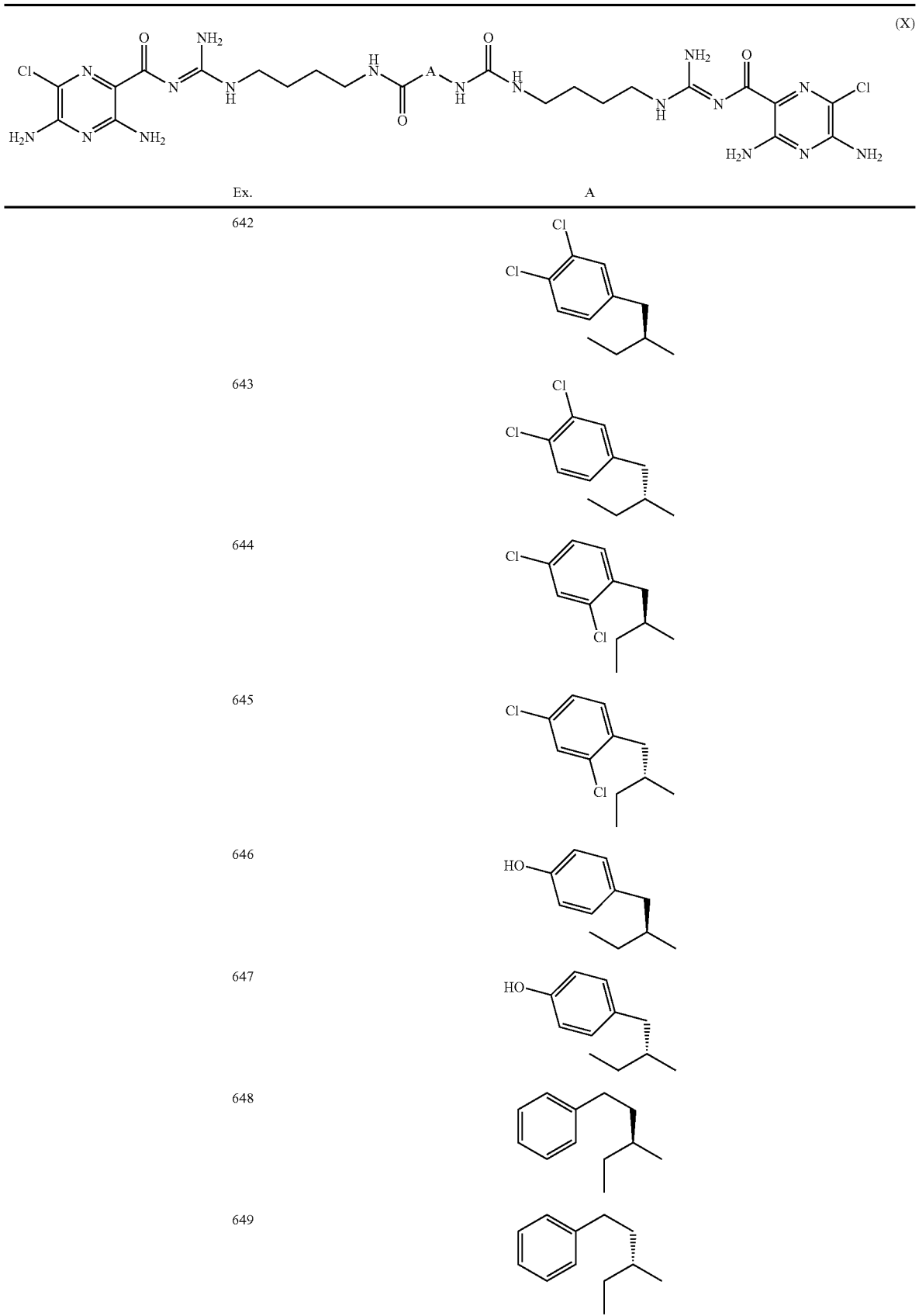
| Ex. | A |
|---|---|
| 642 | 3,4-dichlorobenzyl-2-butyl |
| 643 | 3,4-dichlorobenzyl-2-butyl |
| 644 | 2,4-dichlorobenzyl-2-butyl |
| 645 | 2,4-dichlorobenzyl-2-butyl |
| 646 | 4-hydroxybenzyl-2-butyl |
| 647 | 4-hydroxybenzyl-2-butyl |
| 648 | 2-phenylethyl-2-butyl |
| 649 | 2-phenylethyl-2-butyl |

TABLE 6-continued
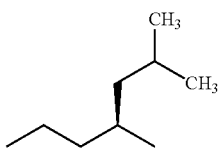
(X)
| Ex. | A |
|-----|---|
| 650 | —CH₂CH₂CH₂— |
| 651 | 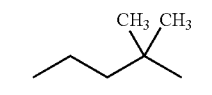 |
| 652 | 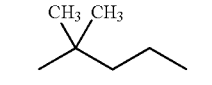 |
| 653 | 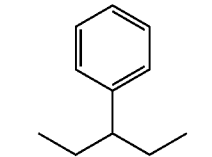 |
| 654 | 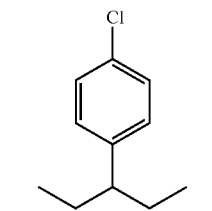 |
| 655 | 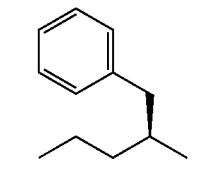 |
| 656 | 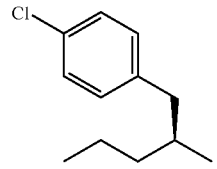 |
| 657 | 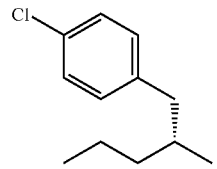 |
| 658 |  |

TABLE 6-continued
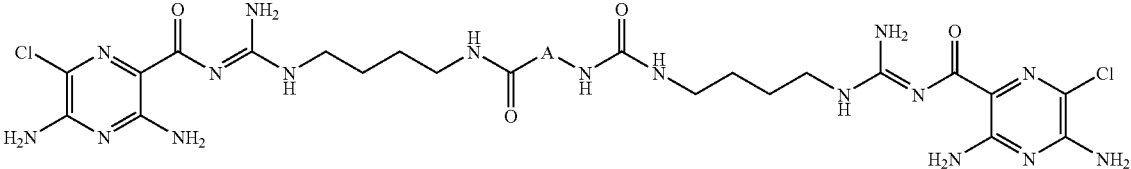
| Ex. | A |
|---|---|
| 659 | 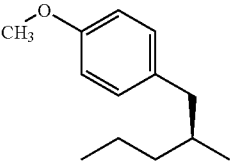 |
| 660 | 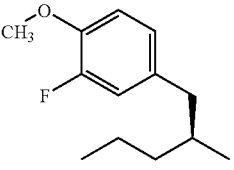 |
| 661 | 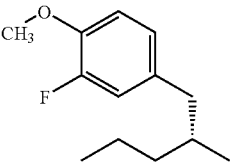 |
| 662 | 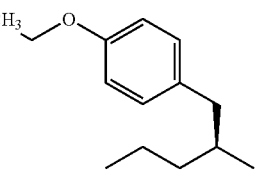 |
| 663 | 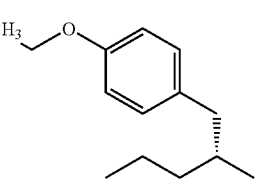 |
| 664 | 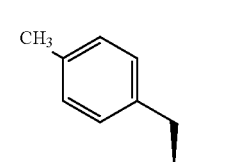 |
| 665 | |

TABLE 6-continued
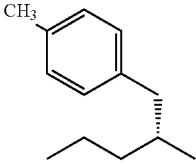
(X)
| Ex. | A |
|---|---|
| 666 | 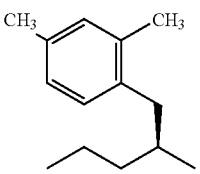 |
| 667 | 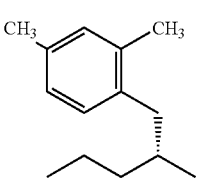 |
| 668 | 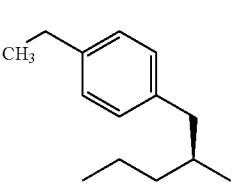 |
| 669 | 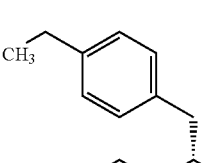 |
| 670 | 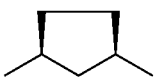 |
| 671 | 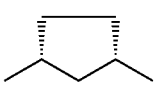 |
| 672 | |

Scheme X
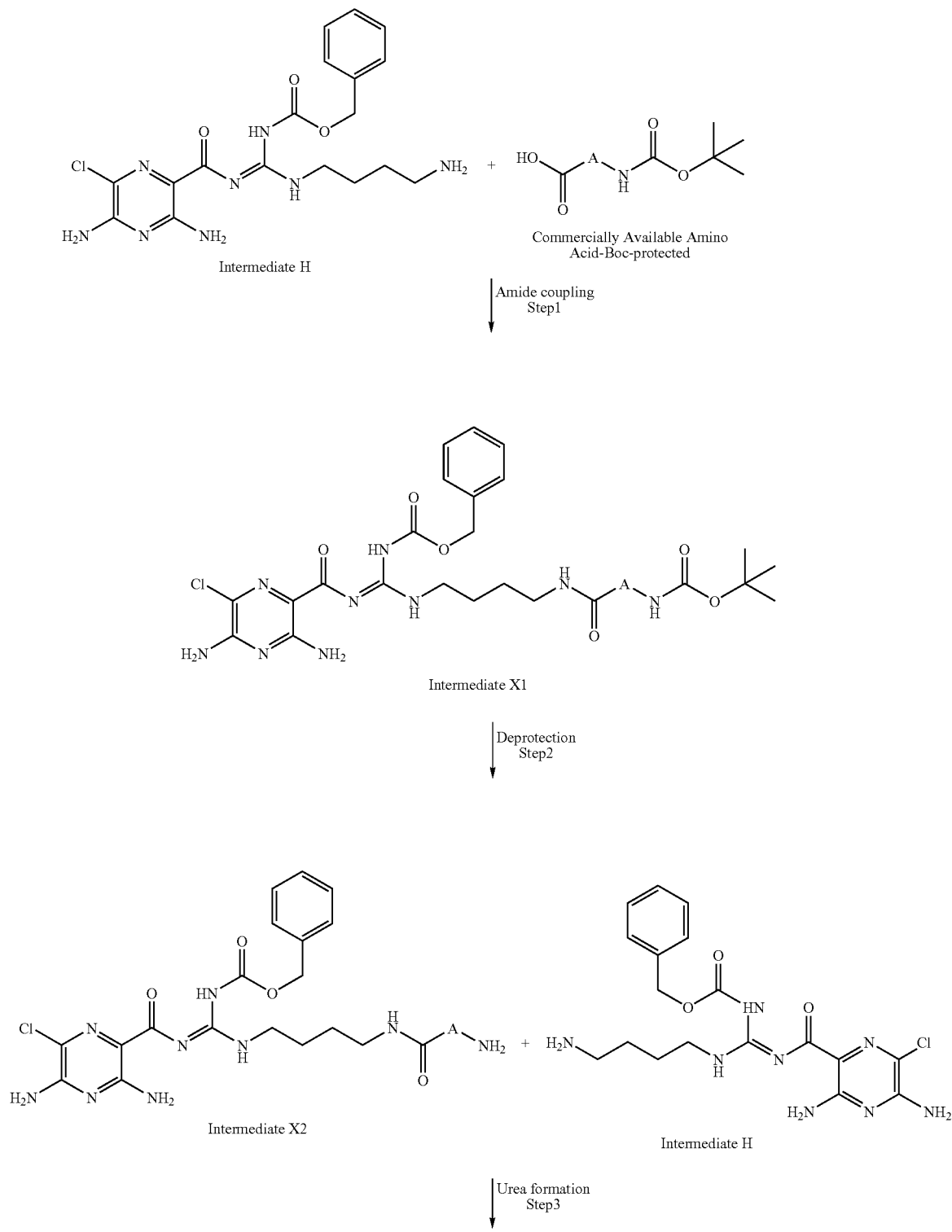

-continued

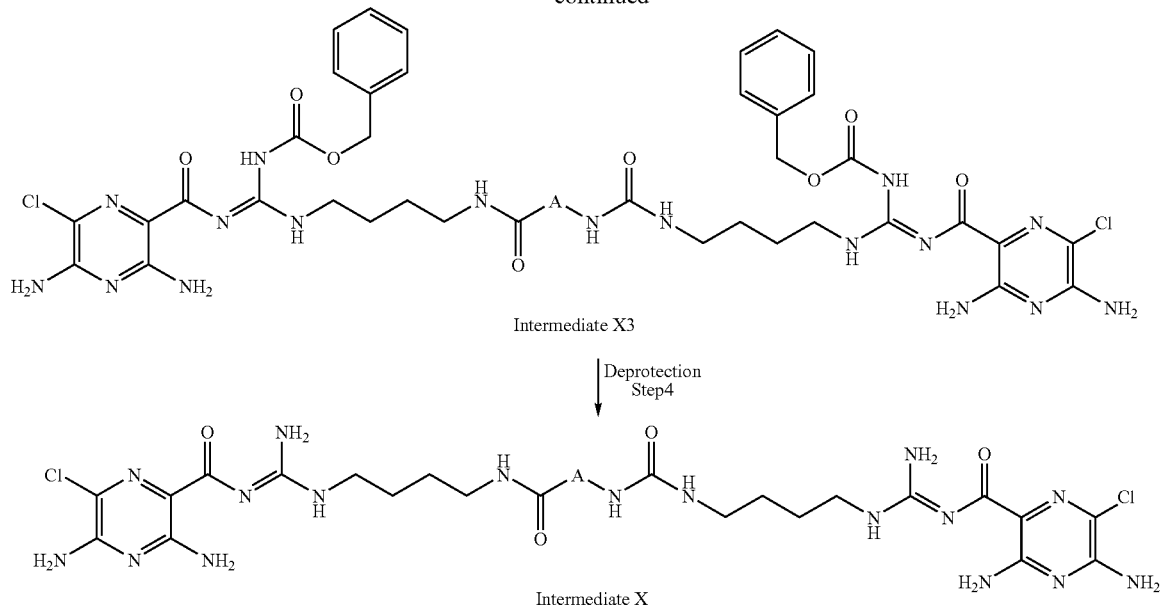

Intermediate X3

Deprotection Step4

Intermediate X

Step 1:

Reaction of Intermediate H with a Boc-protected amino acid (commercially available or prepared from a commercially-available amino acid) using a standard peptide coupling reagent gives the Intermediate X1.

Step 2:

Deprotection of Intermediate X1 with TFA gives Intermediate X2.

Step 3:

Reaction of Intermediate X2 with Intermediate H using a urea forming reagent (e.g., CDI, bis(p-nitrophenyl)carbonate) gives Intermediate X3.

Step 4:

Deprotection of Intermediate X3 with HBr/Acetic acid gives compounds of formula (X).

Further preferred compounds of the present invention include compounds of formula (Y) are as shown in Table 6 below. They are prepared in a multiparallel sequence of reactions as described below in Scheme Y:

TABLE 7

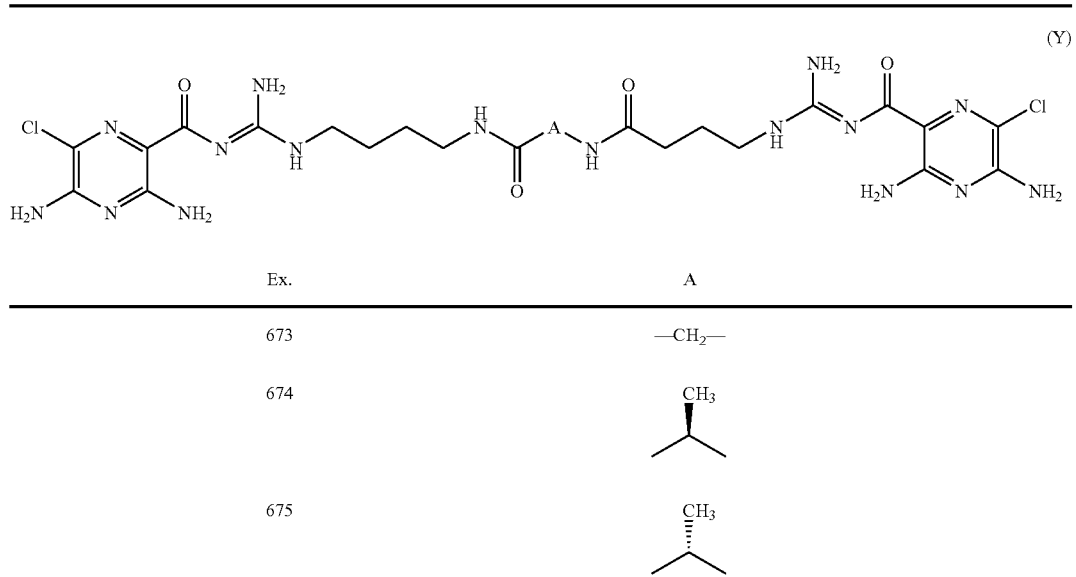

| Ex. | A |
|---|---|
| 673 | —CH$_2$— |
| 674 | CH$_3$ (isobutyl group) |
| 675 | CH$_3$ (isobutyl group) |

TABLE 7-continued
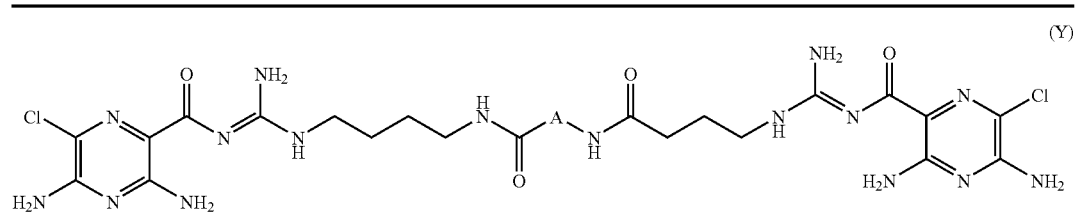
(Y)
| Ex. | A |
|---|---|
| 676 | 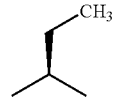 |
| 677 | 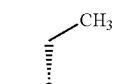 |
| 678 | 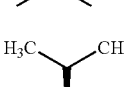 |
| 679 | 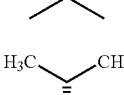 |
| 680 | 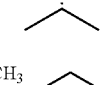 |
| 681 | 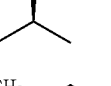 |
| 682 | 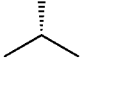 |
| 683 | 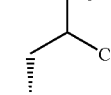 |
| 684 | 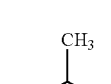 |
| 685 |  |

TABLE 7-continued
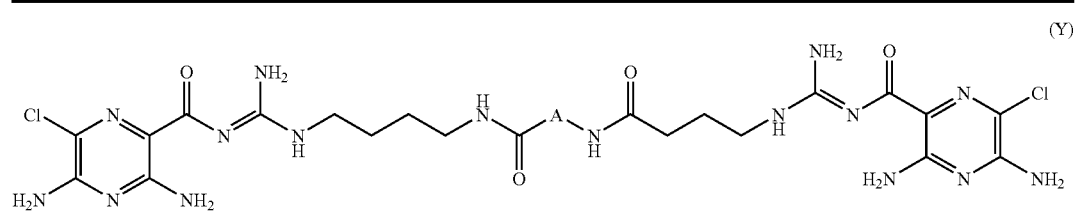
| Ex. | A |
|---|---|
| 686 | 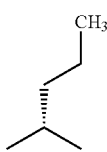 |
| 687 |  |
| 688 | 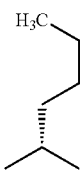 |
| 689 | 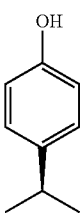 |
| 690 | 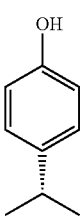 |
| 691 | |
| 692 | 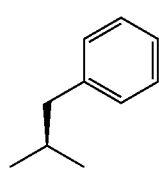 |

TABLE 7-continued
(Y)
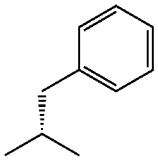
| Ex. | A |
|---|---|
| 693 | 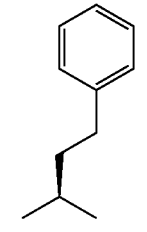 |
| 694 | 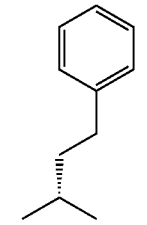 |
| 695 | 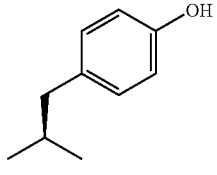 |
| 696 | 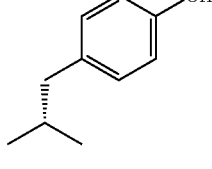 |
| 697 | 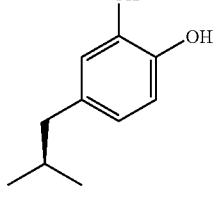 |
| 698 | |

TABLE 7-continued
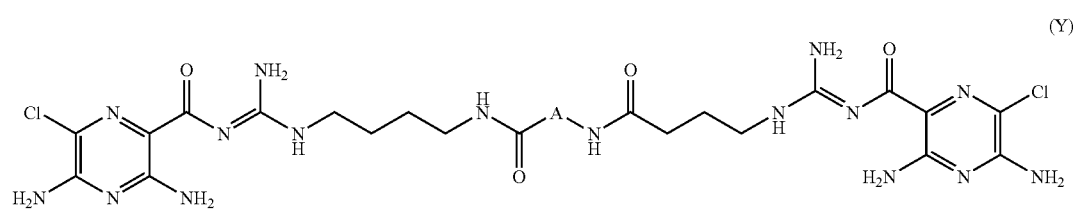
| Ex. | A |
|---|---|
| 699 | 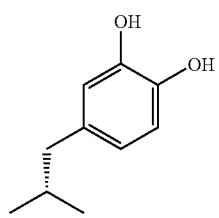 |
| 700 | 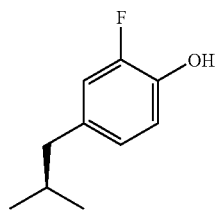 |
| 701 | 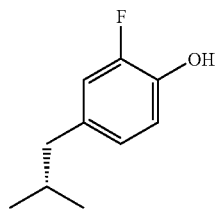 |
| 702 | 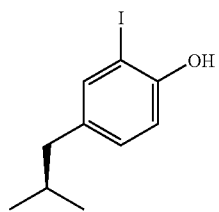 |
| 703 | 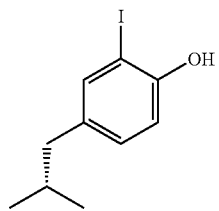 |
| 704 | 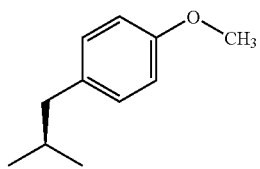 |

TABLE 7-continued
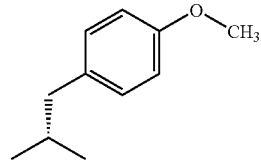
| Ex. | A |
|---|---|
| 705 | 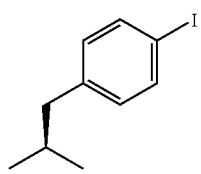 |
| 706 | 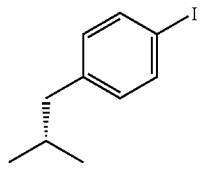 |
| 707 | 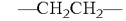 |
| 708 | —CH₂CH₂— |
| 709 | 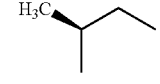 |
| 710 | 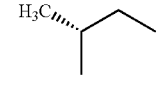 |
| 711 | 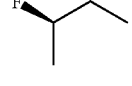 |
| 712 | 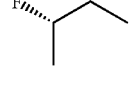 |
| 713 | 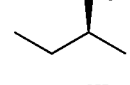 |
| 714 | 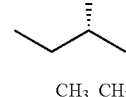 |
| 715 |  |
| 716 | 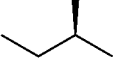 |

TABLE 7-continued
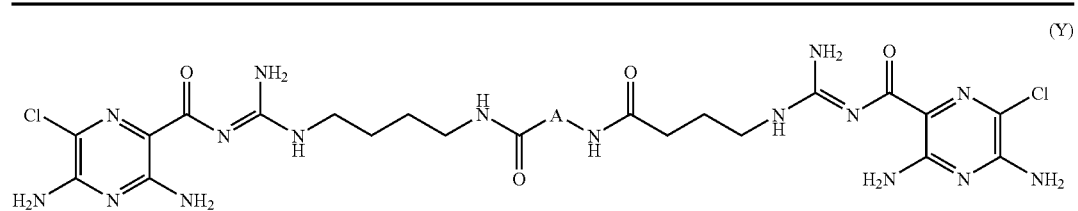
(Y)
| Ex. | A |
|---|---|
| 717 | 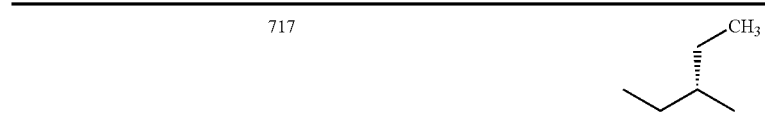 |
| 718 | 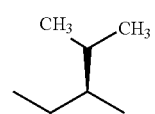 |
| 719 | 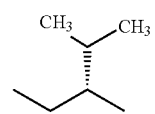 |
| 720 | 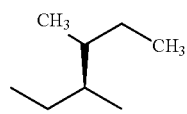 |
| 721 | 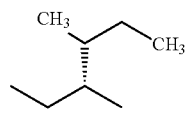 |
| 722 | 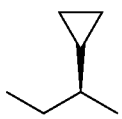 |
| 723 | 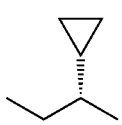 |
| 724 | 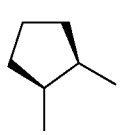 |
| 725 | 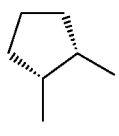 |
| 726 | 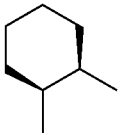 |

TABLE 7-continued
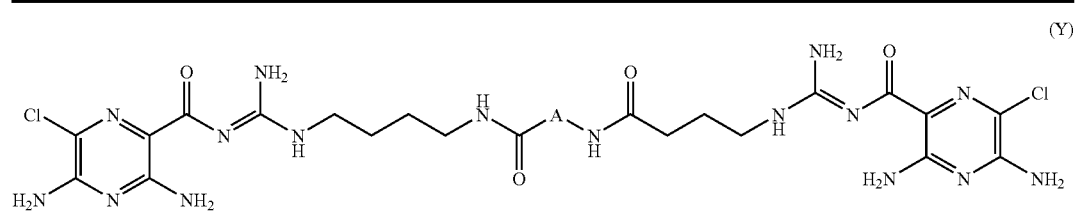
| Ex. | A |
|---|---|
| 727 | 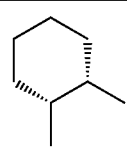 |
| 728 | 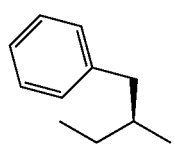 |
| 729 | 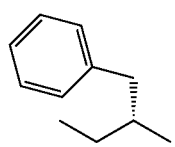 |
| 730 | 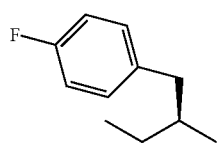 |
| 731 | 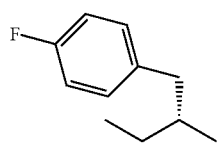 |
| 732 | 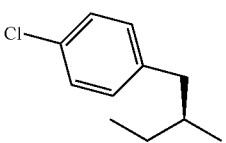 |
| 733 | 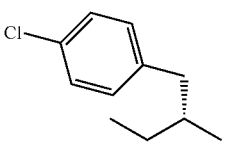 |
| 734 | 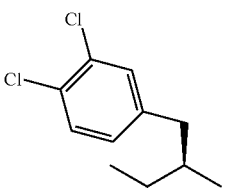 |

TABLE 7-continued
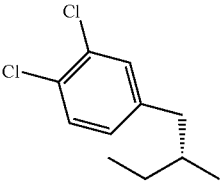
(Y)
| Ex. | A |
|---|---|
| 735 |  |
| 736 | 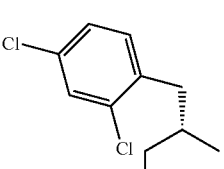 |
| 737 | 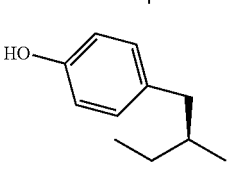 |
| 738 | 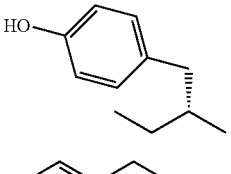 |
| 739 | 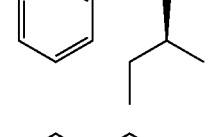 |
| 740 | 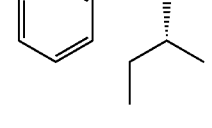 |
| 741 | 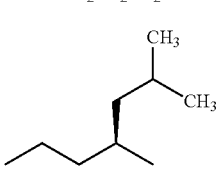 |
| 742 | —CH$_2$CH$_2$CH$_2$— |
| 743 |  |

TABLE 7-continued

| Ex. | A |
|---|---|
| 744 | (neopentyl-ethyl group: CH₂CH₂C(CH₃)₂CH₃ — 3,3-dimethylbutyl) |
| 745 | (3,3-dimethylbutyl variant) |
| 746 | (1-phenylpropyl / 3-phenylpentan-3-yl) |
| 747 | (1-(4-chlorophenyl)propyl) |
| 748 | (2-methyl-1-phenylpentyl, stereo) |
| 749 | (2-methyl-1-(4-chlorophenyl)pentyl, stereo) |
| 750 | (2-methyl-1-(4-chlorophenyl)pentyl, stereo) |
| 751 | (2-methyl-1-(4-methoxyphenyl)pentyl, stereo) |

TABLE 7-continued
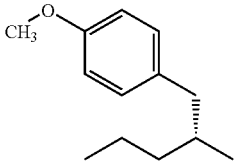
| Ex. | A |
|---|---|
| 752 | 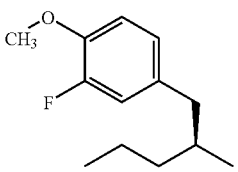 |
| 753 | 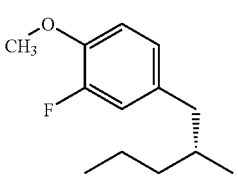 |
| 754 | 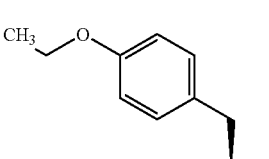 |
| 755 | 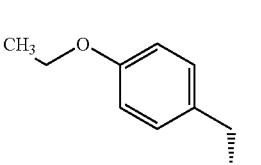 |
| 756 | 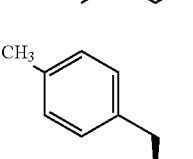 |
| 757 | 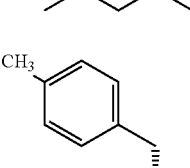 |
| 758 | |

TABLE 7-continued
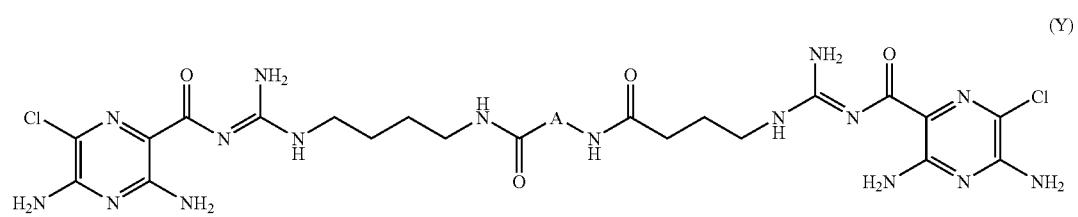
| Ex. | A |
|---|---|
| 759 | 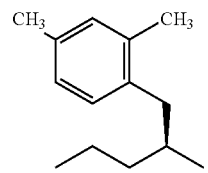 |
| 760 | 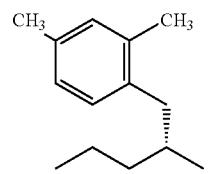 |
| 761 | 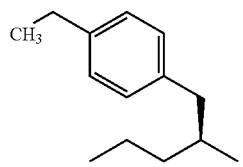 |
| 762 | 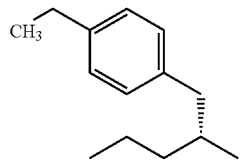 |
| 763 | 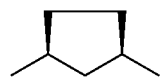 |
| 764 | 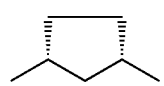 |

Scheme Y
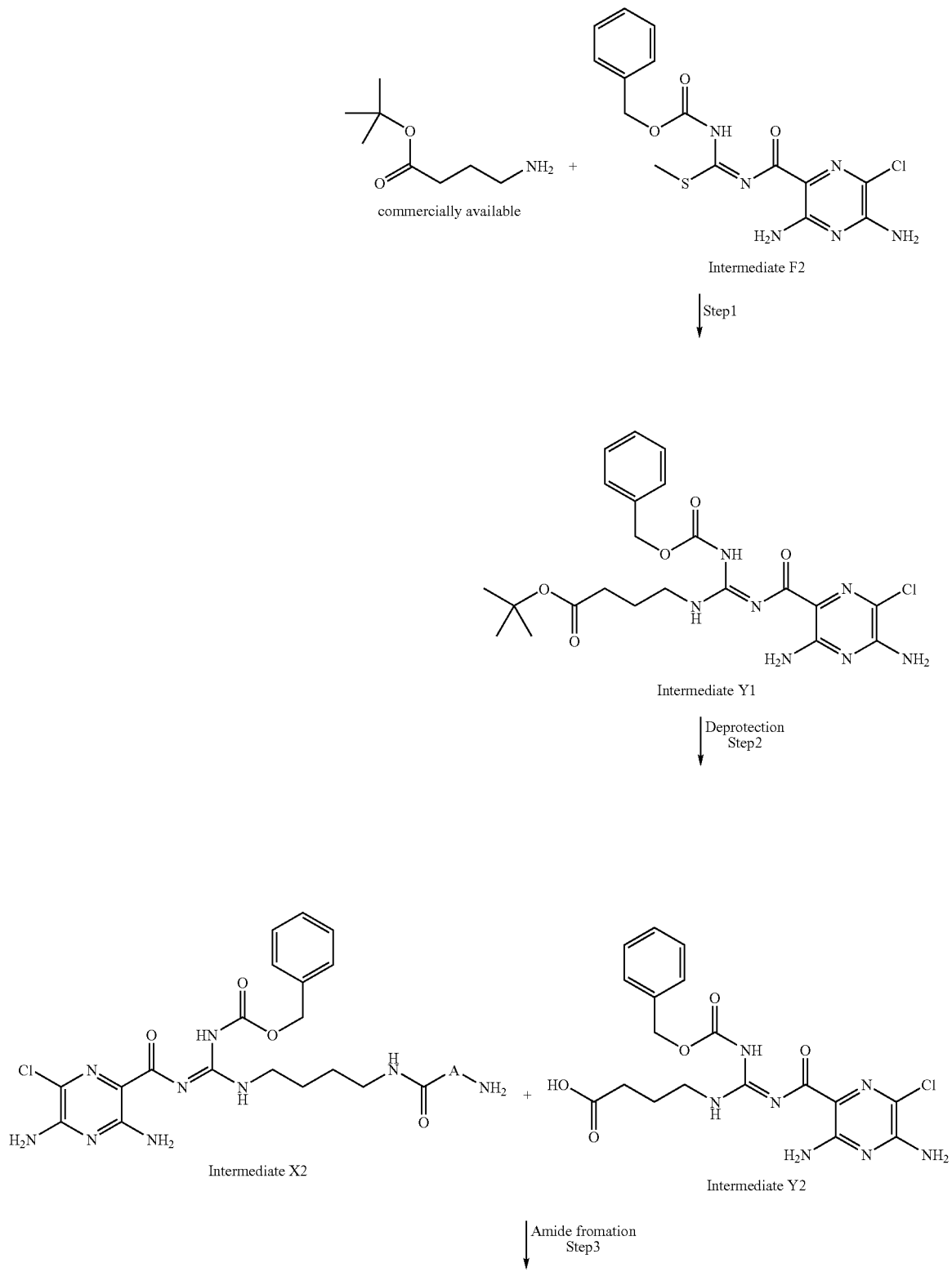

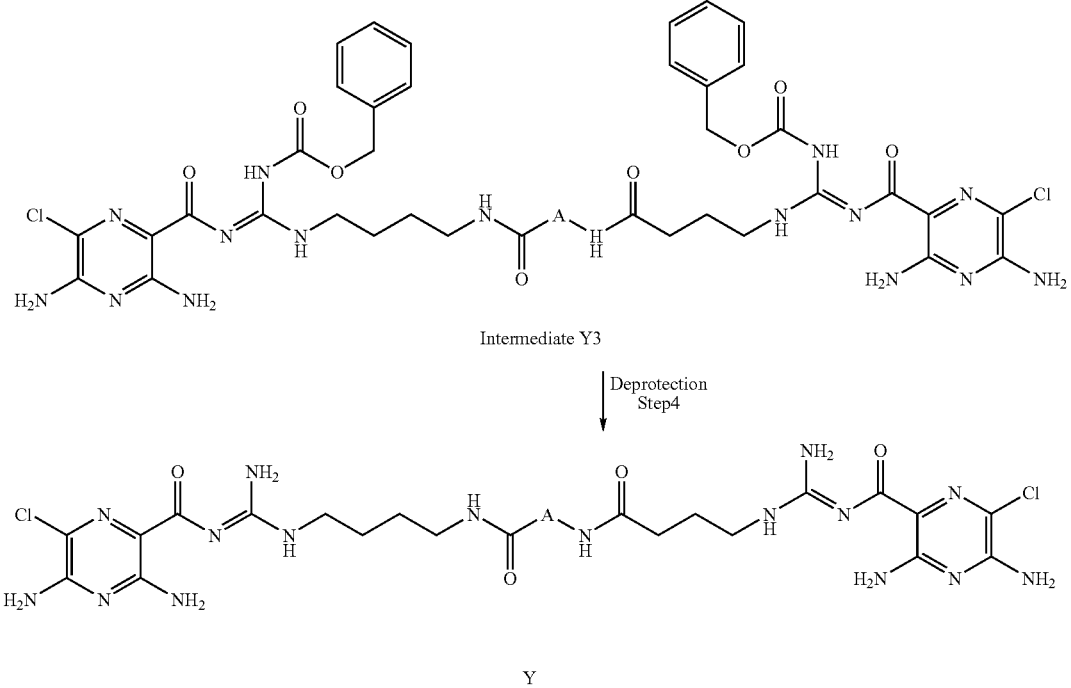

Intermediate Y3

Deprotection Step4

Y

Step 1:

Reaction of Intermediate F2 with a tertbutyl aminoalkane carboxylate (commercially-available or prepared from a commercially available amino acid) gives Intermediate Y1.

Step 2:

Deprotection of Intermediate Y1 with TFA gives Intermediate Y2.

Step 3:

Reaction of Intermediate Y2 with Intermediate X2 using a peptide coupling reagent gives Intermediate Y3.

Step 4:

Deprotection of Intermediate Y3 with HBr/Acetic acid gives the final compound Y.

Further preferred compounds of the present invention include compounds of formula Z and are as shown in Table 8 below. These compounds are prepared in a multiparallel sequence of reactions as described below in Scheme Z. Methods of preparing such compounds are described hereinafter.

TABLE 8

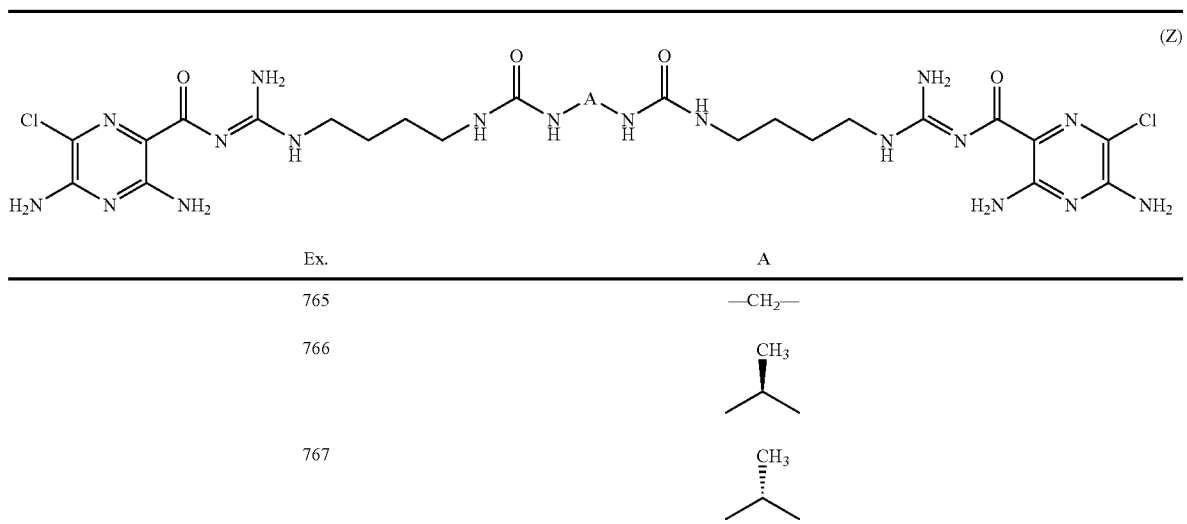

| Ex. | A |
|---|---|
| 765 | —CH$_2$— |
| 766 | CH$_3$ (isobutyl) |
| 767 | CH$_3$ (isobutyl) |

TABLE 8-continued
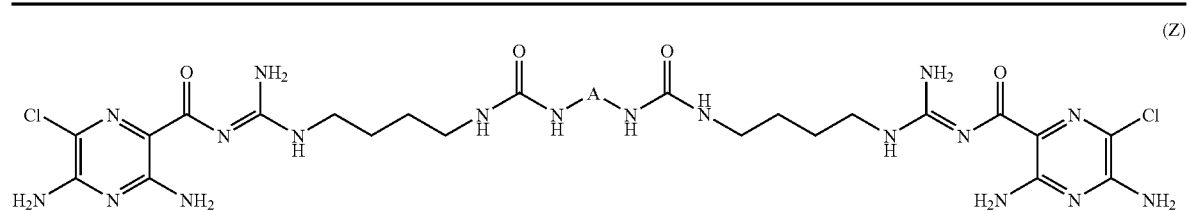
| Ex. | A |
|---|---|
| 768 | |
| 769 | |
| 770 | |
| 771 | |
| 772 | |
| 773 | |
| 774 | |
| 775 | |
| 776 | |
| 777 | |

TABLE 8-continued (Z structure: chloropyrazine-diaminocarboxamide-guanidine-(CH2)4-NH-C(O)-NH-A-NH-C(O)-NH-(CH2)4-guanidine-carboxamide-chloropyrazine-diamine)

| Ex. | A |
|---|---|
| 778 | 3-methylbutyl (CH(CH3)CH2CH2CH3 branched - isopentyl with CH3) |
| 779 | 3-methylbutyl isomer |
| 780 | 5-methylhexyl |
| 781 | 5-methylhexyl |
| 782 | 4-hydroxyphenyl with isopropyl substituent |
| 783 | 4-hydroxyphenyl with isopropyl substituent |
| 784 | phenyl with isobutyl substituent |

TABLE 8-continued (Z)

| Ex. | A |
|-----|---|
| 785 | benzyl-isobutyl group (phenyl-CH2-CH(-)-CH2-CH(CH3)2) |
| 786 | 2-phenylethyl-isobutyl group |
| 787 | 2-phenylethyl-isobutyl group (with stereochemistry) |
| 788 | 4-hydroxyphenyl-methyl-isobutyl group |
| 789 | 4-hydroxyphenyl-methyl-isobutyl group |
| 790 | 3,4-dihydroxyphenyl-isobutyl group |

TABLE 8-continued
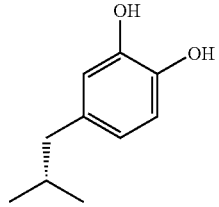
(Z)
| Ex. | A |
|---|---|
| 791 | 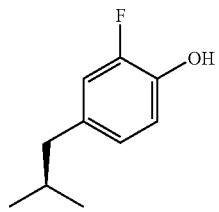 |
| 792 | 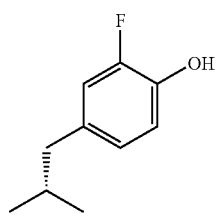 |
| 793 | 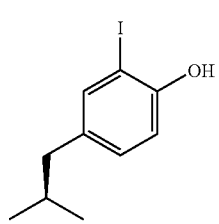 |
| 794 | 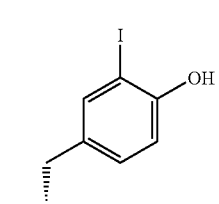 |
| 795 | 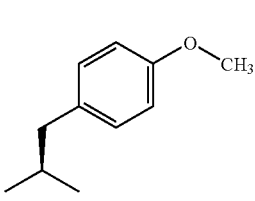 |
| 796 | |

TABLE 8-continued (Z)

| Ex. | A |
|---|---|
| 797 | 4-methoxybenzyl-isobutyl group |
| 798 | 4-iodobenzyl-isobutyl group |
| 799 | 4-iodobenzyl-isobutyl group |
| 800 | —CH$_2$CH$_2$— |
| 801 | (S)-sec-butyl |
| 802 | (R)-sec-butyl |
| 803 | (S)-1-fluoropropyl |
| 804 | (R)-1-fluoropropyl |
| 805 | isobutyl (CH$_3$ wedge) |
| 806 | isobutyl (CH$_3$ dash) |
| 807 | 2,2-dimethylbutyl |
| 808 | 2-methylbutyl |

TABLE 8-continued
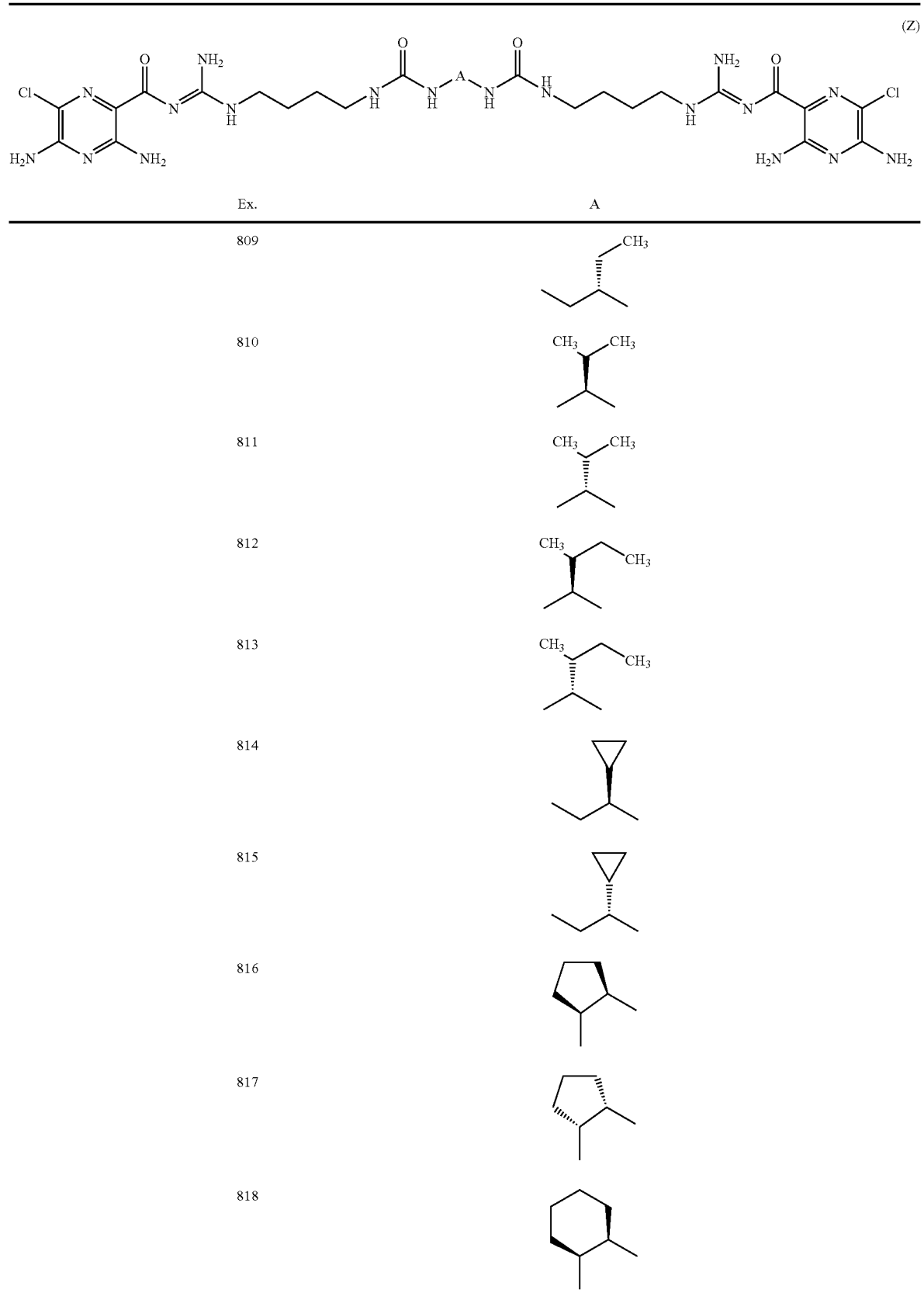

TABLE 8-continued
(Z)
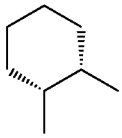
| Ex. | A |
|---|---|
| 819 | 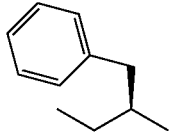 |
| 820 | 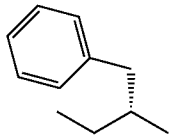 |
| 821 | 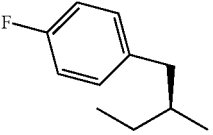 |
| 822 | 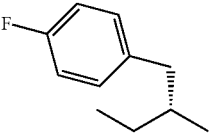 |
| 823 | 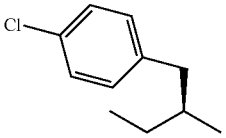 |
| 824 | 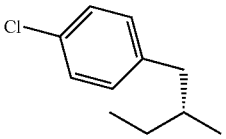 |
| 825 | 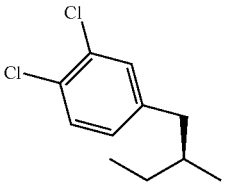 |
| 826 |  |

TABLE 8-continued (Z)

[Structure: Cl-pyrazine(NH2)(NH2)-C(O)-N=C(NH2)-NH-(CH2)4-NH-C(O)-NH-A-NH-C(O)-NH-(CH2)4-NH-C(NH2)=N-C(O)-pyrazine(NH2)(NH2)-Cl]

| Ex. | A |
|---|---|
| 827 | 3,4-dichlorobenzyl-(S)-sec-butyl group |
| 828 | 2,4-dichlorobenzyl-(S)-sec-butyl group |
| 829 | 2,4-dichlorobenzyl-(R)-sec-butyl group |
| 830 | 4-hydroxybenzyl-(S)-sec-butyl group |
| 831 | 4-hydroxybenzyl-(R)-sec-butyl group |
| 832 | 2-phenylethyl-(S)-sec-butyl group |
| 833 | 2-phenylethyl-(R)-sec-butyl group |
| 834 | —CH₂CH₂CH₂— |

TABLE 8-continued
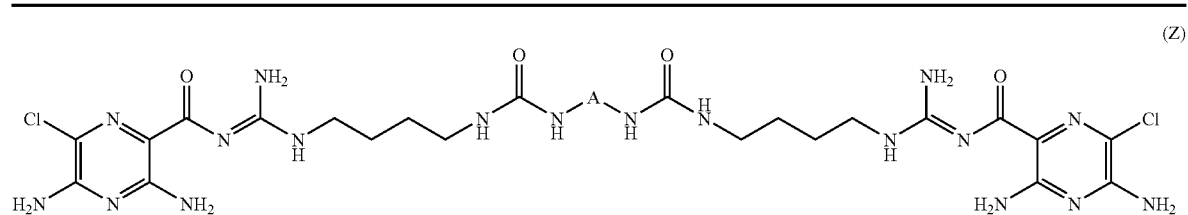
(Z)
| Ex. | A |
|---|---|
| 835 | 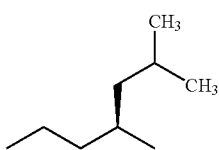 |
| 836 | 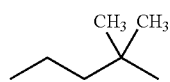 |
| 837 | 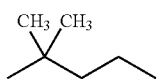 |
| 838 | 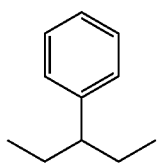 |
| 839 | 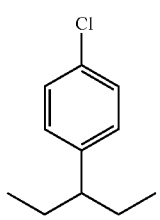 |
| 840 | 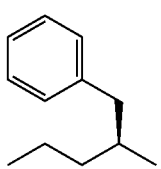 |
| 841 | 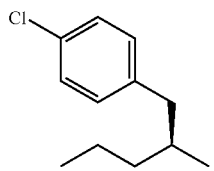 |
| 842 | 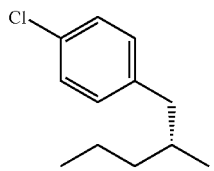 |

TABLE 8-continued (Z)

| Ex. | A |
|---|---|
| 843 | 4-methoxybenzyl, (S)-2-methylpentyl |
| 844 | 4-methoxybenzyl, (R)-2-methylpentyl |
| 845 | 3-fluoro-4-methoxybenzyl, (S)-2-methylpentyl |
| 846 | 3-fluoro-4-methoxybenzyl, (R)-2-methylpentyl |
| 847 | 4-ethoxybenzyl, (S)-2-methylpentyl |
| 848 | 4-ethoxybenzyl, (R)-2-methylpentyl |
| 849 | 4-methylbenzyl, (S)-2-methylpentyl |

TABLE 8-continued
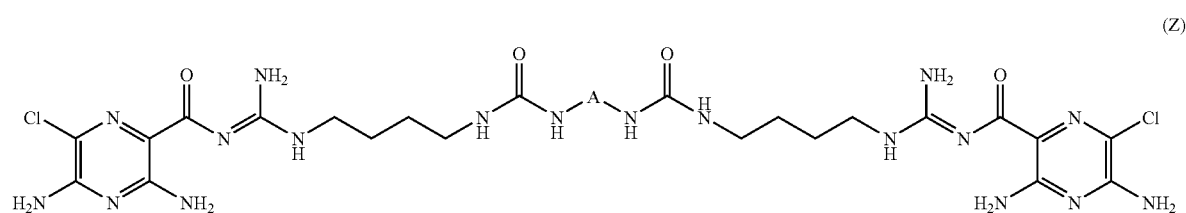
(Z)
| Ex. | A |
|---|---|
| 850 | 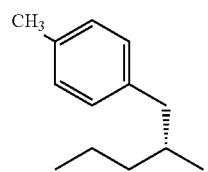 |
| 851 | 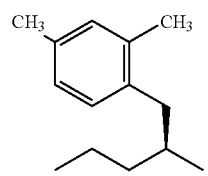 |
| 852 | 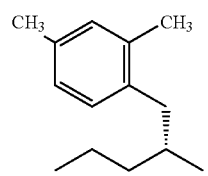 |
| 853 | 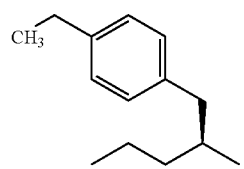 |
| 854 | 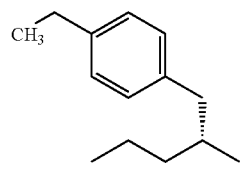 |
| 855 | 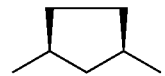 |
| 856 | 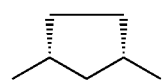 |

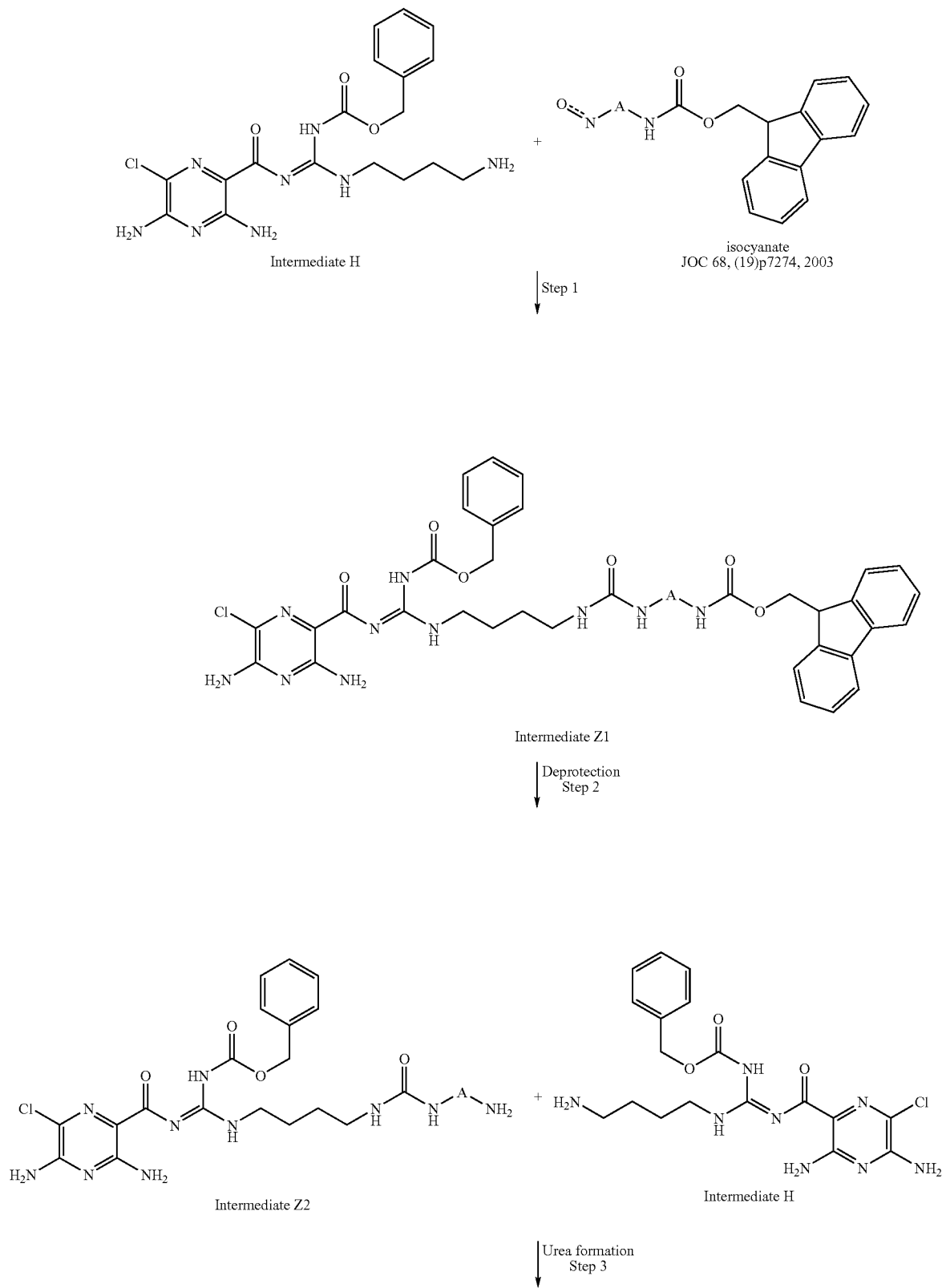

-continued

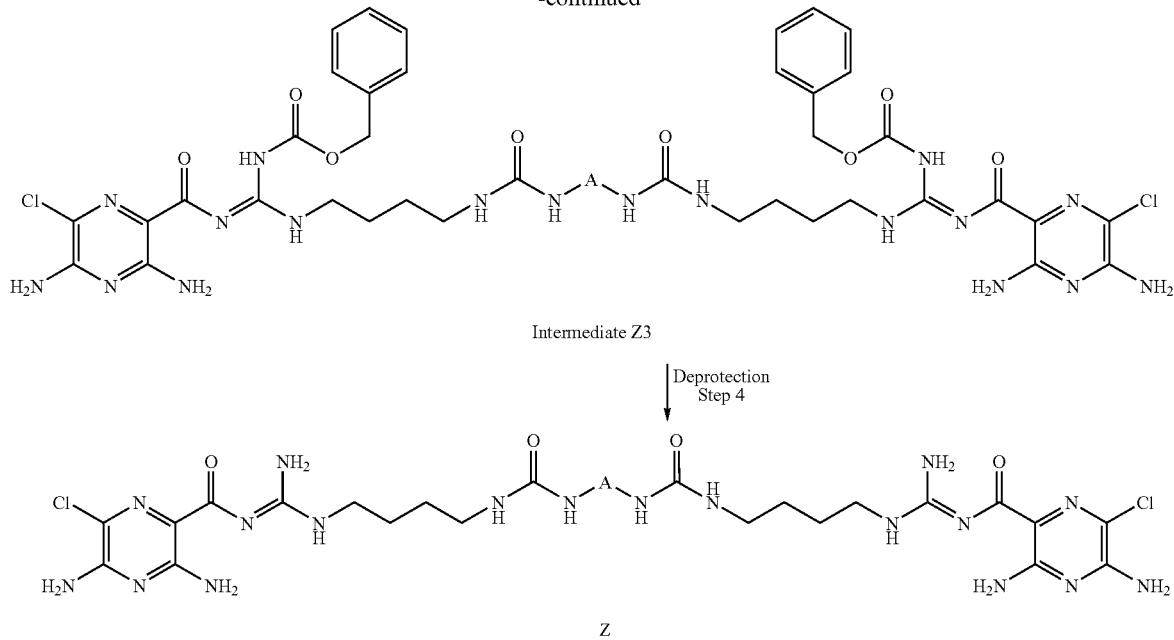

Intermediate Z3

↓ Deprotection Step 4

Z

Step 1:

Reaction of Intermediate H with the appropriate isocyanate [prepared according to JOC, Vol. 68, No. 19, p. 7274 (2003)] gives Intermediate Z1.

Step 2:

Removal of the protecting group from Intermediate Z1 with piperidine gives Intermediate Z2.

Step 3:

Reaction of Intermediate Z2 with Intermediate H using a urea forming reagent (e.g. CDI, bis(p-nitrophenyl)carbonate) gives the Intermediate Z3.

Step 4:

Deprotection of Intermediate Z3 with HBr/Acetic acid gives the final compound Z.

Yet further preferred compounds of the present invention include compounds of formula (T) and are as shown in Table 9 below. Methods of preparing such compounds are described hereinafter.

TABLE 9

(T)

| Ex. | R |
|-----|---|
| 857 | —H |
| 858 | HN-CH₃ (N-methyl) |
| 859 | HN-CH₂CH₃ (N-ethyl) |

TABLE 9-continued
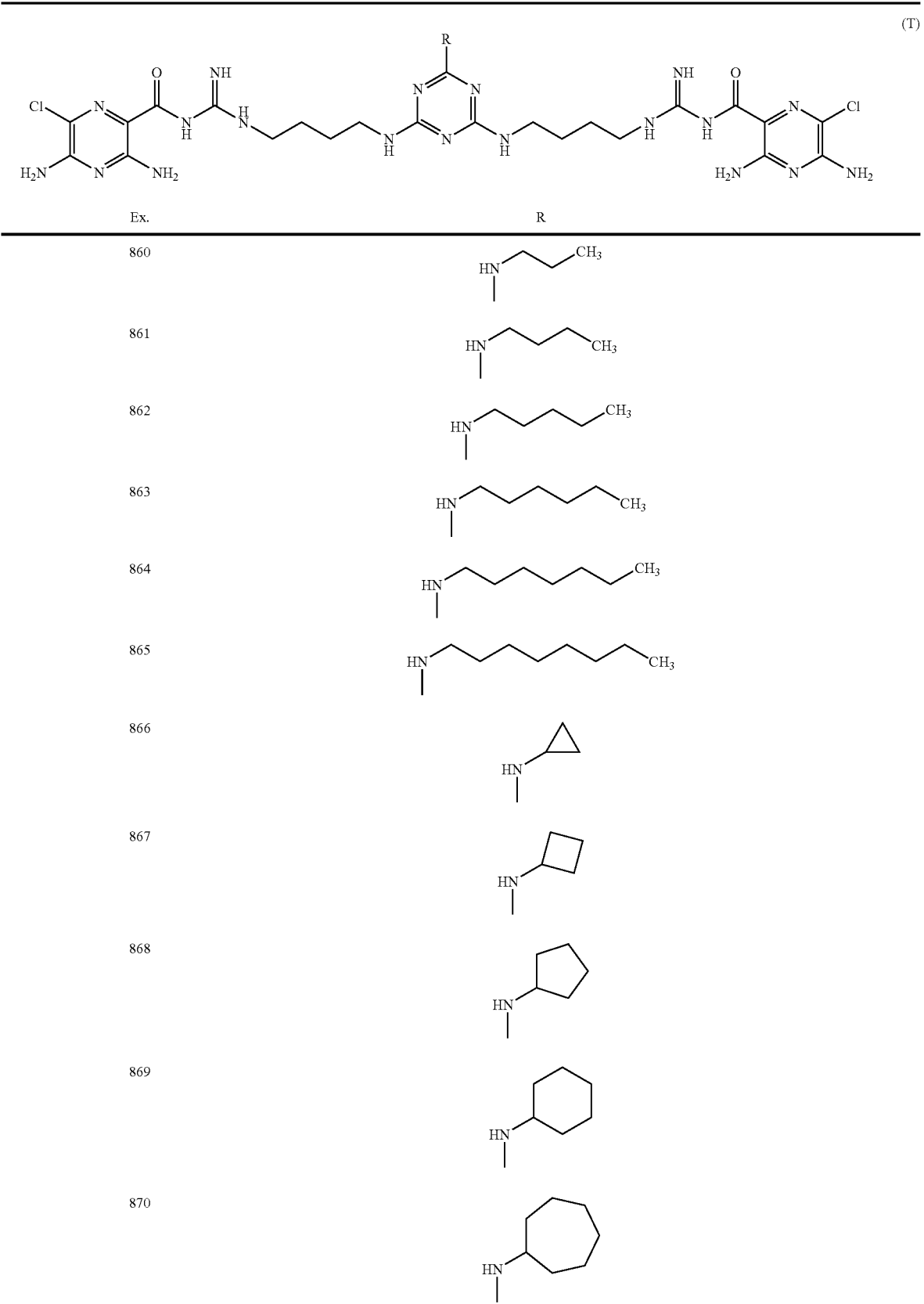

TABLE 9-continued
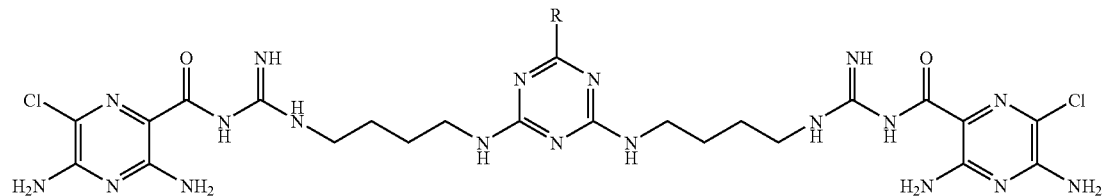
(T)
| Ex. | R |
|---|---|
| 871 | 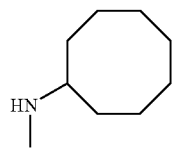 |
| 872 | 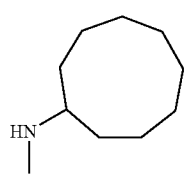 |
| 873 | 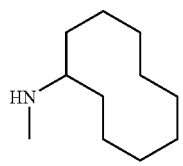 |
| 874 | 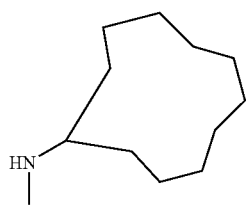 |
| 875 | 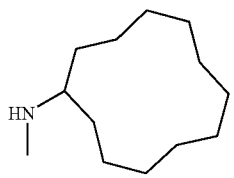 |
| 876 | 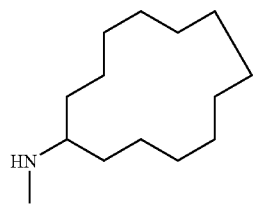 |
| 877 | 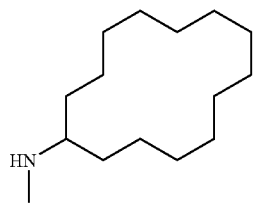 |

TABLE 9-continued
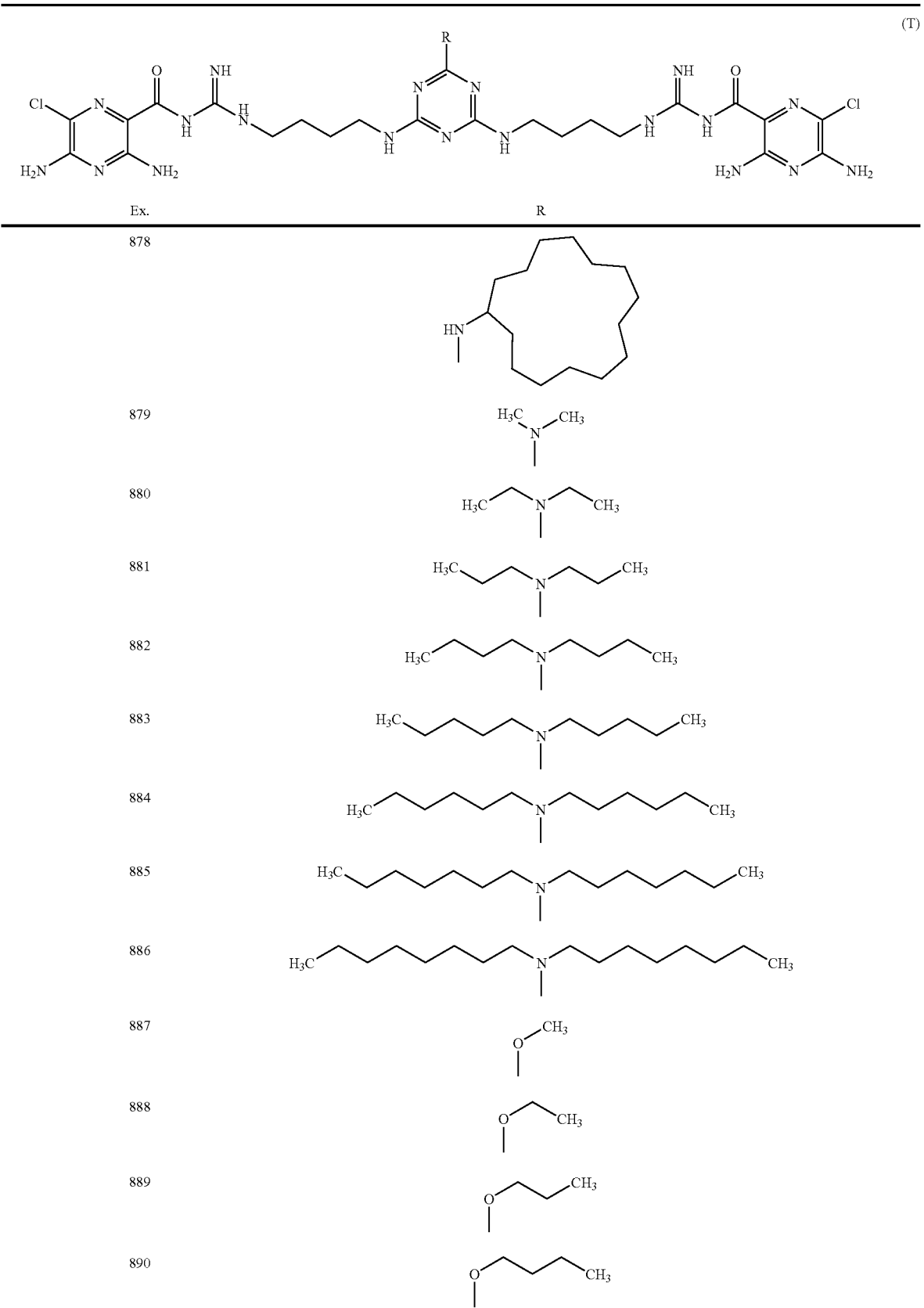
(T)
| Ex. | R |
|---|---|
| 878 | |
| 879 | |
| 880 | |
| 881 | |
| 882 | |
| 883 | |
| 884 | |
| 885 | |
| 886 | |
| 887 | |
| 888 | |
| 889 | |
| 890 | |

TABLE 9-continued (T)

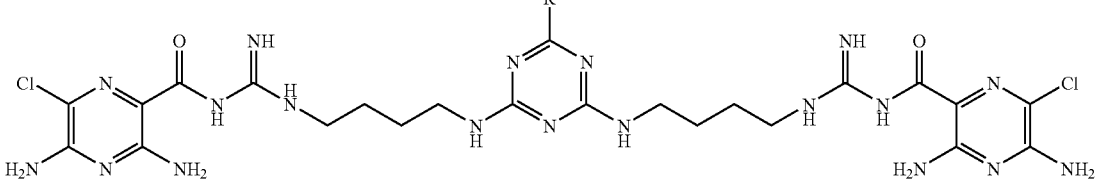

| Ex. | R |
|---|---|
| 891 | 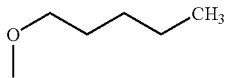 |
| 892 | 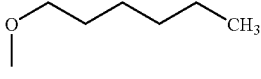 |
| 893 | 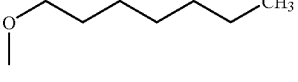 |
| 894 |  |
| 895 | 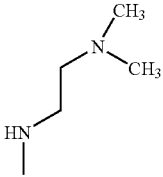 |
| 896 | 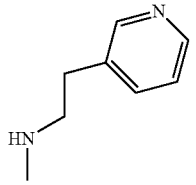 |
| 897 | 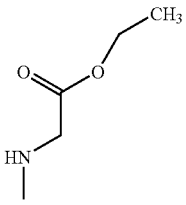 |

Example 857

Intermediate R (15 mg, 16 µmol) is dissolved in (0.75 ml) hydrogen bromide (33% w/w solution in acetic acid) and stirred at RT overnight. The title compound is obtained after purification by reverse phase column chromatography (Isolute™ C18, 0-30% acetonitrile in water—0.1% TFA). (MH+ 678.28).

Examples 857-897

These examples are prepared as follows:

A suspension of Intermediate A and the corresponding Intermediate S in dry DMF is treated with TEA and heated to 65° C. for 96 hours. The reaction mixture is cooled to RT and the product is purified by reverse phase column chromatography (Isolute™ C18, 0-100% acetonitrile in water—0.1% TFA). The fractions comprising the product are concentrated in vacuo. The resulting solid is dissolved in 4 M HCl (in dioxane) and stirred overnight. The reaction mixture is reduce in vacuo to afford the title compound.

Yet further preferred compounds of the present invention are shown in Table 10 below. The method of preparation being described thereinbefore.

TABLE 10

| Ex. | Structure | Viable Preparation Routes |
|---|---|---|
| 898 | 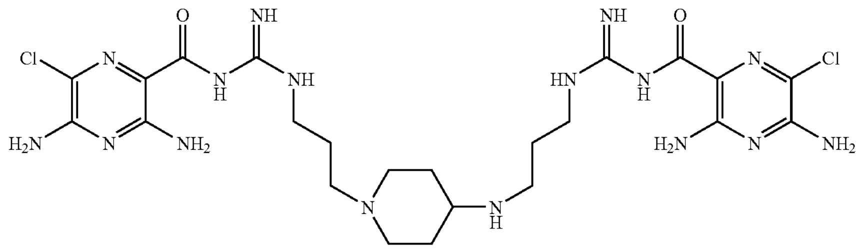 | 6 or 8f |
| 899 | 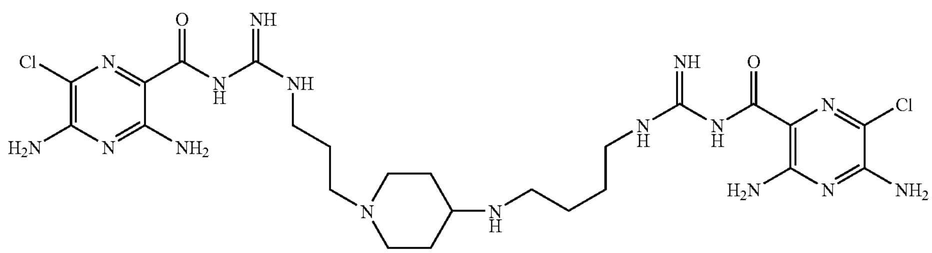 | 6 or 8f |
| 900 | 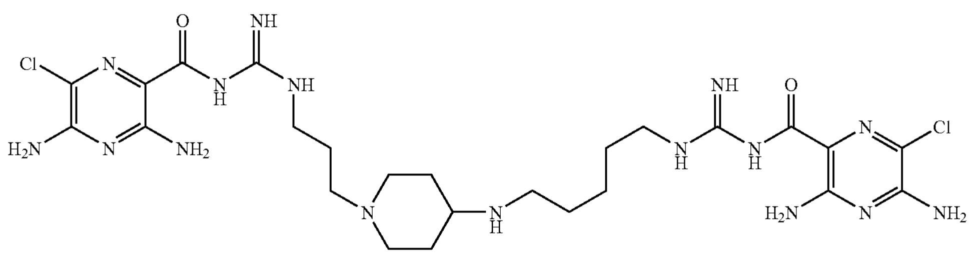 | 6 or 8f |
| 901 | 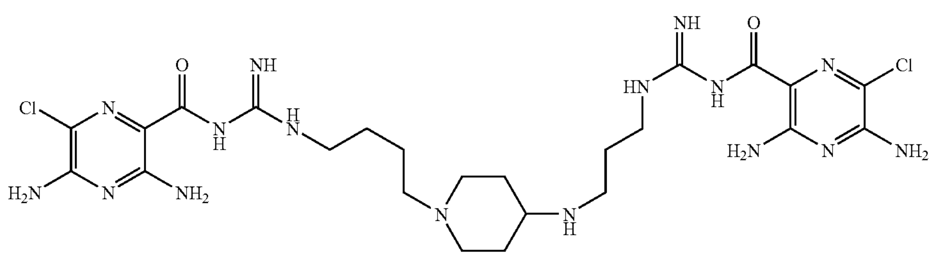 | 6 or 8f |
| 902 | 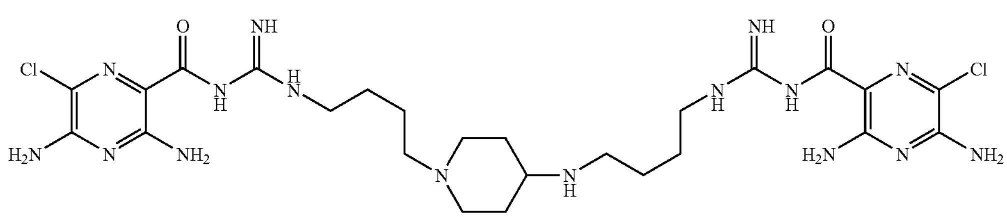 | 6 or 8f |
| 903 | 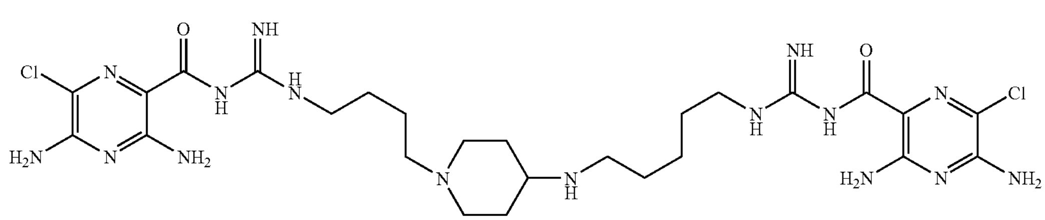 | 6 or 8f |

TABLE 10-continued

| Ex. | Structure | Viable Preparation Routes |
|---|---|---|
| 904 | 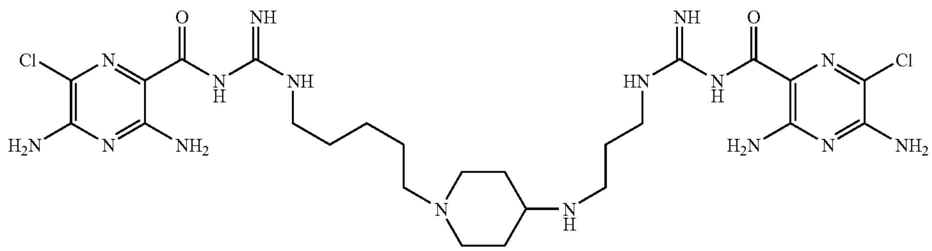 | 6 or 8f |
| 905 | 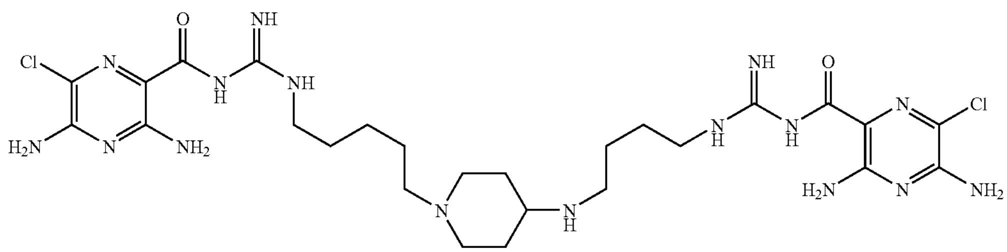 | 6 or 8f |
| 906 | 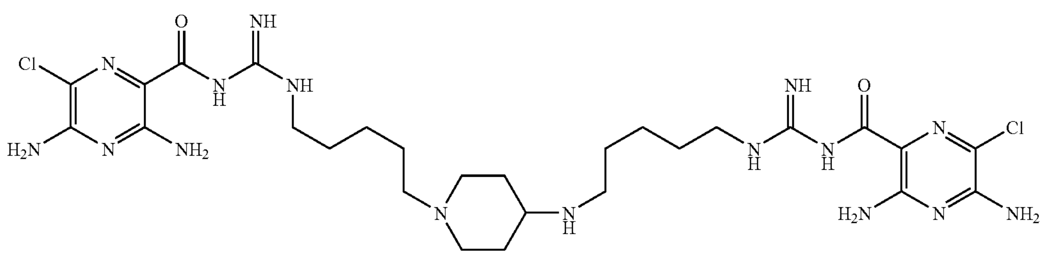 | 6 or 8f |
| 907 | 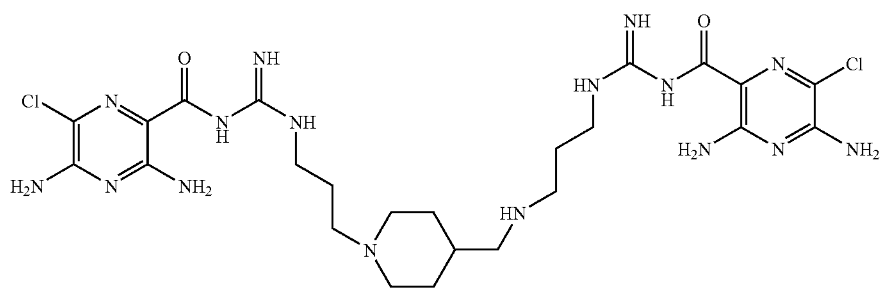 | 6 or 8f |
| 908 | 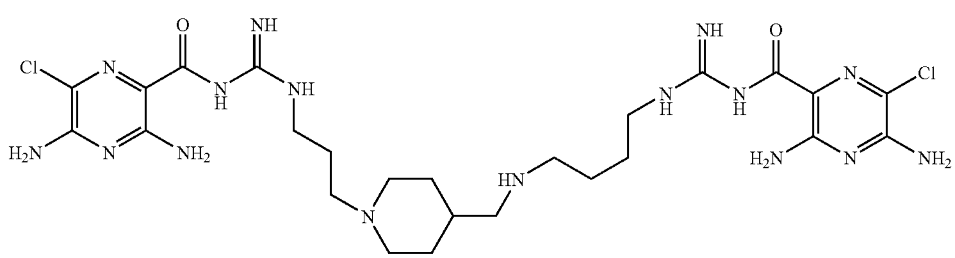 | 6 or 8f |

TABLE 10-continued

| Ex. | Structure | Viable Preparation Routes |
|---|---|---|
| 909 | 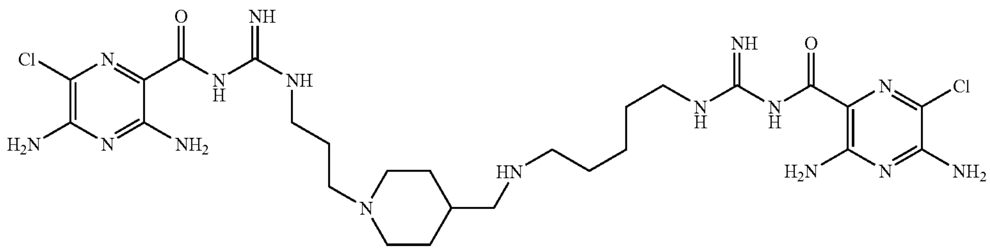 | 6 or 8f |
| 910 | 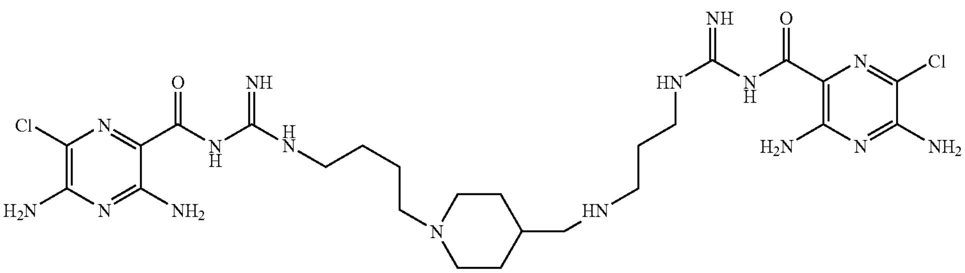 | 6 or 8f |
| 911 | 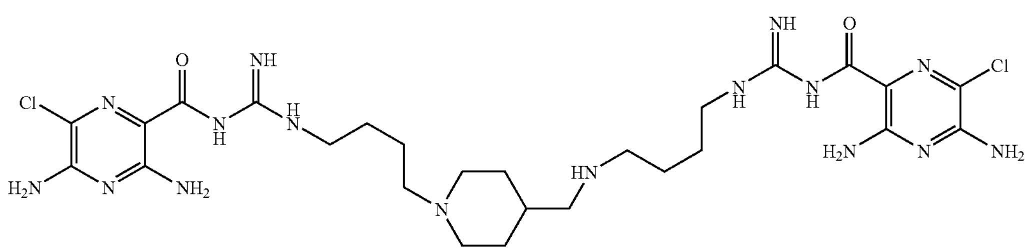 | 6 or 8f |
| 912 | 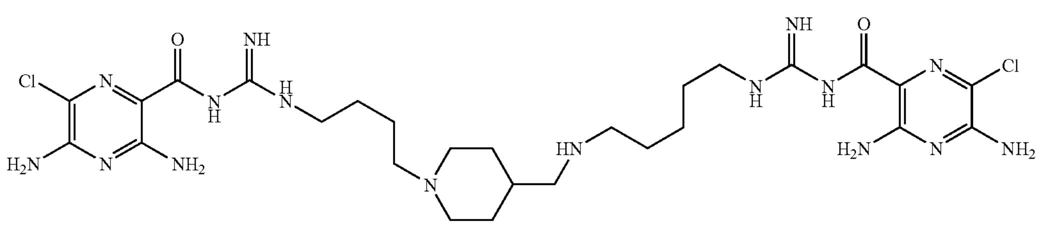 | 6 or 8f |
| 913 | 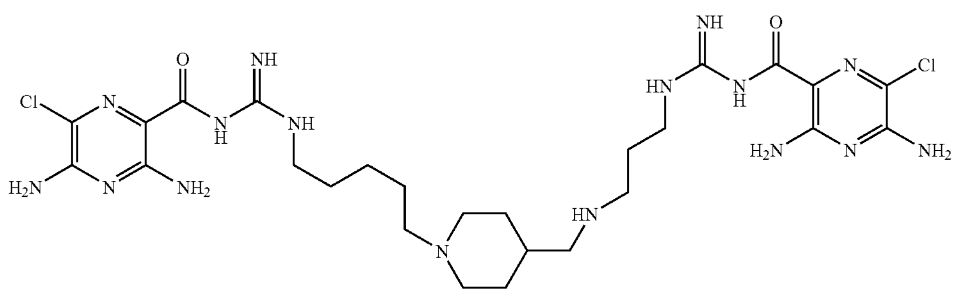 | 6 or 8f |

TABLE 10-continued

| Ex. | Structure | Viable Preparation Routes |
|---|---|---|
| 914 | 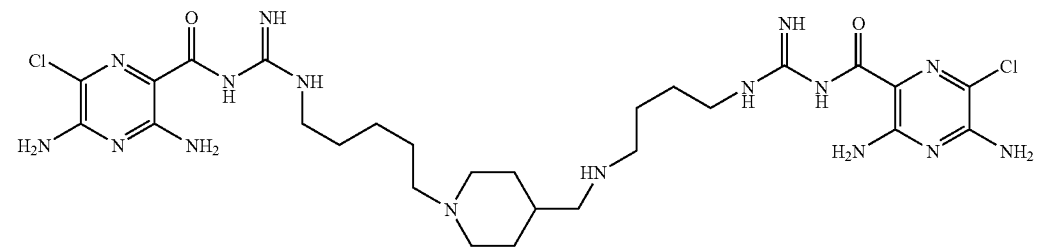 | 6 or 8f |
| 915 | 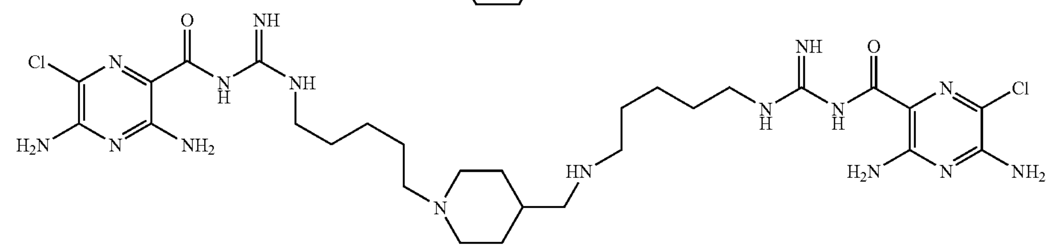 | 6 or 8f |

Preparation of Intermediates

Intermediate A

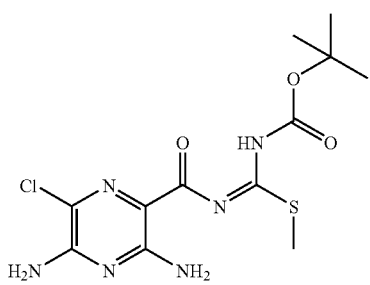

A stirred suspension comprising 1-(3,5-diamino-6-chloro-pyrazine-2-carbonyl)-2-methyl-isothiourea hydroiodide (11.4 g, 29 mmol), 4-dimethylaminopyridine (0.87 g, 7 mmol), $Et_3N$ (20 mL) in THF (400 mL) is treated with di-tertbutyl dicarbonate (12 g, 55 mmol) in THF (100 mL) in one portion. The resulting mixture is stirred at RT overnight and then concentrated in vacuo. The crude product is partitioned between EtOAc (50 mL) and water (50 mL) and stirred at RT for 10 minutes. The suspension is filtered, washed with water (5 mL), EtOAc (20 mL) and dried under vacuum at 40° C. to afford the title compound. $[M+H]^+$ 361.05

Intermediate B

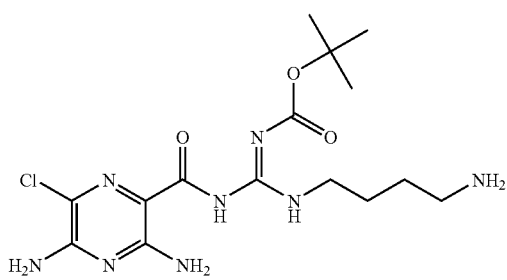

Step 1:

A solution comprising Intermediate A (6.55 g, 18.2 mmol), N-Z-1,4-diaminobutane hydrochloride (4.7 g, 18.2 mmol) and $Et_3N$ (20 mL) in DMF (300 mL) is stirred at RT overnight. The solvent is removed in vacuo and the crude residue is dissolved in EtOAc (700 mL) and washed with water (2×200 mL), brine (100 mL), dried ($MgSO_4$) and concentrated in vacuo. Purification by recrystallisation of the product from EtOAc (400 mL) affords the product as a yellow solid.

Step 2:

A suspension (6.7 g, 12.5 mmol) in MeOH (500 mL) is warmed to 40° C. to form a turbid solution. The solution is placed under an atmosphere of argon and treated with 10% palladium on carbon. The mixture is then placed under an atmosphere of hydrogen overnight and then filtered. The filtrate is concentrated in vacuo and the resulting solid is suspended in EtOAc (20 mL) and filtered to afford the title compound as a green solid. $[M+H]^+$ 401.34

Intermediate C
N,N'-Bis-(4-amino-butyl)terephthalamide

Step 1: {4-[4-(4-tert-Butoxycarbonylamino-butylcarbamoyl)-benzoylamino]-butyl}-carbamic acid tert-butyl ester A solution of terephthaloyl chloride (5.0 g, 0.0246 mol) in dry DMF (100 mL) is treated with N-Boc-1,4-diaminobutane (9.418 mL, 0.0493 mol) and stirred at RT for 30 minutes. $Et_3N$ (10.298 mL, 0.0739 mol) is added and stirring continues overnight. The resulting mixture is diluted with deionised water (100 mL) and after stirring at RT for 30 minutes, the mixture is filtered. The filter cake is washed with water and dried in vacuo (40° C.) to afford the title compound.

Step 2: N,N'-Bis-(4-aminobutyl)-terephthalamide

{4-[4-(4-tert-Butoxycarbonylamino-butylcarbamoyl)-benzoylamino]-butyl}-carbamic acid tert-butyl ester (0.49 g) is treated with neat TFA (5 mL) and allowed to stand at RT overnight. The acid is removed in vacuo to afford the title compound as a yellow solid. Alternatively, deprotection can be carried out using 33% HBr is acetic acid. [M+H]$^+$ 307.22

Intermediate D N*1*-{3-[(3-Amino-propyl)benzyl-amino]-propyl}-N*1*benzyl-propane-1,3-diamine dihydrochloride

Step 1: 3-(Benzyl-{3-[benzyl-(2-cyano-ethyl)-amino]-propyl}-amino)-propionitrile A suspension comprising N,N'-dibenzyl-propane-1,3-diamine dihydrochloride (31 g, 95 mmol) and sodium acetate (15.6 g, 190 mmol) in MeOH (315 mL) is treated with acetic acid (5.7 mL) followed by dropwise addition of acrylonitrile over 20 minutes. The resulting suspension is stirred at 70° C. for 10 hours and then at RT for 10 hours. The suspension is removed by filtration and washed with a small volume of MeOH. The filtrate is concentrated in vacuo and the crude residue is dissolved in ether and washed with sodium carbonate solution. The organic portion is dried (MgSO$_4$) and concentrated in vacuo. Purification of the crude product by chromatography on silica eluting with 1:1 hexane:EtOAc affords the title compound as a yellow oil.

Step 2: N*1*-{3-[(3-Amino-propyl)-benzyl-amino]-propyl}-N*1*-benzyl-propane-1,3-diamine dihydrochloride A solution of 3-(benzyl-{3-[benzyl-(2-cyano-ethyl)-amino]-propyl}-amino)-propionitrile (26.6 g, 73.8 mmol)) in EtOH (500 mL) is treated with Raney Nickel (10 g) and placed under an atmosphere of hydrogen at RT for 20 hours. The reaction mixture is filtered and the filtrate is concentrated in vacuo. The crude residue is dissolved in EtOH (100 mL) and treated with 1.8 M ethanolic HCl. The resulting suspension is cooled to 0° C. and collected by filtration. The solid is washed with cold EtOH/ether and dried under vacuum to afford the title compound.

Intermediate E N,N'-Bis-(2-amino-ethyl)-2,3-dihydroxy-terephthalamide dihydrochloride A solution of 2,3-dihydroxy-terephthalic acid dimethyl ester (2.26 g, 10 mmol) in ethylenediamine (50 mL) is heated at reflux overnight. After cooling to RT, the solvent is removed in vacuo and the crude residue is dissolved in MeOH (50 mL). The solution is cooled with an ice-bath and HCl gas is passed through the solution until the pH is adjusted to pH7. The resulting suspension is filtered and washed with cold MeOH to afford the title compound.

Intermediate F

To a stirred solution of 1-(3,5-diamino-6-chloro-pyrazine-2-carbonyl)-2-methyl-isothiourea hydroiodide (50 g, 0.129 mol) in dry THF (1 L) is added Et$_3$N (18 mL, 0.129 mol), followed by N-(benzyloxycarbonyloxy)-succinimide (32.1 g, 0.129 mol). The reaction mixture is then heated to reflux (66° C.) for 6 hours. The reaction is allowed to cool to RT, then concentrated in vacuo to a yellow solid. The crude is suspended in EtOAc (500 mL) and water (500 mL) and is triturated vigorously for a period of 30 minutes. The resulting suspension is filtered and dried in a vacuum oven (40° C.) over P$_2$O$_5$ to give the product as a pale yellow solid. A second crop (10 g) was obtained from then EtOAc layer after it was cooled (4° C.) over a 48 hour period. (MH$^+$; 394.77 and 396.79)

Intermediate G

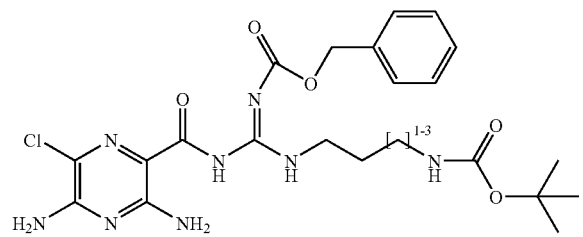

Intermediate F (1 eq) is added to a stirring solution of the appropriate mono-Boc protected amine (e.g., propane diamine, butane diamine or pentane diamine) (1 eq) in THF (20 vol). The reaction is heated at 60° C. for 8 hours. The crude product is isolated by filtration from the cooled reaction mixture and purified by flash column chromatography eluting with (9:1 DCM:MeOH).

Intermediate H

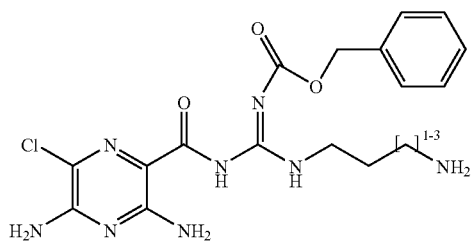

Intermediate G is deprotected using a 1:1 solution of TFA and DCM (20 vol). Neutralisation with NaHCO$_3$ solution and extraction with DCM yields the desired product upon concentration in vacuo.

Intermediate J

Amino propanol or amino butanol or amino pentanol (1 eq) is added to a stirring solution of Intermediate F (1 eq) in THF (10 vol). On completion the reaction mixture is diluted with EtOAc and washed with 5% citric acid solution, brine and water. The organic phase is concentrated in vacuo and the resulting material is used crude or purified using flash column chromatography.

Intermediate K

Methane sulfonyl chloride (1 eq) is added to a stirring solution of Intermediate J (1 eq) and Et$_3$N (3 eq) in DCM. Upon completion the reaction is quenched with NaHCO$_3$ solution. The DCM layer is dried over magnesium sulfate and concentrated in vacuo to produce a crude residue which is purified by flash column chromatography.

Intermediate M

Methane sulfonyl chloride (1 eq) was added to a stirring solution of N-Boc propan-1-ol, N-Boc butan-1-ol or N-Boc pentan-1-ol (1 eq) and Et$_3$N (3 eq) in DCM. Upon completion the reaction was quenched with NaHCO$_3$ solution. The DCM layer was dried over magnesium sulfate and concentrated in vacuo to produce a crude residue which was used crude or purified by flash column chromatography.

Intermediate N

Step 1a

The di-acid chloride or tri-acid chloride (1 eq) was added to a stirred solution of N-Boc propyldiamine, N-Boc butyldiamine or N-Boc pentyldiamine (2 eq) and Et$_3$N (3 eq) in DMF (10 vol). Upon completion of the reaction the solution was quenched with aqueous NaHCO$_3$ and the product (Intermediate Na) extracted with DCM and concentrated in vacuo.

Step 1b

EDCl (1 eq) was added to a stirred solution of the di-acid or tri-acid (1 eq) in DMF (10 vol). N-ethyl-morpholine (3 eq) and N-Boc propyldiamine, N-Boc butyldiamine or N-Boc pentyldiamine (2 eq) were added and the reaction heated. Upon completion the reaction was quenched with NaHCO$_3$ solution and the product (Intermediate Nb) extracted with DCM and concentrated in vacuo.

Step 1c

The di-isocyanate (1 eq) was added to a stirred solution of N-Boc propyldiamine, N-Boc butyldiamine or N-Boc pentyldiamine (1 eq) and Et$_3$N (2.5 eq) in DCM (40 vol). The reaction was heated to reflux for 8 hours and the product (Intermediate Nc) isolated by filtration.

Step 1d

Diphenylphosphorylazide (1 eq) was added to a stirred solution of the di-acid or tri-acid (1 eq), Et$_3$N (2 eq) and N-Boc propyldiamine, N-Boc butyldiamine or N-Boc pentyldiamine in DCM (40 vol). The reaction was heated to reflux for 8 hours. The product (Intermediate Nd) was isolated from the cooled reaction mixture by filtration or purified by flash column chromatography.

Step 1e

The diamine (1 eq) is added a solution of bis-4-nitrophenylcarbonate (2 eq) in DMF. The reaction is left to stir for 1-2 hours and N-Boc propyldiamine, N-Boc butyldiamine or N-Boc pentyldiamine is added and the reaction heated. Upon completion the reaction is quenched with water and the crude product (Intermediate Ne) isolated by filtration and purified by flash column chromatography.

Step 1f

N-Boc propylamine methane sulfonate, N-Boc butylamine methane sulfonate or N-Boc pentylamine methane sulfonate (2 eq) is added to a stirring solution of the diamine (1 eq) and triethylaine (2 eq) in DMF. Upon completion the reaction is quenched with water and the product (Intermediate Ng) isolated by filtration or extraction with DCM or by flash column chromatography.

Intermediate N (Prepared from Intermediate M)

The di-sulfonyl chloride (1 eq) is added to a stirring solution of Intermediate M (2 eq) in DMF. Upon completion the reaction was quenched with water the product (Intermediate N) isolated by filtration or by flash column chromatography.

Intermediate O

Intermediate N is dissolved in DCM (5 vol) and TFA (2-5 vol) is added. Upon completion the product (Intermediate O) is isolated by concentration and toluene azeotrope.

Intermediate P
5-[4-(5-Amino-pentyl)-piperazin-1-yl]-pentylamine

Step 1: (5-Methanesulfonylamino-pentyl)-carbamic acid tert-butyl ester

Methane sulfonyl chloride (0.4 mL, 5.3 mmol) is added to a stirring solution of Boc-amino pentanol (1.0 g, 4.9 mmol) and Et$_3$N (1.68 mL, 15 mmol) in DCM (10 mL). The reaction is left to stir at RT for 1 hour and is then quenched with sodium hydrogen carbonate solution and the organic phase washed with 5% citric acid solution. The resulting organic phase is dried over magnesium sulphate and concentrated in vacuo to yield the title compound as a viscous yellow oil.

Step 2: {5-[4-(5-tert-Butoxycarbonylamino-pentyl)-piperazin-1-yl]-pentyl}-carbamic acid tert-butyl ester (5-Methanesulfonylamino-pentyl)-carbamic acid tert-butyl ester (500 mg, 1.7 mmol) is dissolved in DMF (10 mL) and Et$_3$N (0.286 mL, 2.6 mmol) and piperazine (73 mg, 0.85 mmol) added. The reaction was heated to 10° C. for 4 hours and then quenched with water on cooling. The reaction mixture is extracted with DCM and the organic portion is concentrated in vacuo and dried under vacuum to afford the title compound as a solid.

Step 3: 5-[4-(5-Amino-pentyl)-piperazin-1-yl]-pentylamine trifluoroacetate

A solution of {5-[4-(5-tert-butoxycarbonylamino-pentyl)-piperazin-1-yl]-pentyl}-carbamic acid tert-butyl ester (329 mg, 0.72 mmol) in DCM (10 mL) is treated with trifluoracetic acid (1 mL). The reaction was left to stir at RT for 4 days and then the solvent is removed in vacuo. The material was used crude and conversion was assumed quantitative to produce 5-[4-(5-amino pentyl)-piperazin-1-yl]-pentylamine.

Intermediate Q

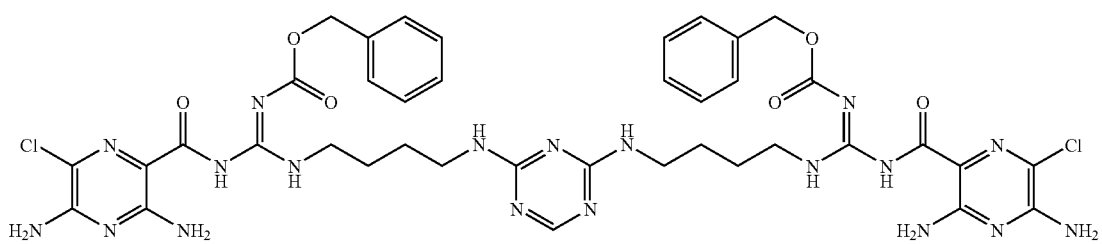

2,4-Dichloro-1,3,5-triazine (15.5 mg, 010 mmol) is dissolved in N-methyl-2-pyrrolidone (2 mL) and cooled to 0° C. A solution of Intermediate H (90 mg, 0.21 mmol) in N-methyl-2-pyrrolidone (1 mL) is added to the reaction mixture and stirred over night at RT. The reaction mixture is purified by reverse phase column chromatography (Isolute™ C18, 0-100% acetonitrile in water—0.1% TFA). The acetonitrile is then removed from the clean fractions in vacuo and the resulting aqueous solution is partitioned between dichloromethane and NaHCO$_{3(aq)}$. The solid that forms between the two layers is filtered off and dried in vacuo to yield the title compound. (MH$^+$ 946.4)

Intermediates R

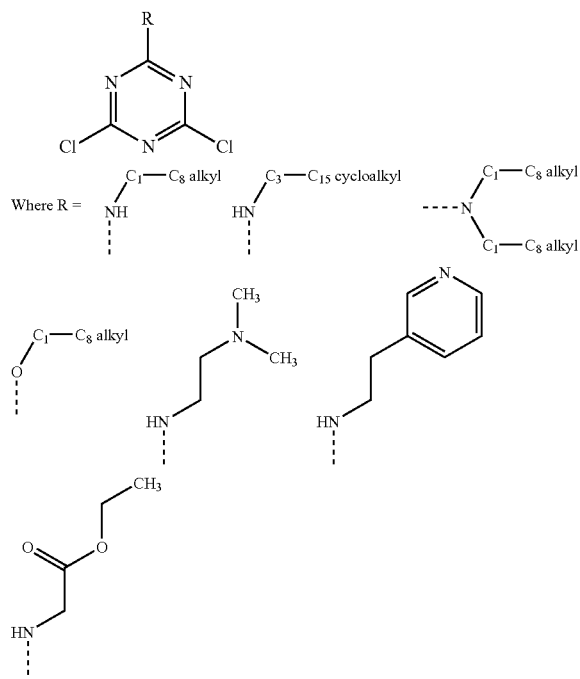

Intermediates R are prepared using the procedure of Rankovic, Zoran; Cai, Jiaqiang; Cumming, Iain. Preparation of 2-cyano-1,3,5-triazine-4,6-diamine derivatives for the treatment of osteoporosis and atherosclerosis. (WO 2005/011703 A1, page 6).

Intermediates S

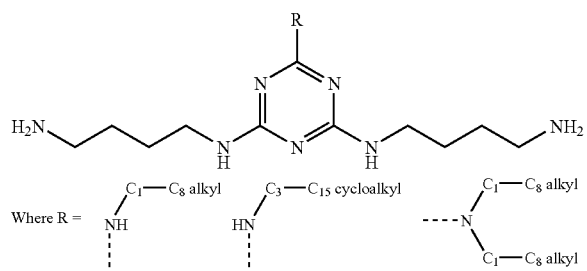

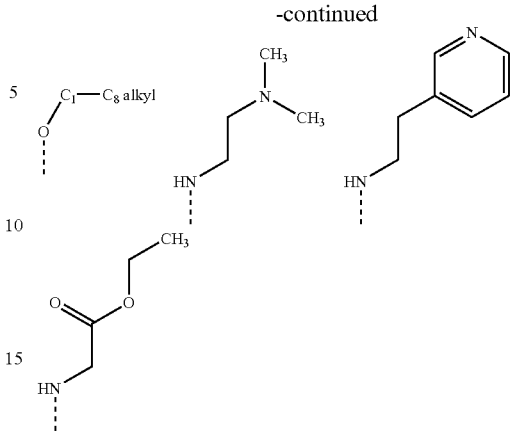

These Intermediates are prepared by reacting Intermediates R with 2 equivalents of (4-aminobutyl)carbamic acid tertbutyl ester at 60° C. for 1 hour in N-methyl-2-pyrrolidone followed by addition of 4 M HCl (in dioxane) and stirring over night. Purification by conventional techniques afford the required triazine diamine product.

The invention claimed is:
1. A compound of formula (I)

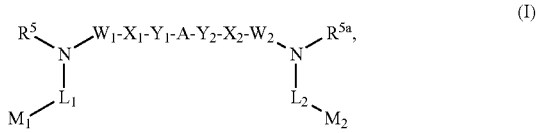

or tautomers, or stereoisomers, or pharmaceutically acceptable salts thereof,
wherein
$M_1$ and $M_2$ are independently

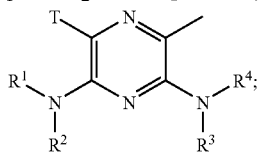

$R^1$, $R^2$, $R^3$, $R^4$, $R^5$, $R^{5a}$, $R^{5b}$ and $R^6$ are H;
$L_1$ and $L_2$ are independently selected from:

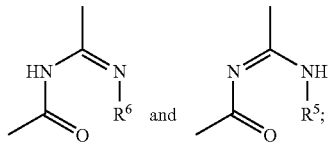

A is phenyl;
$W_1$ and $W_2$ are independently selected from $C_0$-$C_8$-alkylene;
$X_1$ is —NR$^7$(C=O)— and $X_2$ is —(C=O)NR$^7$—, independently, by way of a $C_1$-$C_4$-alkyl group can form a bond with a carbon atom of group W or Y to create a 5- to 14-membered heterocyclic group;
$R^7$ is independently selected from H, and $C_1$-$C_8$-alkyl;
$Y_1$ and $Y_2$ are independently selected from —($C_0$-$C_8$-alkylene)-; and
T is a halogen.
2. A pharmaceutical composition comprising a compound according to claim 1 together with a pharmaceutical acceptable excipient.

3. A process for the preparation of compounds of the formula (I), according to claim 1:
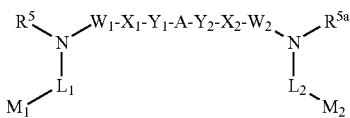 (I)
wherein the process comprises the steps of
(i) reacting a compound of the formula (IV):
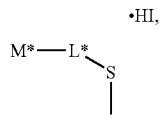 (IV)
wherein
$M^*$ is $M_1$ or $M_2$;
$L^*$ is $L_1$ or $L_2$;
with a compound of the formula (V):
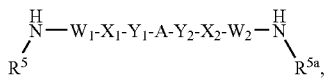 (V)
and
(ii) recovering the resultant compound of formula (I), in free or pharmaceutically acceptable salt form.
* * * * *